United States Patent
Carter et al.

(10) Patent No.: US 9,061,074 B2
(45) Date of Patent: *Jun. 23, 2015

(54) VARIANT TARGET BINDING AGENTS AND USES THEREOF

(71) Applicant: Seattle Genetics, Inc., Bothell, WA (US)

(72) Inventors: Paul Carter, San Mateo, CA (US); Django Sussman, Seattle, WA (US)

(73) Assignee: Seattle Genetics, Inc., Bothell, WA (US)

(*) Notice: Subject to any disclaimer, the term of this patent is extended or adjusted under 35 U.S.C. 154(b) by 127 days.

This patent is subject to a terminal disclaimer.

(21) Appl. No.: 13/826,260

(22) Filed: Mar. 14, 2013

(65) Prior Publication Data

US 2014/0105922 A1 Apr. 17, 2014

Related U.S. Application Data

(63) Continuation of application No. 12/516,914, filed as application No. PCT/US2007/086205 on Dec. 1, 2007, now Pat. No. 8,455,622.

(60) Provisional application No. 60/918,563, filed on Mar. 16, 2007, provisional application No. 60/872,239, filed on Dec. 1, 2006.

(51) Int. Cl.

| C07K 16/00 | (2006.01) |
| A61K 39/395 | (2006.01) |
| A61K 39/40 | (2006.01) |
| A61K 47/48 | (2006.01) |
| A61K 51/10 | (2006.01) |
| C07K 16/28 | (2006.01) |
| C07K 1/00 | (2006.01) |

(52) U.S. Cl.
CPC ....... *A61K 47/4863* (2013.01); *A61K 47/48415* (2013.01); *A61K 47/48561* (2013.01); *A61K 51/1027* (2013.01); *C07K 16/2875* (2013.01); *C07K 2317/24* (2013.01); *C07K 2317/41* (2013.01); *C07K 2317/53* (2013.01); *C07K 2317/56* (2013.01); *C07K 2317/565* (2013.01); *C07K 2317/71* (2013.01); *C07K 2317/732* (2013.01); *C07K 2317/734* (2013.01); *C07K 2317/92* (2013.01); *C07K 2317/52* (2013.01); *A61K 47/48569* (2013.01)

(58) Field of Classification Search
None
See application file for complete search history.

(56) References Cited

U.S. PATENT DOCUMENTS

| 5,219,996 A | 6/1993 | Bodmer et al. |
| 5,624,821 A | 4/1997 | Winter et al. |
| 6,528,624 B1 | 3/2003 | Idusogie et al. |
| 6,737,056 B1 | 5/2004 | Presta et al. |
| 7,297,775 B2 | 11/2007 | Idusogie et al. |
| 7,332,581 B2 | 2/2008 | Presta et al. |
| 7,491,390 B2 | 2/2009 | Law et al. |
| 7,498,298 B2 | 3/2009 | Doronina et al. |
| 7,968,687 B2 | 6/2011 | McDonagh et al. |
| 8,242,252 B2 | 8/2012 | McDonagh et al. |
| 8,455,622 B2 * | 6/2013 | McDonagh et al. ........ 530/387.1 |
| 2004/0132101 A1 | 7/2004 | Lazar et al. |
| 2006/0083736 A1 | 4/2006 | Law et al. |
| 2006/0134709 A1 | 6/2006 | Stavenhagen et al. |
| 2007/0092940 A1 | 4/2007 | Eigenbrot et al. |
| 2007/0269369 A1 | 11/2007 | Gegg et al. |
| 2010/0158909 A1 | 6/2010 | McDonagh et al. |
| 2012/0294853 A1 | 11/2012 | McDonagh et al. |

FOREIGN PATENT DOCUMENTS

| WO | WO03/074679 A2 | 9/2003 |
| WO | WO2004/042017 A2 | 5/2004 |
| WO | WO2004/073656 A2 | 9/2004 |
| WO | WO2005/018572 A2 | 3/2005 |
| WO | WO2006/034488 A2 | 3/2006 |
| WO | WO2006/074397 A2 | 7/2006 |
| WO | WO2006/113909 A2 | 10/2006 |
| WO | WO2008/020827 A2 | 2/2008 |

OTHER PUBLICATIONS

Armour et al., "Recombinant human IgG molecules lacking Fcγ receptor 1 binding and monocyte triggering activities," Eur. J. Immunol. 29:2613-2624, 1999.
Caron et al., "Engineered humanized dimeric forms of IgG are more effective antibodies," J. Exp. Med. 176:1191-1195, 1992.
Hutchins et al., "Improved biodistribution, tumor targeting, and reduced immunogenicity in mice with a γ4 variant of Campath-1H," Proc. Natl. Acad. Sci. USA 92:11980-11984, 1995.
Lyons et al., "Site-specific attachment to recombinant antibodies via introduced surface cysteine residues," Protein Eng. 3:703-708, 1990.
McDonagh et al., "Engineered anti-CD70 antibody-drug conjugate with increased therapetuc index," Mol. Cancer There. 7:2913-2923, 2008.
Shopes, "A genetically engineered human IgG mutant with enhanced cytolytic activity," J. Immunol. 148:2918-2922, 1992.
Shopes, "A genetically engineered human IgG with limited flexibility fully initiates cytolysis via complement," Mol. Immunol. 30:603-609, 1993.
Stavenhagen et al., "Fc optimization of the therapeutic antibodies enhances their ability to fill tumor cells in vitro and controls tumor expansion in vivo via low-affinity activating Fcγ receptors," Cancer Res. 67:8882-8890, 2007.
Stimmel et al., "Site-specific conjugation on serine—cysteine variant monlconal antibodies," J. Biol. Chem. 275:30445-30450, 2000.
Vietta et al., "Considering Therapeutic Antibodies," Science 313:308-309, 2006.
Denny, "DNA minor groove alkylating agents," Exp. Opin. Ther. Patents 10(4):459-474, 2000.
Sussman, et al., "Engineered Cysteine Antibodies: Improved Antibody-Drug conjugate Vehicles," Poster presentation of Abstract No. B204, 102nd annual Meeting of the American Association for Cancer Research, Apr. 2-6, 2011, Orlando, FL.

* cited by examiner

*Primary Examiner* — Chun Dahle
(74) *Attorney, Agent, or Firm* — Seattle Genetics, Inc.

(57) ABSTRACT

The present invention provides variant target binding agents and methods relating to the use of such binding agents for the prophylaxis or treatment of cancers and immunological disorders. The variant target binding agent is conjugated to a therapeutic agent that exerts a cytotoxic, cytostatic, or immunomodulatory effect on target cells.

19 Claims, 12 Drawing Sheets

Figure 2

Amino Acid Sequences of the Constant Domains of the IgG1, IgG2, IgG3 and IgG4

A. IgG1

ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

B. IgG2

ASTKGPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWLNGKEYKCKVSNKGLPAP
IEKTISKTKGQPREPQVYTLPPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK

C. IgG3

QMQGVNCTVSSELKTPLGDTTHTCPRCPEPKSCDTPPPCPRCPEPKSCDTPPPCPRCPEPKSCDTPPCP
RCPAPELLGGPSVFLFPPKPKDTLMISRTPEVTCVVVDVSHEDPEVQFKWYVDGVQVHNAKTKPREQQFN
STFRVVSVLTVLHQNWLDGKEYKCKVSNKALPAPIEKTISKTKGQPREPQVYTLPPSREEMTKNQVSLTC
LVKGFYPSDIAVEWESSGQPENNYNTTPPMLDSDGSFFLYSKLTVDKSRWQQGNIFSCSVMHEALHNRFT
QKSLSLSPGK

D. IgG4

ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

Figure 3

Amino Acid Sequences of the hIF6 IgG1, IgG2 and IgG4 Isotype Variants

A. h1F6 IgG1

MAWVWTLLFLMAAAQSAQAQVQLVQSGAEVKKPGASVKVSCKASGYTFTNYGMNWVRQAPGQGLKWMGWI
NTYTGNPTYADAFKGRVTMTRDTSISTAYMELSRLRSDDTAVYYCARDYGDYGMDYWGQGTTVTVSSAST
KGPSVFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

B. h1F6 IgG2

MAWVWTLLFLMAAAQSAQAQVQLVQSGAEVKKPGASVKVSCKASGYTFTNYGMNWVRQAPGQGLKWMGWI
NTYTGNPTYADAFKGRVTMTRDTSISTAYMELSRLRSDDTAVYYCARDYGDYGMDYWGQGTTVTVSSAST
KGPSVFPLAPCSRSTSESTAALGCLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVFLFPPKPKDTLMISRTPEVTCVVV
DVSHEDPEVQFNWYVDGVEVHNAKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWESNGQPENNYKTTPPMLDSDGSF
FLYSKLTVDKSRWQQGNVFSCSVMHEALHNHYTQKSLSLSPGK

B. h1F6 IgG4

MAWVWTLLFLMAAAQSAQAQVQLVQSGAEVKKPGASVKVSCKASGYTFTNYGMNWVRQAPGQGLKWMGWI
NTYTGNPTYADAFKGRVTMTRDTSISTAYMELSRLRSDDTAVYYCARDYGDYGMDYWGQGTTVTVSSAST
KGPSVFPLAPCSRSTSESTAALGCLVKDYFPEPVTVSWNSGALTSGVHTFPAVLQSSGLYSLSSVVTVPS
SSLGTKTYTCNVDHKPSNTKVDKRVESKYGPPCPSCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK

Figure 4

Amino Acid Sequences of the h1F6 IgG1v1 and IgG4v3 Fc Domain Variants

A. h1F6 IgG1v1

MAWVWTLLFLMAAAQSAQAQVQLVQSGAEVKKPGASVKVSCKASGYTFTNYGMNWVRQAPGQGLKWMGWI
NTYTGNPTYADAFKGRVTMTRDTSISTAYMELSRLRSDDTAVYYCARDYGDYGMDYWGQGTTVTVSSAST
KGPSVFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPPVAGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

B. h1F6 IgG4v3

MAWVWTLLFLMAAAQSAQAQVQLVQSGAEVKKPGASVKVSCKASGYTFTNYGMNWVRQAPGQGLKWMGWI
NTYTGNPTYADAFKGRVTMTRDTSISTAYMELSRLRSDDTAVYYCARDYGDYGMDYWGQGTTVTVSSAST
KGPSVFPLAPCSRSTSESTAALGCLVKDYFPEPVTVSWNSGALTSGVHTFPAVLQSSGLYSLSSVVTVPS
SSLGTKTYTCNVDHKPSNTKVDKRVESKYGPPCPPCPAPEFAGAPSVFLFPPKPKDTLMISRTPEVTCVV
VDVSQEDPEVQFNWYVDGVEVHNAKTKPREEQFNSTYRVVSVLTVLHQDWLNGKAYKCKVSNKGLPSSIE
KTISKAKGQPREPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK

G1v1: E233P, L234V, L235A (impaired FcγR binding)
G4v3: S228P, L235A, G237A, E318A (impaired FcγR binding)

h1F6 Variant Binding Affinity

|  | AF488/Ab | Mean KD | Std Dev |
|---|---|---|---|
| h1F6 G1 | 3.4 | 1.27 | 0.12 |
| h1F6 G1v1 | 3.6 | 1.13 | 0.25 |
| h1F6 G2 | 4.4 | 0.95 | 0.31 |
| h1F6 G4 | 4.2 | 1.14 | 0.34 |
| h1F6 G4v3 | 4.3 | 1.30 | 0.08 |

CHO FcγRIIIa Cell Lines

FACS analysis of FCγRIIIa expressing cell lines using anti-human FcγRIIIa-PE

CHO FcγRIIIa Saturation Binding

Saturation binding assay using AF488 labeled h1F6 read on the LSRII

FcγRIIIa (158V) Interactions

Conjugation does not impair h1F6 G1 interactions with FcγRIIIa

FcγRI Interactions

Conjugation does not impair h1F6 G1 or h1F6 G4 interaction with FcγRI

*In Vivo* Activity of h1F6 variant ADCs

In Vivo Efficacy of h1F6 Variant ADCs

Pharmacokinetics of h1F6 Variant ADCs

- h1F6 G1 vcMMAF4
- h1F6 G1v1 vcMMAF4
- h1F6 G2 vcMMAF4
- h1F6 G4 vcMMAF4
- h1F6 G4v3 vcMMAF4

10 mg/kg single dose
Nude mice n = 3

|  | h1F6 variant vcMMAF4 | | | | |
|---|---|---|---|---|---|
|  | G1 | G1v1 | G2 | G4 | G4v3 |
| AUC (μg-ml/day) | 200 ± 40 | 432 ± 33 | 469 ± 199 | 204 ± 129 | 97 |
| Terminal half life (days) | 5.4 ± 1.9 | 5.3 ± 1.2 | 5.9 ± 2.0 | 2.8 ± 0.6 | 3.7 |

Efficacy: G1v1 ~ G2 > G1 > G4 ~ G4v3

SEQUENCE LISTING

<160> NUMBER OF SEQ ID NOS: 39

<210> SEQ ID NO 1
<211> LENGTH: 411
<212> TYPE: DNA
<213> ORGANISM: Mus musculus

<400> SEQUENCE: 1

```
atggcttggg tgtggacctt gctattcctg atggcagctg cccaaagtgc ccaagcacag        60
atccagttgg tgcagtctgg acctgaggtg aagaagcctg gagagacagt caagatctcc       120
tgcaaggctt ctgggtatac cttcacaaac tatggaatga ctgggtgaa gcaggctcca        180 ggaaagggtt taaagtggat gggctggata aacacctaca ctggagagcc aacatatgct       240
gatgccttca agggacggtt tgccttctct ttggaaacct ctgccagcac tgcctatttg       300
cagatcaaca acctcaaaaa tgaggacacg gctacatatt tctgtgcaag agactacggc       360
gactatggta tggactactg gggtcaagga acctcagtca ccgtctcctc a                411
```

<210> SEQ ID NO 2
<211> LENGTH: 137
<212> TYPE: PRT
<213> ORGANISM: Mus musculus

<400> SEQUENCE: 2

```
Met Ala Trp Val Trp Thr Leu Leu Phe Leu Met Ala Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110
```

Tyr Phe Cys Ala Arg Asp Tyr Gly Asp Tyr Gly Met Asp Tyr Trp Gly
            115                 120                 125

Gln Gly Thr Ser Val Thr Val Ser Ser
    130                 135

<210> SEQ ID NO 3
<211> LENGTH: 1404
<212> TYPE: DNA
<213> ORGANISM: Artificial
<220> FEATURE:
<223> OTHER INFORMATION: murine CDR, human FR in HV Domain

<400> SEQUENCE: 3

| | | | | | |
|---|---|---|---|---|---|
| atggcttggg | tgtggacctt | gctattcctg | atggcagctg | cccaaagtgc | ccaagcacag | 60 |
| gttcagctgg | tgcagtctgg | agctgaggtg | aagaagcctg | ggcctcagt | gaaggtctcc | 120 |
| tgcaaggctt | ctggttacac | ctttaccaac | tatggaatga | actgggtgcg | acaggcccct | 180 |
| ggacaagggc | ttgagtggat | gggatggatc | aacacctaca | ctggagagcc | aacatatgct | 240 |
| gatgccttca | agggcagagt | caccatgacc | acagacacat | ccacgagcac | agcctacatg | 300 |
| gagctgagga | gcctgagatc | tgacgacacg | gccgtgtatt | actgtgcgag | agactacggc | 360 |
| gactatggta | tggactactg | gggtcaagga | accaccgtca | ccgtctcctc | agctagcacc | 420 |
| aagggcccat | cggtcttccc | cctggcaccc | tcctccaaga | gcacctctgg | ggcacagcg | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | aagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaag | 1020 |
| tgcaaggtct | ccaacaaagc | cctcccagcc | cccatcgaga | aaaccatctc | caaagccaaa | 1080 |
| gggcagcccc | gagaaccaca | ggtgtacacc | ctgcccccat | cccgggatga | gctgaccaag | 1140 |
| aaccaggtca | gcctgacctg | cctggtcaaa | ggcttctatc | cagcgacat | cgccgtggag | 1200 |
| tgggagagca | atgggcagcc | ggagaacaac | tacaagacca | cgcctcccgt | gctggactcc | 1260 |
| gacggctcct | tcttcctcta | cagcaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctccgggtaa | atga | | | | 1404 |

<210> SEQ ID NO 4
<211> LENGTH: 467
<212> TYPE: PRT
<213> ORGANISM: Artificial
<220> FEATURE:
<223> OTHER INFORMATION: murine CDR, human FR in HV Domain

<400> SEQUENCE: 4

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

-continued

```
Pro Gly Ala Ser Val Lys Val Ser Cys Lys Ala Ser Gly Tyr Thr Phe
            35                  40                  45
Thr Asn Tyr Gly Met Asn Trp Val Arg Gln Ala Pro Gly Gln Gly Leu
 50                  55                  60
Glu Trp Met Gly Trp Ile Asn Thr Tyr Thr Gly Glu Pro Thr Tyr Ala
 65                  70                  75                  80
Asp Ala Phe Lys Gly Arg Val Thr Met Thr Thr Asp Thr Ser Thr Ser
                    85                  90                  95
Thr Ala Tyr Met Glu Leu Arg Ser Leu Arg Ser Asp Asp Thr Ala Val
                100                 105                 110
Tyr Tyr Cys Ala Arg Asp Tyr Gly Asp Tyr Gly Met Asp Tyr Trp Gly
            115                 120                 125
Gln Gly Thr Thr Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
                180                 185                 190
Val Leu Gln Ser Ser Gly Leu Tyr Ser Leu Ser Ser Val Val Thr Val
            195                 200                 205
Pro Ser Ser Ser Leu Gly Thr Gln Thr Tyr Ile Cys Asn Val Asn His
210                 215                 220
Lys Pro Ser Asn Thr Lys Val Asp Lys Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
```

His Glu Ala Leu His Asn His Tyr Thr Gln Lys Ser Leu Ser Leu Ser
    450                 455                 460

Pro Gly Lys
465

<210> SEQ ID NO 5
<211> LENGTH: 354
<212> TYPE: DNA
<213> ORGANISM: Artificial
<220> FEATURE:
<223> OTHER INFORMATION: murine CDR, human FR

<400> SEQUENCE: 5
caggttcagc tggtgcagtc tggagctgag gtgaagaagc ctggggcctc agtgaaggtc    60
tcctgcaagg cttctggtta ccctttacc aactatggaa tgaactgggt gcgacaggcc   120
cctggacaag ggcttgagtg gatgggatgg atcaacacct acactggaga gccaacatat   180
gctgatgcct tcaagggcag agtcaccatg accagagaca catccatcag cacagcctac   240
atggagctga gcaggctgag atctgacgac acggccgtgt attactgtgc gagagactac   300
ggcgactatg gtatggacta ctggggtcaa ggaaccaccg tcaccgtctc ctca          354

<210> SEQ ID NO 6
<211> LENGTH: 118
<212> TYPE: PRT
<213> ORGANISM: Artificial
<220> FEATURE:
<223> OTHER INFORMATION: murine CDR, human FR

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 7
<211> LENGTH: 1404
<212> TYPE: DNA
<213> ORGANISM: Artificial
<220> FEATURE:
<223> OTHER INFORMATION: murine CDR, human FR in HV Domain

<400> SEQUENCE: 7
atggcttggg tgtggaccct gctattcctg atggcagctg cccaaagtgc caagcacag     60 gttcagctgg tgcagtctgg agctgaggtg aagaagcctg gggcctcagt gaaggtctcc   120
tgcaaggctt ctggttacac ctttaccaac tatggaatga actgggtgcg acaggcccct   180
ggacaagggc ttgagtggat gggatggatc aacacctaca ctggagagcc aacatatgct   240

```
gatgccttca agggcagagt caccatgacc agagacacat ccatcagcac agcctacatg    300
gagctgagca ggctgagatc tgacgacacg gccgtgtatt actgtgcgag agactacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                           1404
```

<210> SEQ ID NO 8
<211> LENGTH: 467
<212> TYPE: PRT
<213> ORGANISM: Artificial
<220> FEATURE:
<223> OTHER INFORMATION: murine CDR, human FR in HV Domain

<400> SEQUENCE: 8

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
450                 455                 460

Pro Gly Lys
465

<210> SEQ ID NO 9
<211> LENGTH: 354
<212> TYPE: DNA
<213> ORGANISM: Artificial
<220> FEATURE:
<223> OTHER INFORMATION: murine CDR, murine residues in human FR

<400> SEQUENCE: 9
caggttcagc tggtgcagtc tggagctgag gtgaagaagc ctggggcctc agtgaaggtc    60
tcctgcaagg cttctggtta cacctttacc aactatggaa tgaactgggt gcgacaggcc   120
cctggacaag ggcttgagtg gatgggatgg atcaacacct acactggaga gccaacatat   180
gctgatgcct tcaagggcag atttgccttc tctttggaca catccacgag cacagcctac   240

```
ttgcagatca acagcctgag atctgacgac acggccgtgt attactgtgc gagagactac    300
ggcgactatg gtatggacta ctggggtcaa ggaaccaccg tcaccgtctc ctca          354
```

<210> SEQ ID NO 10
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Ala Phe
    50                  55                  60

Lys Gly Arg Phe Ala Phe Ser Leu Asp Thr Ser Thr Ser Thr Ala Tyr
65                  70                  75                  80

Leu Gln Ile Asn Ser Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115
```

<210> SEQ ID NO 11
<211> LENGTH: 1404
<212> TYPE: DNA
<213> ORGANISM: Artificial
<220> FEATURE:
<223> OTHER INFORMATION: murine CDR, murine residues in human FR

<400> SEQUENCE: 11

```
atggcttggg tgtggaccct gctattcctg atggcagctg cccaaagtgc caagcacag     60 gttcagctgg tgcagtctgg agctgaggtg aagaagcctg ggcctcagt gaaggtctcc    120 tgcaaggctt ctggttacac ctttaccaac tatggaatga actgggtgcg acaggccct    180 ggacaagggc ttgagtggat gggatggatc aacacctaca ctggagagcc aacatatgct    240
gatgccttca gggcagatt tgccttctct ttggacacat ccacgagcac agcctacttg    300
cagatcaaca gcctgagatc tgacgacacg gccgtgtatt actgtgcgag agactacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
```

```
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaaccatctc caaagccaaa     1080
gggcagcccc gagaaccaca ggtgtacacc ctgcccccat cccgggatga gctgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atga                                            1404
```

<210> SEQ ID NO 12
<211> LENGTH: 467
<212> TYPE: PRT
<213> ORGANISM: Artificial
<220> FEATURE:
<223> OTHER INFORMATION: murine CDR, murine residues in human FR

<400> SEQUENCE: 12

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Asp Thr Ser Thr Ser
                85                  90                  95

Thr Ala Tyr Leu Gln Ile Asn Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys
465
```

<210> SEQ ID NO 13
<211> LENGTH: 354
<212> TYPE: DNA
<213> ORGANISM: Artificial
<220> FEATURE:
<223> OTHER INFORMATION: murine CDR, murine residues in human FR

<400> SEQUENCE: 13

```
caggttcagc tggtgcagtc tggagctgag gtgaagaagc ctggggcctc agtgaaggtc    60
tcctgcaagg cttctggtta cacctttacc aactatggaa tgaactgggt gcgacaggcc   120
cctggacaag ggcttaagtg gatgggatgg atcaacacct acactggaga gccaacatat   180
gctgatgcct tcaagggcag agtcaccatg accagagaca tccatcagac acagcctac    240
atggagctga gcaggctgag atctgacgac acggccgtgt attactgtgc gagagactac   300
ggcgactatg gtatggacta ctggggtcaa ggaaccaccg tcaccgtctc ctca         354
```

<210> SEQ ID NO 14
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 14

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Lys Trp Met
        35                  40                  45
```

```
Gly Trp Ile Asn Thr Tyr Thr Gly Glu Pro Thr Tyr Ala Asp Ala Phe
    50                  55                  60
Lys Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp Tyr Gly Asp Tyr Gly Met Asp Tyr Trp Gly Gln Gly Thr
            100                 105                 110
Thr Val Thr Val Ser Ser
        115
```

<210> SEQ ID NO 15
<211> LENGTH: 1404
<212> TYPE: DNA
<213> ORGANISM: Artificial
<220> FEATURE:
<223> OTHER INFORMATION: murine CDR, murine residues in human FR

<400> SEQUENCE: 15

```
atggcttggg tgtggacctt gctattcctg atggcagctg cccaaagtgc ccaagcacag     60
gttcagctgg tgcagtctgg agctgaggtg aagaagcctg ggcctcagt gaaggtctcc    120
tgcaaggctt ctggttacac ctttaccaac tatggaatga actgggtgcg acaggcccct    180
ggacaagggc ttaagtggat gggatggatc aacacctaca ctggagagcc aacatatgct    240
gatgccttca agggcagagt caccatgacc agagacacat ccatcagcac agcctacatg    300
gagctgagca ggctgagatc tgacgacacg gccgtgtatt actgtgcgag actacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                         1404
```

<210> SEQ ID NO 16
<211> LENGTH: 467
<212> TYPE: PRT
<213> ORGANISM: Artificial

```
<220> FEATURE:
<223> OTHER INFORMATION: murine CDR, murine residues in human FR

<400> SEQUENCE: 16

Met Ala Trp Val Trp Thr Leu Leu Phe Leu Met Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 17
<211> LENGTH: 354
<212> TYPE: DNA
<213> ORGANISM: Artificial
<220> FEATURE:
<223> OTHER INFORMATION: murine CDR, murine residues in human FR

<400> SEQUENCE: 17
caggttcagc tggtgcagtc tggagctgag gtgaagaagc ctggggcctc agtgaaggtc      60
tcctgcaagg cttctggtta cacctttacc aactatggaa tgaactgggt gcgacaggcc     120
cctggacaag gcttaagtg atgggatgg atcaacacct acactggaga gccaacatat      180
gctgatgcct tcaagggcag atttgccttc tctttggaca catccacgag cacagcctac     240
atggagctga ggagcctgag atctgacgac acggccgtgt attactgtgc gagagactac     300
ggcgactatg gtatggacta ctggggtcaa ggaaccaccg tcaccgtctc ctca           354

<210> SEQ ID NO 18
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Tyr Ala Asp Ala Phe
    50                  55                  60

Lys Gly Arg Phe Ala Phe Ser Leu Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 19
<211> LENGTH: 1404
<212> TYPE: DNA
<213> ORGANISM: Artificial
<220> FEATURE:
<223> OTHER INFORMATION: murine CDR, murine residues in human FR
```

<400> SEQUENCE: 19

```
atggcttggg tgtggacctt gctattcctg atggcagctg cccaaagtgc ccaagcacag    60
gttcagctgg tgcagtctgg agctgaggtg aagaagcctg ggcctcagt gaaggtctcc    120
tgcaaggctt ctggttacac ctttaccaac tatggaatga actgggtgcg acaggcccct   180
ggacaagggc ttaagtggat gggatggatc aacacctaca ctggagagcc aacatatgct   240
gatgccttca agggcagatt tgccttctct ttggacacat ccacgagcac agcctacatg   300
gagctgagga gcctgagatc tgacgacacg gccgtgtatt actgtgcgag agactacggc   360
gactatggta tggactactg gggtcaagga accaccgtca ccgtctcctc agctagcacc   420
aagggcccat cggtcttccc cctggcaccc tcctccaaga gcacctctgg gggcacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaaga agttgagcc caaatcttgt    720
gacaaaactc acacatgccc accgtgccca gcacctgaac tcctggggg accgtcagtc    780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggatga gctgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctccctgt ctccgggtaa atga                                          1404
```

<210> SEQ ID NO 20
<211> LENGTH: 467
<212> TYPE: PRT
<213> ORGANISM: Artificial
<220> FEATURE:
<223> OTHER INFORMATION: murine CDR, murine residues in human FR

<400> SEQUENCE: 20

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Asp Thr Ser Thr Ser
                85                  90                  95
```

Thr Ala Tyr Met Glu Leu Arg Ser Leu Arg Ser Asp Asp Thr Ala Val
                100                 105                 110
Tyr Tyr Cys Ala Arg Asp Tyr Gly Asp Tyr Gly Met Asp Tyr Trp Gly
            115                 120                 125
Gln Gly Thr Thr Val Thr Val Ser Ser Ala Ser Thr Lys Gly Pro Ser
        130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys
465

<210> SEQ ID NO 21
<211> LENGTH: 396
<212> TYPE: DNA
<213> ORGANISM: Mus musculus

<400> SEQUENCE: 21

```
atggagacag acacactcct gttatgggta ctgctgctct gggttccagg ttccactggt    60
gacattgtgc tgacacagtc tcctgcttcc ttagctgtat ctctgggggca gagggccacc   120 atctcatgca gggccagcaa aagtgtcagt acatctggct atagtttat gcactggtat     180 caacagaaac caggacagcc acccaaactc ctcatctatc ttgcatccaa cctagaatct    240
ggggtccctg ccaggttcag tggcagtggg tctgggacag acttcaccct caacatccat    300
cctgtggagg aggaggatgc tgcaacctat tactgtcagc acagtaggga ggttccgtgg    360
acgttcggtg gaggcaccaa gctggaaatc aaacgg                              396
```

```
<210> SEQ ID NO 22
<211> LENGTH: 132
<212> TYPE: PRT
<213> ORGANISM: Mus musculus

<400> SEQUENCE: 22
```

```
Met Glu Thr Asp Thr Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Val Pro Trp Thr Phe Gly Gly Gly Thr Lys Leu
        115                 120                 125

Glu Ile Lys Arg
    130
```

```
<210> SEQ ID NO 23
<211> LENGTH: 336
<212> TYPE: DNA
<213> ORGANISM: Artificial
<220> FEATURE:
<223> OTHER INFORMATION: murine CDR, human FR

<400> SEQUENCE: 23
```

```
gacatcgtga tgacccagtc tccagactcc ctggctgtgt ctctgggcga gagggccacc    60
atcaactgca gggccagcaa aagtgtcagt acatctggct atagtttat gcactggtac    120 cagcagaaac caggacagcc tcctaagctg ctcatttacc ttgcatccaa cctagaatcc    180
ggggtccctg accgattcag tggcagcggg tctgggacag atttcactct caccatcagc    240
agcctgcagg ctgaagatgt ggcagtttat tactgtcagc acagtaggga ggttccgtgg    300
acgttcggtc aggcaccaa ggtggaaatc aaacgt                               336
```

```
<210> SEQ ID NO 24
<211> LENGTH: 112
<212> TYPE: PRT
<213> ORGANISM: Artificial
<220> FEATURE:
<223> OTHER INFORMATION: murine CDR, human FR
```

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
            100                 105                 110

<210> SEQ ID NO 25
<211> LENGTH: 717
<212> TYPE: DNA
<213> ORGANISM: Artificial
<220> FEATURE:
<223> OTHER INFORMATION: murine CDR, human FR

<400> SEQUENCE: 25
atggagacag acacactcct gttatgggta ctgctgctct gggttccagg ttccactggt     60
gacatcgtga tgacccagtc tccagactcc ctggctgtgt ctctgggcga gagggccacc    120
atcaactgca gggccagcaa aagtgtcagt acatctggct atagttttat gcactggtac    180
cagcagaaac caggacagcc tcctaagctg ctcatttacc ttgcatccaa cctagaatcc    240
ggggtccctg accgattcag tggcagcggg tctgggacag atttcactct caccatcagc    300
agcctgcagg ctgaagatgt ggcagtttat tactgtcagc acagtaggga ggttccgtgg    360
acgttcggtc agggcaccaa ggtggaaatc aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag acagcaagg acagcaccta cagcctcagc    600
agcaccctga cgctgagcaa agcagactac gagaaacaca agtctacgc ctgcgaagtc    660
acccatcagg gcctgagctc gcccgtcaca aagagcttca caggggaga gtgttag       717

<210> SEQ ID NO 26
<211> LENGTH: 238
<212> TYPE: PRT
<213> ORGANISM: Artificial
<220> FEATURE:
<223> OTHER INFORMATION: murine CDR, human FR

<400> SEQUENCE: 26

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Arg Glu Val Pro Trp Thr Phe Gly Gln Gly Thr Lys Val
            115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 27
<211> LENGTH: 411
<212> TYPE: DNA
<213> ORGANISM: Mus musculus

<400> SEQUENCE: 27
atggaatgga cctgggtctt tctcttcctc ctgccagtaa ctgcagatgt ccaatcccag      60
gttcagctgc aacagtctgg aactgagctg atgacgcctg gggcctcagt gacgatgtcc     120
tgcaagactt ctggctacac attcagtacc tactggatag agtgggtaaa acagaggcct     180
ggacatggcc ttgagtggat tggagaaatt ttacctggaa gtggttatac tgactacaat     240
gagaagttca aggccaaggc cacattcact gcagatacat cctccaacac agcctacatg     300
caactcagca gcctggcatc tgaggactct gccgtctatt actgtgcaag atgggatagg     360
ctctatgcta tggactactg gggtcaagga acctcagtca ccgtctcctc a              411

<210> SEQ ID NO 28
<211> LENGTH: 137
<212> TYPE: PRT
<213> ORGANISM: Mus musculus

<400> SEQUENCE: 28

Met Glu Trp Thr Trp Val Phe Leu Phe Leu Leu Ser Val Thr Ala Asp
1               5                   10                  15

Val Gln Ser Gln Val Gln Leu Gln Gln Ser Gly Thr Glu Leu Met Thr
            20                  25                  30

Pro Gly Ala Ser Val Thr Met Ser Cys Lys Thr Ser Gly Tyr Thr Phe
            35                  40                  45

Ser Thr Tyr Trp Ile Glu Trp Val Lys Gln Arg Pro Gly His Gly Leu
        50                  55                  60

Glu Trp Ile Gly Glu Ile Leu Gly Pro Ser Gly Tyr Thr Asp Tyr Asn
65                  70                  75                  80

Glu Lys Phe Lys Ala Lys Ala Thr Phe Thr Ala Asp Thr Ser Ser Asn
                85                  90                  95

Thr Ala Tyr Met Gln Leu Ser Ser Leu Ala Ser Glu Asp Ser Ala Val
            100                 105                 110

Tyr Tyr Cys Ala Arg Trp Asp Arg Leu Tyr Ala Met Asp Tyr Trp Gly
        115                 120                 125

Gly Gly Thr Ser Val Thr Val Ser Ser
    130                 135

<210> SEQ ID NO 29
<211> LENGTH: 396
<212> TYPE: DNA
<213> ORGANISM: Mus musculus

<400> SEQUENCE: 29
atggagacag acacactcct gttatgggta ctgctgctct gggttccagg ttccactggt      60
gacattgtgc tgacacagtc tcctgcttcc ttaactgtat ctctggggca gaagaccacc     120
atctcatgca gggccagcaa gagtgtcagt acatctggct atagttttat gcactggtac     180 caactgaaaac caggacagtc acccaaactc ctcatctatc ttgcgtccaa cctaccatct    240
ggggtccctg ccaggttcag tggcagtggg tctgggacag acttcaccct caaaatccat    300
cctgtggagg aggaggatgc tgcaacctat tactgtcagc acagtaggga gattccgtac    360
acgttcggag gggggaccaa gctggaaata cacgg                                396

<210> SEQ ID NO 30
<211> LENGTH: 132
<212> TYPE: PRT
<213> ORGANISM: Mus musculus

<400> SEQUENCE: 30

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Gln Lys Thr Thr Ile Ser Cys Arg Ala Ser Lys Ser
        35                  40                  45

Val Ser Thr Ser Gly Tyr Ser Phe Met His Trp Tyr Gln Leu Lys Pro
    50                  55                  60

Gly Gln Ser Pro Lys Leu Leu Ile Tyr Leu Ala Ser Asp Leu Pro Ser
65                  70                  75                  80

Gly Val Pro Ala Arg Phe Ser Gly Ser Gly Ser Gly Thr Asp Phe Thr
                85                  90                  95

Leu Lys Ile His Pro Val Glu Glu Glu Asp Ala Ala Thr Tyr Tyr Cys
            100                 105                 110

Gln His Ser Arg Glu Ile Pro Tyr Thr Phe Gly Gly Gly Thr Lys Leu
        115                 120                 125

Glu Ile Thr Arg
    130

<210> SEQ ID NO 31
<211> LENGTH: 330
<212> TYPE: PRT
<213> ORGANISM: Human

<400> SEQUENCE: 31

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 326
<212> TYPE: PRT
<213> ORGANISM: Human

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Thr Val Pro Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 33
<211> LENGTH: 290
<212> TYPE: PRT
<213> ORGANISM: Human

<400> SEQUENCE: 33

Gln Met Gln Gly Val Asn Cys Thr Val Ser Ser Glu Leu Lys Thr Pro
 1               5                  10                  15

Leu Gly Asp Thr Thr His Thr Cys Pro Arg Cys Pro Glu Pro Lys Ser
                20                  25                  30

Cys Asp Thr Pro Pro Pro Cys Pro Arg Cys Pro Glu Pro Lys Ser Cys
            35                  40                  45

Asp Thr Pro Pro Pro Cys Pro Arg Cys Pro Glu Pro Lys Ser Cys Asp
        50                  55                  60

Thr Pro Pro Pro Cys Pro Arg Cys Pro Ala Pro Glu Leu Leu Gly Gly
 65                  70                  75                  80

Pro Ser Val Phe Leu Phe Pro Pro Lys Pro Lys Asp Thr Leu Met Ile
                85                  90                  95
```

```
Ser Arg Thr Pro Glu Val Thr Cys Val Val Asp Val Ser His Glu
            100                 105                 110

Asp Pro Glu Val Gln Phe Lys Trp Tyr Val Asp Gly Val Gln Val His
            115                 120                 125

Asn Ala Lys Thr Lys Pro Arg Glu Gln Gln Phe Asn Ser Thr Phe Arg
130                 135                 140

Val Val Ser Val Leu Thr Val Leu His Gln Asn Trp Leu Asp Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Thr Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
210                 215                 220

Glu Ser Ser Gly Gln Pro Glu Asn Asn Tyr Asn Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
275                 280                 285

Gly Lys
290

<210> SEQ ID NO 34
<211> LENGTH: 327
<212> TYPE: PRT
<213> ORGANISM: Human

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 35
<211> LENGTH: 467
<212> TYPE: PRT
<213> ORGANISM: Artificial Sequence
<220> FEATURE:
<223> OTHER INFORMATION: Humanized antibody

<400> SEQUENCE: 35

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Asn Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

-continued

Pro Ser Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
450                 455                 460
Pro Gly Lys
465

<210> SEQ ID NO 36
<211> LENGTH: 463
<212> TYPE: PRT
<213> ORGANISM: Artificial Sequence
<220> FEATURE:
<223> OTHER INFORMATION: Humanized antibody

<400> SEQUENCE: 36

Met Ala Trp Val Trp Thr Leu Leu Phe Leu Met Ala Ala Ala Gln Ser
1               5                   10                  15
Ala Gln Ala Gln Val Gln Leu Val Gln Ser Gly Ala Glu Val Lys Lys
            20                  25                  30
Pro Gly Ala Ser Val Lys Val Ser Cys Lys Ala Ser Gly Tyr Thr Phe
        35                  40                  45
Thr Asn Tyr Gly Met Asn Trp Val Arg Gln Ala Pro Gly Gln Gly Leu
    50                  55                  60
Lys Trp Met Gly Trp Ile Asn Thr Tyr Thr Gly Asn Pro Thr Tyr Ala
65                  70                  75                  80
Asp Ala Phe Lys Gly Arg Val Thr Met Thr Arg Asp Thr Ser Ile Ser
                85                  90                  95

-continued

```
Thr Ala Tyr Met Glu Leu Ser Arg Leu Arg Ser Asp Thr Ala Val
                100                 105                 110
Tyr Tyr Cys Ala Arg Asp Tyr Gly Asp Tyr Gly Met Asp Tyr Trp Gly
            115                 120                 125
Gln Gly Thr Thr Val Thr Val Ser Ser Ala Ser Thr Lys Gly Pro Ser
130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Asn Phe Gly Thr Gln Thr Tyr Thr Cys Asn Val Asp His
210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Asp Val Ser His Glu Asp Pro Glu
        275                 280                 285
Val Gln Phe Asn Trp Tyr Val Asp Gly Val Glu Val His Asn Ala Lys
        290                 295                 300
Thr Lys Pro Arg Glu Glu Gln Phe Asn Ser Thr Phe Arg Val Val Ser
305                 310                 315                 320
Val Leu Thr Val Val His Gln Asp Trp Leu Asn Gly Lys Glu Tyr Lys
                325                 330                 335
Cys Lys Val Ser Asn Lys Gly Leu Pro Ala Pro Ile Glu Lys Thr Ile
            340                 345                 350
Ser Lys Thr Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Met Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
450                 455                 460
```

<210> SEQ ID NO 37
<211> LENGTH: 464
<212> TYPE: PRT
<213> ORGANISM: Artificial Sequence
<220> FEATURE:
<223> OTHER INFORMATION: Humanized antibody

<400> SEQUENCE: 37

```
Met Ala Trp Val Trp Thr Leu Leu Phe Leu Met Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
        50                  55                  60

Lys Trp Met Gly Trp Ile Asn Thr Tyr Thr Gly Asn Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Ser Cys Pro Ala Pro Glu Phe Leu Gly Gly Pro Ser
            245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
        340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415
```

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
    435                 440                 445

Leu His Asn His Tyr Thr Gln Lys Ser Leu Ser Leu Ser Leu Gly Lys
        450                 455                 460

<210> SEQ ID NO 38
<211> LENGTH: 467
<212> TYPE: PRT
<213> ORGANISM: Artificial Sequence
<220> FEATURE:
<223> OTHER INFORMATION: Humanized antibody

<400> SEQUENCE: 38

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Asn Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Pro Val Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

```
Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 39
<211> LENGTH: 464
<212> TYPE: PRT
<213> ORGANISM: Artificial Sequence
<220> FEATURE:
<223> OTHER INFORMATION: Humanized antibody

<400> SEQUENCE: 39

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Asn Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

-continued

```
Pro Ser Ser Leu Gly Thr Lys Thr Tyr Thr Cys Asn Val Asp His
    210             215             220

Lys Pro Ser Asn Thr Lys Val Asp Lys Arg Val Glu Ser Lys Tyr Gly
225             230             235             240

Pro Pro Cys Pro Pro Cys Pro Ala Pro Glu Phe Ala Gly Ala Pro Ser
            245             250             255

Val Phe Leu Phe Pro Pro Lys Pro Lys Asp Thr Leu Met Ile Ser Arg
            260             265             270

Thr Pro Glu Val Thr Cys Val Val Asp Val Ser Gln Glu Asp Pro
            275             280             285

Glu Val Gln Phe Asn Trp Tyr Val Asp Gly Val Glu Val His Asn Ala
    290             295             300

Lys Thr Lys Pro Arg Glu Glu Gln Phe Asn Ser Thr Tyr Arg Val Val
305             310             315             320

Ser Val Leu Thr Val Leu His Gln Asp Trp Leu Asn Gly Lys Ala Tyr
            325             330             335

Lys Cys Lys Val Ser Asn Lys Gly Leu Pro Ser Ser Ile Glu Lys Thr
            340             345             350

Ile Ser Lys Ala Lys Gly Gln Pro Arg Glu Pro Gln Val Tyr Thr Leu
    355             360             365

Pro Pro Ser Gln Glu Glu Met Thr Lys Asn Gln Val Ser Leu Thr Cys
    370             375             380

Leu Val Lys Gly Phe Tyr Pro Ser Asp Ile Ala Val Glu Trp Glu Ser
385             390             395             400

Asn Gly Gln Pro Glu Asn Asn Tyr Lys Thr Thr Pro Pro Val Leu Asp
            405             410             415

Ser Asp Gly Ser Phe Phe Leu Tyr Ser Arg Leu Thr Val Asp Lys Ser
            420             425             430

Arg Trp Gln Glu Gly Asn Val Phe Ser Cys Ser Val Met His Glu Ala
    435             440             445

Leu His Asn His Tyr Thr Gln Lys Ser Leu Ser Leu Ser Leu Gly Lys
    450             455             460
```

US 9,061,074 B2

VARIANT TARGET BINDING AGENTS AND USES THEREOF

CONTINUITY

This application is a continuation application of U.S. application Ser. No. 12/516,914, which is the national stage filing under 35 U.S.C. 371 of International Application No. PCT/US2007/086205 filed Dec. 1, 2007 and published Jun. 12, 2008 as International Publication No. WO 08/070,593, which, in turn, claims the benefit of U.S. Provisional Application No. 60/872,239, filed Dec. 1, 2006 and U.S. Provisional Application No. 60/918,563, filed Mar. 16, 2007; all of which are incorporated by reference herein in their entireties.

BACKGROUND OF THE INVENTION

Antibody conjugation to cytotoxic drugs is one of the most promising ways to enhance the therapeutic activity of antibodies and reduce the systemic toxicity of drugs. At least six antibody drug conjugates (ADCs) have progressed into clinical development. One feature of antibodies that potentially limits the therapeutic index (i.e., maximum tolerated dose/minimum curative dose) of an ADC is non-target toxicity. Such specificity may be specific or non-specific. Non-target uptake of ADCs may lead to ADC catabolism, drug release and/or toxicity.

Accordingly, there is a need for ADCs and other target binding agents that can exert a clinically useful cytotoxic, cytostatic, or immunomodulatory effect on target cells, particularly without exerting undesirable effects on non-target cells. Such ADCs and other target binding agents would be useful therapeutic agents against cancers that express a target antigen or immune disorders that are express target antigens. The present invention satisfies this and other needs. (The recitation of any reference in this application is not an admission that the reference is prior art to this application).

BRIEF SUMMARY OF THE INVENTION

The present invention provides variant antibody drug conjugates (ADCs) and related variant target binding agents and methods relating to the use of such ADCs and binding agents for the prophylaxis or treatment of cancers and immunological disorders. The variant ADCs and related variant target binding agents, alone or in combination with a therapeutic agent, exert a cytotoxic, cytostatic, or immunomodulatory effect on target cells.

In one aspect, variant target binding agents are provided. The variant target binding agent specifically binds to a target antigen and includes at least one CDR or variable region of an antibody. In some embodiments, the variant target binding agent is an antibody. In some embodiments, the variant target binding agent includes at least one modification (e.g., an amino acid substitution, addition, or deletion) in or in proximity to a domain (e.g., a region of an Fc, also referred to as an Fc region) mediating binding to one or more Fcγ receptors, resulting in impaired binding to the one or more Fcγ receptors. The variant target binding agent may exhibit reduced ADCC, ADCP and/or CDC responses. In some embodiments, the at least one modification is a replacement of an amino acid residue involved in the binding interaction of the Fc region to one or more Fcγ receptors with a non-conservative amino acid. In some embodiments, the at least one modification is the replacement of an amino acid residue involved in the binding interaction of the Fc region to one or more Fcγ receptors with cysteine. In some embodiments, the at least one modification is the replacement of three contiguous amino acid residues involved in the binding interaction of the Fc region to one or more Fcγ receptors with asparagine-any amino acid (X)-serine or asparagine-X-threonine, wherein X is not proline. In some embodiments, the variant target binding agent exerts a cytotoxic, cytostatic or immunomodulatory effect in the absence of conjugation to a therapeutic agent. In some embodiments, the variant target binding agent is conjugated to a therapeutic agent which exerts a cytotoxic, cytostatic or immunomodulatory effect.

In another aspect, a method of treating a cancer expressing a target antigen in a subject is provided. The method generally includes administering to the subject an effective amount of a variant target binding agent. The variant target binding agent specifically binds to a target antigen and includes at least one CDR or variable region of an antibody. In some embodiments, the variant target binding agent is an antibody. In some embodiments, the variant target binding agent includes at least one modification (e.g., an amino acid substitution, addition, or deletion) in or in proximity to a domain (e.g., an Fc region) involved in the binding interaction of the Fc region to one or more Fcγ receptors, resulting in impaired binding to one or more Fcγ receptors. The variant target binding agent may exhibit reduced ADCC, ADCP and/or CDC responses. In some embodiments, the at least one modification is the replacement of an amino acid residue involved in the binding interaction of the Fc region to one or more Fcγ receptors with a non-conservative amino acid. In some embodiments, the at least one modification is the replacement of an amino acid residue involved in the binding interaction of the Fc region to one or more Fcγ receptors with cysteine. In some embodiments, the at least one modification is the replacement of three contiguous amino acid residues involved in the binding interaction of the Fc region to one or more Fcγ receptors with asparagine-X-serine or asparagine-X-threonine, wherein X is not proline. In some embodiments, the variant target binding agent exerts a cytotoxic, cytostatic or immunomodulatory effect in the absence of conjugation to a therapeutic agent. In some embodiments, the variant target binding agent is conjugated to a therapeutic agent which exerts a cytotoxic, cytostatic or immunomodulatory effect.

In some embodiments, the amino acid substitution affects the binding interaction of the Fc region with the FcγRIIIa receptor. In some embodiments, the amino acid substitution of the native amino acid to a cysteine residue is introduced at amino acid position 239, 265, 269 or 327. In some embodiments, the amino acid substitution of the native amino acid to a cysteine residue is introduced at amino acid position 239 or 269. In some embodiments, the amino acid substitution of the native amino acid to a cysteine residue is introduced at amino acid position 239. In other embodiments, the amino acid substitution of the native amino acid to a cysteine residue is introduced at amino acid position 236 or 238.

In other embodiments, the amino acid substitution of the native amino acid to a cysteine residue is introduced at amino acid position 234, 235, 237, 267, 298, 299, 326, 330, or 332. In other embodiments, the amino acid substitution of the native amino acid to a cysteine residue is introduced at amino acid position 237, 298, 299, 326, 330, or 332. In other embodiments, the amino acid substitution of the native amino acid to a cysteine residue is introduced at amino acid position 298, 299, 326 or 330.

The variant target binding agent can be, for example, an antibody. The antibody can include, for example, a constant domain of a human IgM or IgG antibody. The IgG antibody can be, for example, a human IgG1, IgG2, IgG3 or IgG4 subtype. In some embodiments, the antibody includes a human constant region. In some embodiments, the target binding agent (e.g., antibody) specifically binds to CD20, CD30, CD33, CD70 or CD133. In some embodiments, the variant antibody competes for binding to CD70 with monoclonal antibody 1F6 or 2F2. In other embodiments, the antibody is a variant humanized 1F6 antibody. The antibody can be, for example, monovalent, divalent or multivalent.

The cancer can be, for example, a kidney tumor, a B cell lymphoma, a colon carcinoma, Hodgkin's Disease, multiple myeloma, Waldenström's macroglobulinemia, non-Hodgkin's lymphoma, a mantle cell lymphoma, chronic lymphocytic leukemia, acute lymphocytic leukemia, a nasopharyngeal carcinoma, brain tumor, or a thymic carcinoma. The kidney tumor can be, for example, a renal cell carcinoma. The brain tumor can be, for example, a glioma, a glioblastoma, an astrocytoma, or a meningioma. The subject can be, for example, a mammal, such as a human being.

In another aspect, a method for treating an immunological disorder is provided. The method includes administering to a subject an effective amount of a variant target binding agent. The variant target binding agent specifically binds to a target antigen on an immune cell and includes at least one CDR or variable region of an antibody. In some embodiments, the variant target binding agent is an antibody. In some embodiments, the variant target binding agent includes at least one modification (e.g., an amino acid substitution, addition, or deletion) in or in proximity to a domain (e.g., an Fc region) involved in the binding interaction of the Fc region to one or more Fcγ receptors, resulting in impaired binding to one or more Fcγ receptors. The variant target binding agent may exhibit reduced ADCC, ADCP and/or CDC responses in the subject. In some embodiments, the at least one modification is the replacement of an amino acid residue involved in the binding interaction of the Fc region to one or more Fcγ receptors with a non-conservative amino acid. In some embodiments, the at least one modification is the replacement of an amino acid residue involved in the binding interaction of the Fc region to one or more Fcγ receptors with cysteine. In some embodiments, the at least one modification is the replacement of three contiguous amino acid residues involved in the binding interaction of the Fc region to one or more Fcγ receptors with asparagine-X-serine or asparagine-X-threonine, wherein X is not proline.

The variant target binding agent can be, for example, an antibody. The antibody can include, for example, an effector domain of a human IgM or IgG antibody. The IgG antibody can be, for example, a human IgG1, IgG2, IgG3 or IgG4 subtype. In some embodiments, the antibody includes a human constant region. In some embodiments, the target binding agent (e.g., antibody) specifically binds to CD19, CD20, CD30 or CD70. In some embodiments, the variant target binding agent competes for binding to CD70 with monoclonal antibody 1F6 or 2F2. In other embodiments, the antibody is a variant humanized 1F6 antibody. The antibody can be, for example, monovalent, divalent or multivalent.

The immunological disorder can be, for example, a T cell-mediated immunological disorder. In some embodiments, the T cell-mediated immunological disorder comprises activated T cells. In some embodiments, the activated T cells express CD70. In some embodiments, resting T cells are not substantially depleted by administration of the variant target binding agent. The T cell-mediated immunological disorder also can be, for example, rheumatoid arthritis, psoriatic arthritis, systemic lupus erythematosus (SLE), Type I diabetes, asthma, atopic dermatitis, allergic rhinitis, thrombocytopenic purpura, multiple sclerosis, psoriasis, Sjögren's syndrome, Hashimoto's thyroiditis, Graves' disease, primary biliary cirrhosis, Wegener's granulomatosis, tuberculosis, or graft versus host disease. In other embodiments, the immunological disorder is an activated B-lymphocyte disorder. The subject can be, for example, a mammal, such as a human being.

In a related aspect, also provided is a pharmaceutical composition for the treatment of a cancer or an immunological disorder. The pharmaceutical composition includes a variant target binding agent or pharmaceutically acceptable salt thereof and at least one pharmaceutically compatible ingredient. Further provided is a pharmaceutical kit including a first container comprising a variant target binding agent, wherein the agent is lyophilized, and a second container comprising a pharmaceutically acceptable diluent.

The present invention may be more fully understood by reference to the following detailed description of the invention, non-limiting examples of specific embodiments of the invention and the appended figures and sequence listing.

BRIEF DESCRIPTION OF THE DRAWINGS

FIG. 2 shows the amino acid sequences of the human constant domains of the (A) IgG1 (SEQ ID NO:31), (B) IgG2 (SEQ ID NO:32), (C) IgG3 (SEQ ID NO:33) and (D) IgG4 (SEQ ID NO:34) isotypes.

FIG. 3 shows the amino acid sequences of the (A) IgG1 (SEQ ID NO:35), (B) IgG2 (SEQ ID NO:36) and (C) IgG4 (SEQ ID NO:37) isotype variants of the humanized 1F6 antibody derivative HJLA. The amino acid sequence of h1F6 IgG1 is the same as SEQ ID NO:16.

FIG. 4 shows the amino acid sequences of the (A) IgG1v1 (SEQ ID NO:38) and (B) IgG4v3 (SEQ ID NO:39) Fc domain variants of the humanized 1F6 antibody derivative HJLA. (A) h1F6 IgG1v1 differs from h1F6 IgG1 by three amino acid substitutions: E233P, L234V and L235A (EU index, as set forth in Kabat), which correspond to amino acids 253-255, respectively (underlined in figure). (B) 1F6 IgG4v3 differs from h1F6 IgG4 by four amino acid substitutions: S228P, L235A, G237A and E318A (EU index, as set forth in Kabat), which correspond to amino acids 245, 252, 254 and 335, respectively (underlined in figure).

DETAILED DESCRIPTION OF THE INVENTION

Figure 1:
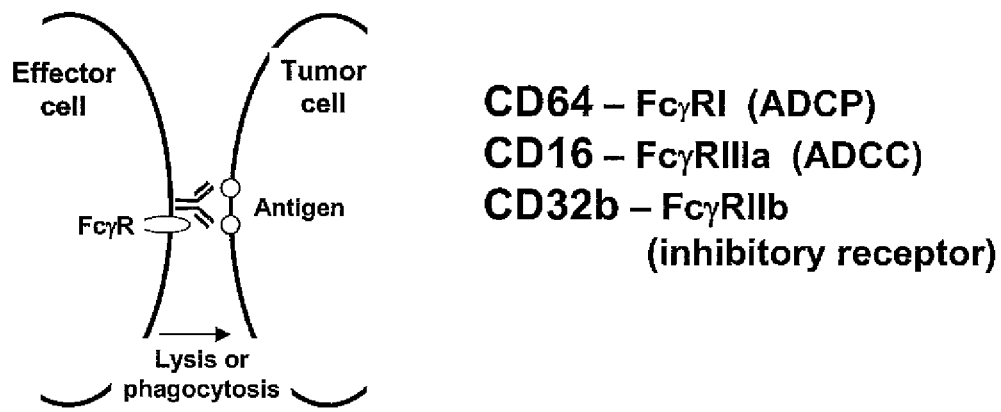
FIG. 1 is a schematic diagram depicting the antibody-mediated interaction between effector cells and target cells (e.g., tumor cells). Effector cells bearing Fc gamma (Fcγ) receptors, either FcγRI (CD64), FcγRIIb (CD32b) or FcγRIIIa (CD16), are brought in close proximity to tumor cells via binding the Fc domain of antibodies that bind to antigens on the surface of the tumor cell. FcγRI induces ADCC activity, FcγRIIb induces inhibitory activity, and FcγRIIIa induces ADCP activity, in the antibody-targeted tumor cells. FcγRI, FcγRIIb and FcγRIIIa are expressed on a variety of normal tissues, leukocytes, all myeloid-derived cells, endothelial cells and some epithelial cells.

The present invention provides variant target binding agents and methods for using such binding agents for the prophylaxis or treatment of cancers and immunological disorders. The variant target binding agents include a binding region that specifically binds to a target antigen (e.g., the extracellular domain of the target molecule). In some aspects, the variant target binding agent comprises a binding region comprising an antibody Fv region or an antigen binding fragment thereof that specifically binds to a target antigen. The variant target binding agents include at least one modification (e.g., amino acid substitution, addition, or deletion) in or in the proximity of a domain (e.g., an Fc region) involved in the binding interaction of the Fc region to one or more Fc receptors, resulting in impaired binding to a Fcγ receptor(s) (typically a human Fcγ receptor). Surprisingly, variant target binding agents with impaired binding to a Fcγ receptor(s) exhibit increased potency against target cells, as compared to the comparable unmodified binding agent. The variant target binding agent may also provide increased exposure in vivo, as compared to the unmodified binding agent (e.g., increased AUC). It is also contemplated that such variant target binding agents will exhibit reduced non-target toxicity, as compared with their non-variant parents. The variant target binding agent typically has reduced or absent ADCC, ADCP and/or CDC function. The variant target binding agent can exert a cytostatic, cytotoxic or immunomodulatory effect.

In one aspect, the compositions and methods relate to variant target binding agents, such as antibodies and antibody derivatives. The variant target binding agents include an antibody constant region or domain. The antibody constant region or domain can be, for example, of the IgG subtype. The antibody constant region or domain has a domain (e.g., an Fc region) that can interact with effector cells or complement to mediate a cytotoxic, cytostatic, or immunomodulatory effect resulting in the depletion or inhibition of the proliferation of target-expressing cells. In an exemplary embodiment, the Fc region has at least one modification (e.g., amino acid substitution, addition, or deletion) such that binding to one or more one or more Fcγ receptors is impaired and one or more effector functions (e.g., ADCC, ADCP and/or CDC response) are reduced. In an embodiment, the at least one modification is the replacement of an amino acid residue involved in the binding interaction of the Fc region to one or more Fcγ receptors with a non-conservative amino acid. In an embodiment, the at least one modification is the replacement of an amino acid residue involved in the binding interaction of the Fc region to one or more Fcγ receptors with cysteine. In an embodiment, the at least one modification is the replacement of three contiguous amino acid residues involved in the binding interaction of the Fc region to one or more Fcγ receptors with asparagine-X-serine or asparagine-X-threonine, wherein X is not proline. The variant target binding agent can be a monoclonal, chimeric or humanized antibody, or a fragment or derivative thereof. In an exemplary embodiment, the variant antibody, fragment or derivative thereof, competes with the murine monoclonal antibody (mAb) 1F6 or 2F2 for binding to CD70 and comprises human antibody constant region sequences.

In some embodiments, the amino acid substitution affects the binding interaction of the Fc region with the FcγRIIIa receptor. In some embodiments, the amino acid substitution of the native amino acid to a cysteine residue is introduced at amino acid position 239, 265, 269 or 327. In some embodiments, the amino acid substitution of the native amino acid to a cysteine residue is introduced at amino acid position 239 or 269. In some embodiments, the amino acid substitution of the native amino acid to a cysteine residue is introduced at amino acid position 239. In other embodiments, the amino acid substitution of the native amino acid to a cysteine residue is introduced at amino acid position 236 or 238.

In other embodiments, the amino acid substitution of the native amino acid to a cysteine residue is introduced at amino acid position 234, 235, 237, 267, 298, 299, 326, 330, or 332. In other embodiments, the amino acid substitution of the native amino acid to a cysteine residue is introduced at amino acid position 237, 298, 299, 326, 330, or 332. In other embodiments, the amino acid substitution of the native amino acid to a cysteine residue is introduced at amino acid position 298, 299, 326 or 330

In an exemplary embodiment, the variant target binding agent has reduced binding or uptake by non-target cells. For example, the binding or uptake by non-target cells can be reduced by at least 10%, at least 20%, at least 30%, at least 40%, at least 50%, at least 60%, at least 70%, at least 80% or at least 90%, as compared with a non-variant targeting binding agent. In another exemplary embodiment, the variant target binding agent exhibits reduced binding to one or more Fcγ receptors, but retains the ability to bind to FcRn receptors. In an exemplary embodiment, the variant target binding agent exerts a cytotoxic, cytostatic or immunomodulatory effect.

In some embodiments, the blood serum level of the variant target binding agent is increased, relative to a non-variant target binding agent. For example, blood serum level of the variant target binding agent can be increased by at least 10%, at least 20%, at least 30%, at least 40%, at least 50%, at least 60%, at least 70%, at least 80% or at least 90%, relative to a non-variant target binding agent.

In some embodiments, the blood serum half-life of the variant target binding agent in increased, relative to a non-variant target binding agent. For example, blood serum half-life of the variant target binding agent can be increased by at least 10%, at least 20%, at least 30%, at least 40%, at least 50%, at least 60%, at least 70%, at least 80% or at least 90%, relative to a non-variant target binding agent.

In some embodiments, the potency of the variant target binding agent in increased, relative to a non-variant target binding agent. For example, potency of the variant target binding agent can be increased by at least 10%, at least 20%, at least 30%, at least 40%, at least 50%, at least 60%, at least 70%, at least 80% or at least 90%, relative to a non-variant target binding agent.

Also included are pharmaceutical compositions comprising a variant target binding agent and a pharmaceutically compatible ingredient (e.g., carrier or excipient).

Also included are kits and articles of manufacture comprising a variant target binding agent.

For clarity of disclosure, and not by way of limitation, the detailed description of the invention is divided into the subsections which follow.

I. Definitions and Abbreviations

Unless defined otherwise, all technical and scientific terms used herein have the same meaning as commonly understood by one of ordinary skill in the art pertinent to the methods and compositions described. When trade names are used herein, applicants intend to independently include the trade name product formulation, the generic drug, and the active pharmaceutical ingredient(s) of the trade name product. As used herein, the following terms and phrases have the meanings ascribed to them unless specified otherwise.

The terms "target binding agent" and "anti-target binding agent" as used herein means an antibody, or a derivative or a fragment of an antibody, or other agent that binds to a target antigen and comprises at least a portion of an Fc region. The term "target binding agent" also includes an antibody, or a derivative or a fragment of an antibody, or other agent that binds to a target antigen and comprises at least a portion of a Fc region conjugated to a therapeutic agent which exerts a cytotoxic, cytostatic or immunomodulatory effect. In some embodiments, the target binding agent further comprises at least one CDR or variable region of an antibody, or a derivative thereof, that binds to the target antigen. The term "target binding agent" includes "variant target binding agent" defined infra.

The term "antibody drug conjugate" or "ADC" as used herein means an antibody, or a derivative or a fragment of an antibody, or other agent that binds to a target antigen and comprises at least a portion of an Fc region conjugated to a therapeutic agent which exerts a cytotoxic, cytostatic or immunomodulatory effect.

The term "variant" as used herein means a target binding agent, such as an antibody, or a derivative or a fragment of a target binding agent, which includes at least one modification (e.g., amino acid substitution, addition, or deletion) in a domain (e.g., an Fc region) involved in the binding interaction of the Fc region to one or more Fcγ receptors, resulting in impaired binding to one or more Fcγ receptors. The variant target binding agent may exhibit reduced or absent ADCC, ADCP and/or CDC responses. A "variant" also includes a target binding agent, or a derivative or a fragment of a target binding agent, which includes a domain (e.g., an Fc region) from a constant domain of an IgG isotype other than IgG1 (e.g., IgG2, IgG3, or IgG4).

The term "Fc region" or "Fc domain" refers to the region(s) of an antibody constant region (e.g., IgG1, IgG2, IgG3, or IgG4) that is involved in the binding interaction of the Fc region to one or more Fcγ receptors (e.g., FcγRI (CD64), FcγRIIb (CD32b) or FcγRIIIa (CD16). The locations of the regions or domains of IgG isotype constant regions are known in the art and are described, for example, in Shields et al., 2001, *J. Biol. Chem.* 276:6591-6604, and Canfield and Morrison, 1991, *J. Exp. Med.* 173:1483-1491 and Sondermann et al., 2000, *Nature* 406(6793): 267-73. The Fc regions or domains include, for example and not for limitation, the hinge region and the $C_H2$ domain.

The term "impaired binding to one or more Fcγ receptors" or impaired binding to an Fcγ receptor" refers to the reduced ability of a variant target binding agent to bind to an Fcγ receptor, as compared with a non-variant target binding agent. In some embodiments, the binding of the variant target binding agent to an Fcγ receptor is reduced by at least 10%, at least 20%, at least 30%, at least 40%, at least 50%, at least 60%, at least 70%, at least 80% or at least 90%, relative to a non-variant target binding agent.

The terms "specifically binds" and "specifically binding" means that the binding agent will react, in a highly selective manner, with its corresponding antigen (e.g., CD70), and not with the multitude of other antigens (e.g., non-CD70 molecules).

As used herein, the term "functional" in the context of a target binding agent indicates that the binding agent is capable of specifically binding to a target antigen.

The terms "inhibit" and "inhibition of" as used herein means to reduce by a measurable amount, or to prevent entirely.

The term "deplete" in the context of the effect of a target binding agent on target expressing cells refers to a reduction in the number of or elimination of the target expressing cells.

"Intact antibodies" and "intact immunoglobulins" are defined herein as heterotetrameric glycoproteins, typically of about 150,000 Daltons, composed of two identical light (L) chain and two identical heavy (H) chains. Each light chain is covalently linked to a heavy chain by a disulfide bond to form a heterodimer. The heterotetramer is formed by covalent disulfide linkage between the two identical heavy chains of such heterodimers. Although the light and heavy chains are linked together by a disulfide bond, the number of disulfide linkages between the two heavy chains varies by immunoglobulin (Ig) isotype. Each heavy and light chain also has regularly spaced intrachain disulfide bridges. Each heavy chain has at the amino-terminus a variable domain ($V_H$), followed by three or four constant domains ($C_H1$, $C_H2$, $C_H3$, and/or $C_H4$), as well as a hinge (J) region between $C_H1$ and $C_H2$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (Chothia et al., 1985, *J. Mol. Biol.* 186:651-663).

The term "hypervariable" refers to certain sequences within the variable domains that differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th ed. Public Health Service, National Institutes of Health, Bethesda, M.D., whereas HVLs are structurally defined according to the three-dimensional structure of the variable domain, as described by Chothia and Lesk, 1987, *J. Mol. Biol.* 196:901-917. Where these two methods result in slightly different identifications of a CDR, the structural definition is preferred. As defined by Kabat (see Kabat et al., "Sequences of proteins of immunological interest, 5th ed., Pub. No. 91-3242, U.S. Dept. Health & Human Services, NIH, Bethesda, M.D., 1991), CDR-L1 is positioned at about residues 24-34, CDR-L2, at about residues 50-56, and CDR-L3, at about residues and 89-97 in the light chain variable domain and at about 31-35 in CDR-H1, at about 50-65 in CDR-H2, and at about 95-102 in CDR-H3 in the heavy chain variable domain.

The three CDRs within each of the heavy and light chains are separated by framework regions (FRs), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen-binding site (see Kabat et al., 1991, NIH Publ. No. 91-3242, Vol. I, pages 647-669), although not all CDR residues are necessarily directly involved in antigen-binding.

FR residues and Ig constant domains typically are not directly involved in antigen-binding, but can contribute to antigen-binding or mediate antibody effector function. Some FR residues can have a significant effect on antigen-binding in at least three ways: 1) by noncovalently binding directly to an epitope; 2) by interacting with one or more CDR residues, and 3) by affecting the interface between the heavy and light chains. The constant domains mediate various Ig effector functions, such as participation of the antibody in antibody dependent cellular cytotoxicity (ADCC), complement dependent cytotoxicity (CDC) and/or antibody dependent cellular phagocytosis (ADCP).

The light chains of vertebrate immunoglobulins are assigned to one of two clearly distinct classes, kappa (k) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., IgG1, IgG2, IgG3, IgG4, IgA, and IgA2. The heavy chain constant domains that correspond to the different classes of immunoglobulins are called α, δ, ε, γ, and μ, respectively. The subunit structures and three-dimensional configurations of the classes of native immunoglobulins are well known.

The term "antibody" is used herein in the broadest sense and specifically encompasses full-length and native antibodies, monoclonal antibodies (including full-length monoclonal antibodies), polyclonal antibodies, multispecific antibodies (e.g., bispecific antibodies), and antibody or antigen-binding fragments thereof, such as variable domains and other portions of antibodies that exhibit a desired biological activity, e.g., binding to a target antigen.

The term "monoclonal antibody" (mAb) refers to an antibody obtained from a population of substantially homogeneous antibodies; i.e., the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Köhler et al., 1975, Nature 256:495, or recombinant DNA methods known in the art (see, e.g., U.S. Pat. No. 4,816,567). In another example, monoclonal antibodies can also be isolated from phage antibody libraries, using techniques described in Clackson et al., 1991, Nature 352: 624-628, and Marks et al., 1991, J. Mol. Biol. 222:581-597.

In contrast, the antibodies in a preparation of polyclonal antibodies are typically a heterogeneous population of immunoglobulin isotypes and/or classes and also exhibit a variety of epitope specificity.

The term "chimeric" antibody, as used herein, is a type of monoclonal antibody in which a portion of or the complete amino acid sequence in one or more regions or domains of the heavy and/or light chain is identical with, homologous to, or a derivative of the corresponding sequence in a monoclonal antibody from another species or belonging to another immunoglobulin class or isotype, or from a consensus sequence. Chimeric antibodies include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad Sci. USA 81:6851-6855). Methods for producing chimeric antibodies are known in the art. (See, e.g., Morrison, 1985. Science 229:1202; Oi et al., 1986, BioTechniques 4:214; Gillies et al., 1989, J. Immunol. Methods 125:191-202; U.S. Pat. Nos. 5,807,715; 4,816, 567; and 4,816,397.)

The terms "antibody fragment" refers to a portion of a full-length antibody in which a variable region or a functional capability is retained, for example, specific epitope binding. Examples of antibody fragments include, but are not limited to, a Fab, Fab', F(ab')₂, Fd, Fv, scFv and scFv-Fc fragment, diabody, triabody, tetrabody, linear antibody, single-chain antibody, and other multispecific antibodies formed from antibody fragments. (See Holliger and Hudson, 2005, Nat. Biotechnol. 23:1126-1136.)

A "single-chain Fv" or "scFv" antibody fragment is a single chain Fv derivative comprising the $V_H$ and $V_L$ domains of an antibody, in which the domains are present in a single polypeptide chain and which is capable of recognizing and binding antigen. The scFv polypeptide optionally contains a polypeptide linker positioned between the $V_H$ and $V_L$ domains which enables the scFv to form a desired three-dimensional structure for antigen-binding. (See, e.g., Pluckthun, 1994, In The Pharmacology of Monoclonal Antibodies, Vol. 113, Rosenburg and Moore eds., Springer-Verlag, New York, pp. 269-315).

The term "diabody" refers to small antibody fragment having two antigen-binding sites. Each fragment contains a heavy chain variable domain ($V_H$) concatenated to a light chain variable domain ($V_L$) to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 404097; WO 93/11161; and Hollinger et al., 1993, Proc. Natl. Acad. Sci. USA 90:6444-6448.

The term "linear antibody" refers to antibodies that comprises a pair of tandem Fd segments ($V_H$-$C_H$1-$V_H$-$C_H$1) that form a pair of antigen-binding regions. Linear antibodies can be bispecific or monospecific, as described in Zapata et al., 1995, Protein Eng. 8(10):1057-1062.

A "humanized antibody" refers to an immunoglobulin amino acid sequence derivative or fragment thereof which is capable of binding to a predetermined antigen and which comprises a variable region polypeptide chain having framework regions having substantially the amino acid sequence of a human immunoglobulin and a CDR(s) having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and typically two, variable domains in which all or substantially all of the CDR regions correspond to those of a non-human immunoglobulin and all or substantially all of the framework regions are those of a human immunoglobulin sequence, such as from, for example, a consensus or germline sequence. The humanized antibody optionally also will comprise at least a portion of an immunoglobulin Fc domain, typically that of a human immunoglobulin. For example, the antibody may contain both the light chain as well as at least the variable domain of a heavy chain. The antibody also may include the $C_H1$, hinge (J), $C_H2$, $C_H3$, and/or $C_H4$ regions of the heavy chain, as appropriate.

The humanized antibody can be selected from any class of immunoglobulins, including IgM, IgG, IgD, IgA and IgE, and any isotype, including IgG1, IgG2, IgG3 and IgG4. The constant region or domain can include, for example, a complement fixing constant domain where it is desired that the humanized antibody exhibit cytotoxic activity (e.g., IgG1). Where such cytotoxic activity is not desirable, the constant domain may be of another class (e.g., IgG2). The humanized antibody may comprise sequences from more than one class or isotype, and selecting particular constant domains to optimize desired effector functions is within the ordinary skill in the art.

The FR and CDR regions of the humanized antibody need not correspond precisely to the parental sequences, e.g., the import CDR or the consensus FR may be altered by substitution, insertion or deletion of at least one residue so that the CDR or FR residue at that site does not correspond to either the consensus or the import antibody. Such mutations typically will not be extensive. Usually, at least 75% of the humanized antibody residues will correspond to those of the parental FR and CDR sequences, more often at least 90%, and most often greater than 95%.

"Immune cell" as used herein refers to a cell of hematopoietic lineage involved in regulating an immune response. In typical embodiments, an immune cell is a T lymphocyte, a B lymphocyte, an NK cell, a monocyte/macrophage, or a dendritic cell.

"Effector cell" as used herein refers to a cell that expresses a surface receptor for the Fc domain of an immunoglobulin (FcR). For example, cells that express surface FcR for IgGs including FcγRIII (CD16), FcγRII (CD32) and FcγRIII (CD64) can act as effector cells. Such effector cells include monocytes, macrophages, natural killer (NK) cells, neutrophils and eosinophils.

A "therapeutic agent" is an agent that exerts a cytotoxic, cytostatic, or immunomodulatory effect on cancer cells, activated immune cells or other target cell population. Examples of therapeutic agents include cytotoxic agents, chemotherapeutic agents, cytostatic agents, and immunomodulatory agents.

A "cytotoxic effect" refers to the depletion, elimination and/or the killing of a target cell. A "cytotoxic agent" refers to an agent that has a cytotoxic effect on a cell. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to an antibody, e.g., an antibody, and used, for example, to treat a patient indicated for therapy with the antibody. In one embodiment, "cytotoxic agent" includes monoclonal antibodies, e.g., antibodies used in combination with the humanized antibodies described herein.

A "chemotherapeutic agent" is a chemical compound useful in the treatment of cancer. Examples of chemotherapeutic agents include alkylating agents, such a thioTEPA and cyclophosphamide (CYTOXAN™); alkyl sulfonates such as busulfan, improsulfan, and piposulfan; aziridines such as benzodopa, carboquone, meturedopa, and uredopa; ethylenimines and methylamelamines including altretamine, triethylenemelamine, triethylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues) and derivatives thereof; cryptophycines (particularly cryptophycin 1 and cryptophycin 8); dolastatin, auristatins (including analogues monomethyl-auristatin E and monomethyl-auristatin F (see, e.g., U.S. Published Application No. 2005-0238649, published Oct. 27, 2005, incorporated herein in its entirety); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phi1I, see for example, Agnew, Chem. Intl. Ed. Engl. 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubucin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elformithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine;

pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, 1986, "Prodrugs in Cancer Chemotherapy", In *Biochemical Society Transactions*, 14, pp. 375-382, 615th Meeting Belfast; and Stella et al., 1985, "Prodrugs: A Chemical Approach to Targeted Drug Delivery, In: "*Directed Drug Delivery*, Borchardt et al., (ed.), pp. 247-267, Humana Press. Useful prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

A "cytostatic effect" refers to the inhibition of cell proliferation. A "cytostatic agent" refers to an agent that has a cytostatic effect on a cell, thereby inhibiting the growth and/or expansion of a specific subset of cells.

The term "immunomodulatory effect" as used herein refers to a stimulation (immunostimulatory) or inhibition (immunomodulatory) of the development or maintenance of an immunologic response. Inhibition can be effected by, for example, by elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). An "immunomodulatory agent" refers to an agent that has an immunomodulatory effect on a cell. In some embodiments, an immunomodulatory agent has a cytotoxic or cytostatic effect on an immune cell that promotes an immune response.

The term "label" refers to a detectable compound or composition that is conjugated directly or indirectly to the antibody. The label may itself be detectable (e.g., radioisotope labels or fluorescent labels) or, in the case of an enzymatic label, may catalyze chemical alteration of a substrate compound or composition that is detectable. Labeled variant target binding agent can be prepared and used in various applications including in vitro and in vivo diagnostics.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "control sequences" refers to polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-target binding agent in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used to link the DNA sequences.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide typically having at least 20 contiguous or at least 50 contiguous amino acids of the polypeptide. A "derivative" is a polypeptide or fragment thereof having one or more non-conservative or conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof. "Antibody" includes the antibody in situ within recombinant cells since at least one component of the antibody's natural environment will not be present.

In certain embodiments, the antibody will be purified (1) to greater than 95% by weight of antibody as determined by the Lowry method, and in other aspects to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The term "heterologous," in the context of a polypeptide, means from a different source (e.g., a cell, tissue, organism, or species) as compared with another polypeptide, so that the two polypeptides are different. Typically, a heterologous polypeptide is from a different species.

In the context of immunoglobulin polypeptides or fragments thereof, "conservative substitution" means one or more amino acid substitutions that do not substantially reduce specific binding (e.g., as measured by the $K_D$) of the immunoglobulin polypeptide or fragment thereof to an antigen (i.e., substitutions that increase binding affinity, that do not significantly alter binding affinity, or that reduce binding affinity by no more than about 40%, typically no more than about 30%, more typically no more than about 20%, even more typically no more than about 10%, or most typically no more than about 5%, as determined by standard binding assays such as, e.g., ELISA).

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (e.g., as determined using one of the methods set forth infra).

The terms "similarity" or "percent similarity" in the context of two or more polypeptide sequences refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or 95% identical, or conservatively substituted, to the second amino acid sequence when compared to an equal number of amino acids as the number contained in the first sequence, or when compared to an alignment of polypeptides that has been aligned by, e.g., one of the methods set forth infra.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

In the context of antibodies, or derivatives thereof, a protein that has one or more polypeptide regions substantially identical or substantially similar to one or more antigen-binding regions (e.g., a heavy or light chain variable region, or a heavy or light chain CDR) of an antibody retains specific binding to an epitope recognized by the antibody, as determined using any of various standard immunoassays known in the art or as referred to herein.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers. It is also understood that all progeny may not be precisely identical in DNA content, due to deliberate or naturally occurring mutations. Mutant progeny that have the same function or biological activity as screened for in the originally transformed cell are included. Where distinct designations are intended, it will be clear from the context.

The term "subject" for purposes of treatment refers to any animal, particularly an animal classified as a mammal, including humans, domesticated and farm animals, and zoo, sports, or pet animals, such as dogs, horses, cats, cows, and the like. Preferably, the subject is human.

A "disorder", as used herein, and the terms "target-associated disorder" and "target-associated disease" refer to any condition that would benefit from treatment with an anti-target binding agent, as described herein. A "target-associated disorder" and "target-associated disease" typically express the target antigen, or a fragment thereof, on the cell surface. This includes chronic and acute disorders or diseases including those pathological conditions that predispose the mammal to the disorder in question. Non-limiting examples or disorders to be treated herein include cancer, hematological malignancies, benign and malignant tumors, leukemias and lymphoid malignancies, carcinomas, and inflammatory, angiogenic and immunologic disorders. Specific examples of disorders are disclosed infra.

The terms "treatment" and "therapy", and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder, thereby preventing or removing all signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein.

As used herein, the terms "prevention" or "prevent" refer to administration of an anti-target binding agent to a subject before the onset of a clinical or diagnostic symptom of a target-expressing cancer or immunological disorder (e.g., administration to an individual with a predisposition or at a high risk of acquiring the target-expressing cancer or immunological disorder) to (a) block the occurrence or onset of the target-expressing cancer or immunological disorder, or one or more of clinical or diagnostic symptoms thereof, (b) inhibit the severity of onset of the target-expressing cancer or immunological disorder, or (c) to lessen the likelihood of the onset of the target-expressing cancer or immunological disorder.

The term "intravenous infusion" refers to introduction of an agent, e.g., a therapeutic agent, into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent, e.g., a therapeutic agent, under the skin of an animal or human patient, typically within a pocket between the skin and underlying tissue, by relatively slow, sustained delivery from a drug receptacle. Pinching or drawing the skin up and away from underlying tissue may create the pocket.

The term "package insert" is used to refer to instructions customarily included in commercial packages of therapeutic products, that contain information about the indications, usage, administration, contraindications and/or warnings concerning the use of such therapeutic products.

A "liposome" is a small vesicle composed of various types of lipids, phospholipids and/or surfactant which is useful for delivery of a drug (such as an antibody) to a mammal. The components of the liposome are commonly arranged in a bilayer formation, similar to the lipid arrangement of biological membranes.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "effective amount" refers to the amount of an anti-target binding agent (e.g., an antibody or derivative or other binding agent) that is sufficient to inhibit the occurrence or ameliorate one or more clinical or diagnostic symptoms of a cancer or immunological disorder in a subject. An effective amount of an agent is administered according to the methods described herein in an "effective regimen." The term "effective regimen" refers to a combination of amount of the agent and dosage frequency adequate to accomplish treatment or prevention of cancer or immunological disorder.

The term "therapeutically effective amount" is used to refer to an amount of a therapeutic agent having beneficial patient outcome, for example, a growth arrest effect or deletion of the cell. In one aspect, the therapeutically effective amount has apoptotic activity, or is capable of inducing cell death. In another aspect, the therapeutically effective amount refers to a target serum concentration that has been shown to be effective in, for example, slowing disease progression. Efficacy can be measured in conventional ways, depending on the condition to be treated. For example, in neoplastic diseases or disorders characterized by cells expressing a target antigen, efficacy can be measured by assessing the time to disease progression (TTP), or determining the response rates (RR).

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which a target binding agent is administered.

The phrase "pharmaceutically acceptable salt," as used herein, refers to pharmaceutically acceptable organic or inorganic salts of an anti-target binding agent or therapeutic agent. The anti-target binding agent or therapeutic agent contains at least one amino group, and accordingly acid addition salts can be formed with this amino group or other suitable groups. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and an anti-target binding agent and/or therapeutic agent. Examples of solvents that form pharmaceutically acceptable solvates include, but are not limited to, water, isopropanol, ethanol, methanol, DMSO, ethyl acetate, acetic acid, and ethanolamine.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleunine-dolaproine-phenylalanine.

The abbreviations "fk" and "phe-lys" refer to the linker phenylalanine-lysine.

The abbreviation "mc" refers to maleimidocaproyl.

The abbreviations "vc" and "val-cit" refer to the peptide linker valine-citrulline.

The abbreviation "mcMMAF" refers to maleimidocaproyl-MMAF.

The abbreviation "vcMMAF" refers to maleimidocaproyl-valine-citrulline-p-aminobenzylcarbamoy linker.

II. Antibodies and Derivatives Thereof

The compositions and methods described herein encompass the use of a variant target binding agent that specifically binds to a target antigen on a cell. The target binding agent may exert a cytotoxic, cytostatic or immunomodulatory effect on the target antigen-expressing cancer cells, immune cells or other target cells. The target binding agent can be, for example, an antibody, an antigen-binding fragment of an antibody, a derivative thereof, or other binding agent comprising a portion of a Fc region of an antibody. The target binding agent can also include at least one complementarity determining region (CDR) of a target-binding antibody.

In one aspect, the target binding agent comprises one or more complementarity determining regions (CDRs) identical, substantially identical or substantially similar to one or more CDR(s) of a target binding antibody. For example, the binding agent can include a heavy chain CDR and/or a light chain CDR that is identical or substantially identical or substantially similar to a corresponding heavy chain CDR (H1, H2, or H3 regions) or corresponding light chain CDR (L1, L2, or L3 regions) of a monoclonal antibody. In typical embodiments, the anti-target binding agent has two or three heavy chain CDRs and/or two or three light chain CDRs that are identical, substantially identical or substantially similar to corresponding heavy and/or light chain CDRs of a monoclonal antibody.

In a specific embodiment, known antibodies for the treatment or prevention of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti HER2 monoclonal antibody, HERCEPTIN (trastuzumab; Genentech) for the treatment of patients with metastatic breast cancer; RITUXAN (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., Willner, D., Lasch, S. J., Henderson, A. J., Hofstead, S. J., Casazza, A. M., Firestone, R. A., Hellström, I., Hellstrom, K. E., "Cure of Xenografted Human Carcinomas by BR96-Doxorubicin Immunoconjugates" Science 1993, 261, 212-215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" Cancer Research 1997, 57, 100 105, mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" Cancer Res. 2000, 60, 3225-3231), mAbs against the CD70 antigen, such as 1F6 mAb and 2F2 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" J. Immunol., 151, 5896-5906, 1993: Wahl et al., 2002 Cancer Res. 62(13):3736-42). Many other internalizing antibodies that bind to tumor associated antigens can be used and have been reviewed (Franke, A. E., Sievers, E. L., and Scheinberg, D. A., "Cell surface receptor-targeted therapy of acute myeloid leukemia: a review" Cancer Biother Radiopharm. 2000, 15, 459 76; Murray, J. L., "Monoclonal antibody treatment of solid tumors: a coming of age" Semin Oncol. 2000, 27, 64 70; Breitling, F., and Dubel, S., Recombinant Antibodies, John Wiley, and Sons, New York, 1998).

In certain embodiments, the antibody is not Trastuzumab (full length, humanized anti-HER2 (MW 145167)), Herceptin F(ab')2 (derived from anti-HER2 enzymatically (MW 100000)), 4D5 (full-length, murine antiHER2, from hybridoma), rhu4D5 (transiently expressed, full-length humanized antibody), rhuFab4D5 (recombinant humanized Fab (MW 47738)), 4D5Fc8 (full-length, murine antiHER2, with mutated FcRn binding domain), or Hg ("Hingeless" full-length humanized 4D5, with heavy chain hinge cysteines mutated to serines. Expressed in *E. coli* (therefore non-glycosylated)).

In a specific embodiment, the target binding agent (e.g., antibody) comprises a binding region that specifically binds to CD20, CD30, CD33, CD70 or CD133.

In another specific embodiment, known antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques. In another embodiment, useful antibodies are immunospecific for the treatment of autoimmune diseases include, but are not limited to, Anti-Nuclear Antibody; Anti-ds DNA; Anti-ss DNA, Anti-Cardiolipin Antibody IgM, IgG; Anti-Phospholipid Antibody IgM, IgG; Anti-SM Antibody; Anti-Mitochondrial Antibody; Thyroid Antibody; Microsomal Antibody; Thyroglobulin Antibody; Anti-SCL 70; Anti Jo; Anti U1RNP; Anti La/SSB; Anti SSA; Anti-SSB; Anti-Perital Cells Antibody; Anti-Histones; Anti-RNP; C ANCA; P ANCA; Anti centromere; Anti Fibrillarin, and Anti-GBM Antibody.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNF R1, TNFR 2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

In a specific embodiment, the target binding agent (e.g., antibody) comprises a binding region that specifically binds to CD19, CD20, CD30 or CD70.

In a specific embodiment, the target binding agent comprises one or more complementarity determining regions (CDRs) identical, substantially identical or substantially similar to one or more CDR(s) of murine monoclonal antibody 1F6. (The nucleic acid and amino acid sequences of the heavy and light chain variable regions of 1F6 are set forth in SEQ ID NO:1 and SEQ ID NO:2, and SEQ ID NO: 21 and SEQ ID NO: 22, respectively, and are disclosed in International Patent Publication No. WO 04/073656, the disclosure of which is incorporated by reference herein.) For example, the binding agent can include a heavy chain CDR and/or a light chain CDR that is identical or substantially identical or substantially similar to a corresponding heavy chain CDR (H1, H2, or H3 regions) or corresponding light chain CDR (L1, L2, or L3 regions) of mAb 1F6. In typical embodiments, the anti-target binding agent has two or three heavy chain CDRs and/or two or three light chain CDRs that are identical, substantially identical or substantially similar to corresponding heavy and/or light chain CDRs of mAb 1F6.

For example, in some embodiments, where the anti-target binding agent has at least one heavy chain CDR substantially identical or substantially similar to a heavy chain CDR of target binding monoclonal antibody, the binding agent can further include at least one light chain CDR that is substantially identical or substantially similar to a light chain CDR of the target binding monoclonal antibody.

In some embodiments, the anti-target binding agent includes a heavy or light chain variable domain, the variable domain having (a) a set of three CDRs identical, substantially identical or substantially similar to corresponding CDRs of a target binding monoclonal antibody, and (b) a set of four variable region framework regions from a human immunoglobulin. For example, an anti-CD70 antibody can include a heavy and/or light chain variable domain(s), the variable domain(s) having (a) a set of three CDRs, in which the set of CDRs are from monoclonal antibody 1F6, and (b) a set of four framework regions derived from a human IgG. The antibody can optionally include a hinge region. In an exemplary embodiment, the anti-CD70 antibody is a fully humanized antibody.

In another aspect, the target binding agent comprises one or more complementarity determining regions (CDRs) substantially identical or substantially similar to one or more CDR(s) of monoclonal antibody 2F2. (The nucleic acid and amino acid sequences of the heavy and light chain variable regions of 2F2 are set forth in SEQ ID NO:27 and SEQ ID NO:28, and SEQ ID NO: 29 and SEQ ID NO: 30, respectively, and are disclosed in International Patent Publication No. WO 04/073656, the disclosure of which is incorporated by reference herein.) For example, the binding agent can include a heavy chain CDR and/or a light chain CDR that is identical or substantially identical or substantially similar to a corresponding heavy chain CDR (H1, H2, or H3 regions) or corresponding light chain CDR (L1, L2, or L3 regions) of mAb 2F2. In typical embodiments, the anti-target binding agent has two or three heavy chain CDRs and/or two or three light chain CDRs that are identical, substantially identical or substantially similar to corresponding heavy and/or light chain CDRs of mAb 2F2.

For example, in some embodiments, where an anti-CD70 antibody has at least one heavy chain CDR substantially identical or substantially similar to a heavy chain CDR of mAb 2F2, the antibody or derivative thereof can further include at least one light chain CDR that is substantially identical or substantially similar to a light chain CDR of mAb 2F2.

In some embodiments, the anti-target binding agent includes a heavy or light chain variable domain, the variable domain having (a) a set of three CDRs identical, substantially identical or substantially similar to corresponding CDRs of mAb 2F2, and (b) a set of four variable region framework regions from a human immunoglobulin. For example, an anti-CD70 antibody can include a heavy and/or light chain variable domain(s), the variable domain(s) having (a) a set of three CDRs, in which the set of CDRs are from monoclonal antibody 2F2, and (b) a set of four framework regions derived from a human IgG. The antibody can optionally include a hinge region. In an exemplary embodiment, the anti-CD70 antibody is a fully humanized antibody.

In some embodiments, the framework regions are chosen from human germline exon $V_H$, $J_H$, Vκ and Jκ sequences. For example, acceptor sequences for humanization of FR of a c1F6 $V_H$ domain can be chosen from germline $V_H$ exons $V_H$1-18 (Matsuda et al., 1993, *Nature Genetics* 3:88-94) or $V_H$1-2 (Shin et al., 1991, *EMBO J.* 10:3641-3645) and for the hinge region ($J_H$), exon $J_H$-6 (Mattila et al., 1995, *Eur. J. Immunol.* 25:2578-2582). In other examples, germline Vκ exon B3 (Cox et al., 1994, *Eur. J. Immunol.* 24:827-836) and Jκ exon Jκ-1 (Hieter et al., 1982, *J. Biol. Chem.* 257:1516-1522) can be chosen as acceptor sequences for c1F6 $V_L$ domain humanization.

In some embodiments, the sequence of the framework region of the humanized anti-CD70 antibody includes a derivative of the acceptor human germline exon used, including derivatives in which mouse donor residues are reintroduced. These residues include reintroduction of the mouse donor residue at one or more of positions H46, H67, H68, H69, H70, H71, H80, H81, H82, H82A and H91 in the $V_H$ domain, according to the Kabat numbering convention.

The following Table 1 indicates the regions of humanized 1F6 and 2F2 to which each SEQ ID NO: corresponds to.

TABLE 1

| MOLECULE | NUCLEOTIDE OR AMINO ACID | SEQ ID NO: |
|---|---|---|
| c1F6 Heavy Chain Variable Region | Nucleotide | 1 |
| c1F6 Heavy Chain Variable Region | Amino Acid | 2 |
| h1F6 hV$_H$-D + hIgG$_1$ Constant Domain | Nucleotide | 3 |
| h1F6 hV$_H$-D + hIgG$_1$ Constant Domain | Amino Acid | 4 |
| h1F6 hV$_H$-E | Nucleotide | 5 |
| h1F6 hV$_H$-E | Amino Acid | 6 |
| h1F6 hV$_H$-E + hIgG$_1$ Constant Domain | Nucleotide | 7 |
| h1F6 hV$_H$-E + hIgG$_1$ Constant Domain | Amino Acid | 8 |
| h1F6 hV$_H$-H | Nucleotide | 9 |
| h1F6 hV$_H$-H | Amino Acid | 10 |
| h1F6 hV$_H$-H + hIgG$_1$ Constant Domain | Nucleotide | 11 |
| h1F6 hV$_H$-H + hIgG$_1$ Constant Domain | Amino Acid | 12 |
| h1F6 hV$_H$-J | Nucleotide | 13 |
| h1F6 hV$_H$-J | Amino Acid | 14 |
| h1F6 hV$_H$-J + hIgG$_1$ Constant Domain | Nucleotide | 15 |
| h1F6 hV$_H$-J + hIgG$_1$ Constant Domain | Amino Acid | 16 |
| h1F6 hV$_H$-M | Nucleotide | 17 |
| h1F6 hV$_H$-M | Amino Acid | 18 |
| h1F6 hV$_H$-M + hIgG$_1$ Constant Domain | Nucleotide | 19 |
| h1F6 hV$_H$-M + hIgG$_1$ Constant Domain | Amino Acid | 20 |
| c1F6 Light Chain Variable Region | Nucleotide | 21 |
| c1F6 Light Chain Variable Region | Amino Acid | 22 |
| hV$_L$A | Nucleotide | 23 |
| hV$_L$A | Amino Acid | 24 |
| hV$_L$A + human κ constant domain | Nucleotide | 25 |
| hV$_L$A + human κ constant domain | Amino Acid | 26 |
| c2F2 Heavy Chain Variable Region | Nucleotide | 27 |
| c2F2 Heavy Chain Variable Region | Amino Acid | 28 |
| c2F2 Light Chain Variable Region | Nucleotide | 29 |
| c2F2 Light Chain Variable Region | Amino Acid | 30 |

In some embodiments, the target binding agent can be a humanized antibody or antigen-binding fragment of antibody 1F6 or 2F2. In some embodiments, the antibody or antigen-binding fragment comprises a polypeptide chain having the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain having the amino acid sequence of SEQ ID NO:24.

In some embodiments, the antibody or antigen-binding fragment comprises a polypeptide chain that is at least 80% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 85% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 90% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 95% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 99% identical to the amino acid sequence of SEQ ID NO:6, SEQ ID NO:10, SEQ ID NO:14, SEQ ID NO:18, or amino acids 20-137 of SEQ ID NO:4. In some embodiments, the polypeptide does not have the amino acid sequence of the heavy chain variable region of antibody 1F6 or 2F2.

In some embodiments, the antibody or antigen-binding fragment comprises a polypeptide chain that is at least 80% identical to the amino acid sequence of SEQ ID NO:24. In some embodiments, the antibody or antigen-binding fragment comprises a polypeptide chain that is at least 85% identical to the amino acid sequence of SEQ ID NO:24. In some embodiments, the antibody or antigen-binding fragment comprises a polypeptide chain that is at least 90% identical to the amino acid sequence of SEQ ID NO:24. In some embodiments, the antibody or antigen-binding fragment comprises a polypeptide chain that is at least 95% identical to the amino acid sequence of SEQ ID NO:24. In some embodiments, the antibody or antigen-binding fragment comprises a polypeptide chain that is at least 99% identical to the amino acid sequence of SEQ ID NO:24. In some embodiments, the polypeptide does not have the amino acid sequence of the light chain variable region of antibody 1F6 or 2F2.

In some embodiments, the anti-target binding agent competes with monoclonal antibody 1F6 or 2F2 for binding to human CD70. In some embodiments, the target binding agent does not induce an agonistic or antagonistic signal when binding to CD70 (e.g., does not stimulate proliferation). In some embodiments, the target binding agent blocks binding of CD27 to CD70 by at least 20%, at least 30%, at least 40%, at least 50%, at least 60, at least 70%, at least 80% or at least 90%.

The target binding agent can be an antibody, such as a humanized antibody, a single chain antibody, an scFv, a diabody, a Fab, a minibody, an scFv-Fc, a Fv, or the like. In some embodiments, an antigen-binding region can be joined to an Fc domain or domains such as, for example, the hinge-$C_H2$-$C_H3$ domains of an immunoglobulin, or a portion or fragment of an effector domain(s). Antigen-binding antibody fragments, including single-chain antibodies, can comprise, for example, the variable region(s) in combination with the entirety or a portion of an Fc domain (e.g., a $C_H2$ and/or $C_H3$ domain alone or in combination with a $C_H1$, hinge and/or $C_L$ domain). Also, antigen-binding fragments can comprise any combination of Fc domains. In some embodiments, the antibody can be a single chain antibody comprising an antigen-binding variable region joined to hinge-$C_H2$-$C_H3$ domains.

The Fc domains of the target binding agent can be from any suitable human immunoglobulin isotype.

The target binding agent may be conjugated to a therapeutic agent, such as a cytotoxic, cytostatic or immunomodulatory agent. In a specific embodiment, the target binding agent is conjugated to a therapeutic agent, such as a cytotoxic, cytostatic or immunomodulatory agent. Suitable therapeutic agents are described herein.

Suitable cytotoxic agents can be, for example, an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In specific embodiments, the cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In specific embodiments, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, or eleutherobin.

Suitable immunomodulatory agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

In antibody drug conjugates (ADCs), the antibody can be conjugated directly to the cytotoxic agent or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

In some embodiments, a target binding agent can be a chimeric antibody, comprising a human or non-human Fc region or portion thereof. For example, the antibody can include a Fc domain or portion of non-human origin, e.g., rodent (e.g., mouse or rat), donkey, sheep, rabbit, goat, guinea pig, camelid, horse, chicken or monkey (e.g., macaque, rhesus or the like).

A target binding agent, such as an antibody, can be monospecific, bispecific, trispecific, or of greater multispecificity. Multispecific antibodies may be specific for different epitopes of a target antigen and/or may be specific for both a target antigen as well as for a heterologous antigen. (See, e.g., PCT Publication Nos. WO 93/17715, WO 92/08802, WO 91/00360, and WO 92/05793; Tutt et al., 1991, *J. Immunol.* 147:60-69; U.S. Pat. Nos. 4,474,893; 4,714,681; 4,925,648; 5,573,920; and 5,601,819; Kostelny et al., 1992, *J. Immunol.* 148:1547-1553.) Multispecific antibodies, including bispecific and trispecific antibodies, useful for practicing the methods described herein are antibodies that immunospecifically bind to a target antigen and a second cell surface receptor or receptor complex. In some embodiments, the binding of the portion of the multispecific antibody to the second cell surface molecule or receptor complex may enhance the functions of the target binding agent.

Target binding agents and derivatives thereof may also be described or specified in terms of their binding affinity to the target antigen. Typical binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Useful monoclonal antibodies of the invention are homogeneous populations of antibodies to a particular antigenic determinant, e.g., a cell antigen (such as a cancer cell antigen or a non-malignant effector or accessory cell antigen), a viral antigen, a microbial antigen, a protein, a peptide, a carbohydrate, a chemical, a nucleic acid, or antigen-binding fragments thereof). A monoclonal antibody (mAb) to an antigen of interest can be prepared by using any technique known in the art, including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988); and Hammerling et al., In *Monoclonal Antibodies and T-Cell Hybridomas*, pp. 563-681 (Elsevier, N.Y., 1981). These include, but are not limited to, the hybridoma technique originally described by Köhler and Milstein (1975, *Nature* 256, 495-497), the human B cell hybridoma technique (Kozbor et al., 1983, *Immunology Today* 4:72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Examples of phage display methods that can be used to make the antibodies include, e.g., those disclosed in Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Jardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187: 9-18; Burton et al., 1994, *Advances in Immunology* 57:191-280; PCT Application No. PCT/GB91/01134; PCT Publication Nos. WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Useful monoclonal antibodies include, but are not limited to, human monoclonal antibodies, humanized monoclonal antibodies, chimeric monoclonal antibodies and functionally active antibody fragments. Human monoclonal antibodies may be made by any of numerous techniques known in the art (see, e.g., Teng et al., 1983, *Proc. Natl. Acad. Sci. USA.* 80:7308-7312; Kozbor et al., 1983, *Immunology Today* 4:72-79; Olsson et al., 1982, *Meth. Enzymol.* 92:3-16; and U.S. Pat. Nos. 5,939,598 and 5,770,429).

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806; each of which is incorporated herein by reference in its entirety. Other human antibodies can be obtained commercially from, for example, Abgenix, Inc. (Freemont, Calif.) and Medarex (Sunnyvale, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (see, e.g., Jespers et al., 1994, *Biotechnology* 12:899-903). Human antibodies also can be produced using various techniques known in the art, including phage display libraries (Hoogenboom and Winter, 1991, *J. Mol. Biol.* 227: 381; Marks et al., 1991, J. Mol. Biol. 222:581; Quan and Carter, 2002, *The rise of monoclonal antibodies as therapeutics*, In Anti-IgE and Allergic Disease, Jardieu and Fick Jr., eds., Marcel Dekker, New York, N.Y., Chapter 20, pp. 427-469).

Additionally, recombinant antibodies, such as chimeric and humanized monoclonal antibodies, comprising both human and non-human portions, which can be made using standard recombinant DNA techniques, are useful antibodies. (See, e.g., Cabilly et al., U.S. Pat. No. 4,816,567; and Boss et al., U.S. Pat. No. 4,816,397, both of which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.)

In some embodiments, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., U.S. Pat. No. 5,585, 089; Riechmann et al., 1988, *Nature* 332:323.) Antibodies can be humanized using a variety of techniques known in the art including, for example, CDR-grafting (see, e.g., EP 0239400; PCT Publication No. WO 91/09967; U.S. Pat. Nos. 5,225,539; 5,530,101; and 5,585,089), veneering or resurfacing (see, e.g., EP 0592106; EP 0519596; Padlan, 1991,

*Molecular Immunology* 28(4/5):489-498; Studnicka et al., 1994, *Protein Engineering* 7(6):805-814; Roguska et al., 1994, *Proc. Natl. Acad. Sci. USA* 91:969-973), and chain shuffling (see, e.g., U.S. Pat. No. 5,565,332) (all of these references are incorporated by reference herein).

Such chimeric and humanized monoclonal antibodies can be produced by recombinant DNA techniques known in the art, for example using methods described in International Publication Nos. WO 87/02671 and WO 86/01533; European Patent Publication Nos. EP 0184187; EP 0171496; EP 0173494; and EP 012023; U.S. Pat. Nos. 4,816,567 and 5,225,539; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; Shaw et al., 1988, *J. Natl. Cancer Inst.* 80:1553-1559; Morrison, 1985, *Science* 229:1202-1207; Oi et al., 1986, *BioTechniques* 4:214; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

In some embodiments, the antibody is monospecific. The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and Traunecker et al., 1991, *EMBO J.* 10:3655-3659.

According to a different approach, antibody variable domains with the desired binding specificities (antibody-antigen combining sites) are fused to immunoglobulin constant domain sequences. The fusion typically is with an immunoglobulin heavy chain constant region, comprising at least part of the hinge, $C_H2$, and $C_H3$ domains. It is preferred to have the first heavy-chain constant region ($C_H1$), containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690; which is incorporated herein by reference in its entirety).

For further details for generating bispecific antibodies see, for example, Suresh et al., 1996, *Methods in Enzymology* 121:210; Rodrigues et al., 1993, *J. Immunology* 151:6954-6961; Carter et al., 1992, *Bio/Technology* 10:163-167; Carter et al., 1995, *J. Hematotherapy* 4:463-470; Merchant et al., 1998, *Nature Biotechnology* 16:677-681. Using such techniques, bispecific antibodies can be prepared for use in the treatment or prevention of disease as defined herein.

Bifunctional antibodies are also described in European Patent Publication No. EP 0105360. As disclosed in this reference, hybrid or bifunctional antibodies can be derived either biologically, e.g., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication No. WO 83/03679, and European Patent Publication No. EP 0217577, both of which are incorporated herein by reference.

The antibody also can be a functionally active fragment, derivative or analog of an antibody that immunospecifically binds to a desired target antigen (e.g., a cancer cell antigen or a non-malignant effector cell antigen) or other antibodies bound to a target cell(s) or matrix. In this regard, "functionally active" means that the fragment, derivative or analog is able to elicit anti-anti-idiotype antibodies, which recognize the same antigen that the antibody from which the fragment, derivative or analog is derived recognizes. In an exemplary embodiment, the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIAcore assay) (see, e.g., Kabat et al., 1991, *Sequences of Proteins of Immunological Interest*, Fifth Edition, National Institute of Health, Bethesda, Md.; Kabat et al., 1980, *J. Immunology* 125(3):961-969).

Other useful antibodies include fragments of antibodies such as, but not limited to, $F(ab')_2$ fragments, Fab' fragments, Fab fragments, Fvs, single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), scFv, sc-Fv-Fc, FvdsFv, minibodies, diabodies, triabodies, tetrabodies, or any other molecule comprising CDRs and that have the same specificity as the antibody.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, typically at least a 10, 20 or 50 amino acid portion of the protein) that is not the antibody. In some embodiments, the antibody or fragment thereof can be covalently linked to the other protein at the N-terminus of the constant domain.

As set forth supra, a target binding agent can be a derivative of a target binding antibody. Generally, an antibody derivative comprises an antigen-binding fragment or conservatively substituted polypeptides and at least one polypeptide region or other moiety heterologous to the antibody. For example, an antibody can be modified, e.g., by the covalent attachment of any type of molecule. Typical modifications include, e.g., deglycosylation, glycosylation, acetylation, pegylation, phosphorylation, amidation, derivatization by known protecting/blocking groups, proteolytic cleavage, linkage to a cellular ligand (e.g., an albumin-binding molecule) or other protein, and the like. Any of numerous chemical modifications may be carried out by known techniques, including, but not limited to specific chemical cleavage, acetylation, formylation, metabolic synthesis of tunicamycin, etc.

In some embodiments, the antibody derivative is a multimer, such as, for example, a dimer, comprising one or more monomers, where each monomer includes (i) an antigen-binding region of an antibody, or a polypeptide region derived therefrom (such as, e.g., by conservative substitution of one or more amino acids), and (ii) a multimerizing (e.g., dimerizing) polypeptide region, such that the antibody derivative forms multimers (e.g., homodimers) that specifically bind to the target antigen. In typical embodiments, an antigen-binding region of an antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunological disorders or cancers, the derivative is subjected to conditions that allow formation of a homodimer or heterodimer. A heterodimer, as used herein, may comprise identical dimerization domains but different antigen-binding regions, identical antigen-binding regions but different dimerization domains, or different antigen-binding regions and dimerization domains.

Typical dimerization domains are those that originate from transcription factors. In one embodiment, the dimerization domain is that of a basic region leucine zipper ("bZIP") (see Vinson et al., 1989, Science 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See, e.g., Landschultz et al., 1988, Science 240:1759-64; Baxevanis and Vinson, 1993, Curr. Op. Gen. Devel. 3:278-285; O'Shea et al., 1989, Science 243:538-542.) In another embodiment, the dimerization domain is that of a basic-region helix-loop-helix ("bHLH") protein. (See, e.g., Murre et al., 1989, Cell 56:777-783. See also Davis et al., 1990, Cell 60:733-746; Voronova and Baltimore, 1990, Proc. Natl. Acad. Sci. USA 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0367166; and WO 96/04388.)

Heterodimers are known to form between Fos and Jun (Bohmann et al., 1987, Science 238:1386-1392), among members of the ATF/CREB family (Hai et al., 1989, Genes Dev. 3:2083-2090), among members of the C/EBP family (Cao et al., 1991, Genes Dev. 5:1538-52; Williams et al., 1991, Genes Dev. 5:1553-67; Roman et al., 1990, Genes Dev. 4:1404-15), and between members of the ATF/CREB and Fos/Jun families (Hai and Curran, 1991, Proc. Natl. Acad. Sci. USA 88:3720-24). Therefore, when a variant target binding agent is administered to a subject as a heterodimer comprising different dimerization domains, any combination of the foregoing may be used.

In other embodiments, an antibody derivative is an antibody conjugated to a second antibody (an "antibody heteroconjugate") (see, e.g., U.S. Pat. No. 4,676,980). Heteroconjugates useful for practicing the present methods comprise an antibody that binds to the target antigen (e.g., an antibody that has the CDRs and/or heavy chains of a monoclonal antibody, e.g., 2F2 or 1F6) and an antibody that binds to a surface receptor or receptor complex. In a typical embodiment, the binding of the portion of the multispecific antibody to the second cell surface molecule or receptor complex enhances the functions of the antibody. In other embodiments, the antibody can be a therapeutic agent. Suitable antibody therapeutic agents are described herein.

In exemplary embodiments, the antibody or derivative thereof competitively inhibits binding of a monoclonal antibody for its target antigen or a ligand of the target antigen, as determined by any method known in the art for determining competitive binding (e.g., an immunoassays). In typical embodiments, the antibody competitively inhibits binding of the monoclonal antibody or the ligand by at least 50%, at least 60%, at least 70%, or at least 75%. In other embodiments, the antibody competitively inhibits binding of the monoclonal antibody or the ligand by at least 80%, at least 85%, at least 90%, or at least 95%.

In exemplary embodiments, the antibody or derivative thereof competitively inhibits binding of mAb 1F6 or 2F2 to CD70, as determined by any method known in the art for determining competitive binding (such as, e.g., the immunoassays described herein). In typical embodiments, the antibody competitively inhibits binding of 1F6 or 2F2 to CD70 by at least 50%, at least 60%, at least 70%, or at least 75%. In other embodiments, the antibody competitively inhibits binding of 1F6 or 2F2 to CD70 by at least 80%, at least 85%, at least 90%, or at least 95%.

Antibodies can be assayed for specific binding to a target antigen by any of various known methods. Immunoassays which can be used include, for example, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well-known in the art. (See, e.g., Ausubel et al., eds., Short Protocols in Molecular Biology (John Wiley and Sons, Inc., New York, 4th ed. 1999); Harlow and Lane, Using Antibodies: A Laboratory Manual (Cold Spring Harbor Laboratory Press, Cold Spring Harbor, N.Y., 1999.)

Further, the binding affinity of an antibody to its target antigen and the off-rate of an antibody-target interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for the target antigen and the binding off-rates can then be determined from the data by Scatchard plot analysis. Competition with a second antibody can also be determined using radioimmunoassays. In this case, the antigen is incubated with the antibody of interest conjugated to a labeled compound (e.g., $^3$H or $^{125}$I) in the presence of increasing amounts of an unlabeled second antibody. Alternatively, the binding affinity of an antibody to its antigen and the on- and off-rates of an antibody-antigen interaction can be determined by surface plasmon resonance. In some embodiments, the antibodies or derivatives thereof can be targeted to and accumulate on the membrane of a target antigen-expressing cell.

In accordance with the methods described herein, variant target binding agents (e.g., antibodies or derivatives or fragments thereof), when conjugated to a therapeutic agent, can be internalized and accumulate within a target antigen expressing cell, where the therapeutic agent exerts an effect (e.g., a cytotoxic, cytostatic, or immunomodulatory effect). In additional embodiments, variant target binding agents (e.g., antibodies or derivatives or fragments thereof), when conjugated to a therapeutic agent, can be targeted to and accumulate on the membrane of a target antigen expressing cell, where the therapeutic agent exerts an effect (e.g., a cytotoxic, cytostatic, or immunomodulatory effect). In yet other embodiments, variant target binding agents (e.g., antibodies or derivatives or fragments thereof), when conjugated to a therapeutic agent, can be targeted to a biological molecule in a cell (e.g., an inflammatory agent) and accumulate at or adjacent cells secreting or binding the biological molecule, where the therapeutic agent exerts an effect (e.g., a cytotoxic, cytostatic, or immunomodulatory effect).

Whether a given variant target binding agent (e.g., antibody or derivative or fragment thereof), when conjugated to a therapeutic agent, exerts a corresponding therapeutic effect upon binding a target antigen expressing cell can be readily determined, e.g., by (1) incubating target antigen expressing cells independently with the target binding agent, (2) incubating the cells with a secondary reagent that is conjugated to the therapeutic agent and that specifically binds to the target binding agent, and (3) assaying the cells for the corresponding therapeutic effect. Multiple antibodies or antibody derivatives can be readily evaluated via such assays using a secondary reagent that specifically binds a polypeptide region shared by each antibody or derivative thereof (e.g., an anti-Ig antibody). For example, an anti-CD70 mAb that binds CD70 and exerts a cytotoxic effect when conjugated to a cytotoxic agent (e.g., an auristatin such as, for example, AFP, MMAF, or MMAE) can be identified by an indirect immunotoxicity assay such as, for example, described by Chun et al., 2003, *Supplement to Clinical Cancer Research*, Vol. 9. Briefly, the cytotoxic agent is conjugated to a secondary antibody (e.g., for murine mAbs, a polyclonal anti-mouse IgG); CD70-expressing cells are incubated with both the primary and cytotoxic agent-conjugated secondary antibody (e.g., in 96-well plates, using hybridoma supernatant for the primary antibody); and primary antibody-dependent cytotoxicity is assessed in a standard cytotoxicity assay (e.g., an MTT cell viability assay).

The antibodies and derivatives thereof can be produced by methods known in the art for the synthesis of proteins, typically, e.g., by recombinant expression techniques. Recombinant expression of an antibody or derivative thereof that binds to the target antigen typically includes construction of an expression vector containing a nucleic acid that encodes the antibody or derivative thereof. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication Nos. WO 86/05807 and WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the antibody. In typical embodiments for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an antibody or derivative thereof. Typically, eukaryotic cells, particularly for whole recombinant antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of antibodies and derivatives thereof (see, e.g., Foecking et al., 1986, *Gene* 45:101; Cockett et al., 1990, *Bio/Technology* 8:2).

Other host-expression systems include, for example, plasmid-based expression systems in bacterial cells (see, e.g., Ruther et al., 1983, *EMBO* 1, 2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of recombinant antibody or derivative thereof or other target binding agent. For example, cell lines that stably express the antibody or derivative thereof can be engineered by transformation of host cells with DNA controlled by appropriate expression control elements (e.g., promoter and enhancer sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk', hgprt' or aprt cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley and Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally, e.g., Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see Crouse et al., 1983, *Mol. Cell. Biol.* 3:257).

Where the antibody comprises both a heavy and a light chain or derivatives thereof, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody or derivative thereof has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, *Cell* 37:767), and the "flag" tag.

Once an antibody or derivative thereof is produced, its ability to exert a cytostatic or cytotoxic effect on expressing cancer cells or an immunomodulatory effect on an immune cell is determined by the methods described infra or as known in the art.

To minimize activity of the antibody to target cells (e.g., immune cells or cancer cells), an antibody that specifically binds to cell membrane-bound target antigen, but not to soluble antigen, can be used, so that the antibody is concentrated at the cell surface of the target cell.

Typically, the target binding agent (e.g., antibody or derivative) is substantially purified (e.g., substantially free from substances that limit its effect or produce undesired side-effects). In some embodiments, the target binding agent is at least about 40% pure, at least about 50% pure, or at least about 60% pure. In some embodiments, the target binding agent is at least about 60-65%, 65-70%, 70-75%, 75-80%, 80-85%, 85-90%, 90-95%, or 95-98% pure. In some embodiments, the target binding agent is approximately 99% pure.

III. Other Target Binding Agents

Further target binding agents include fusion proteins (i.e., proteins that are recombinantly fused or chemically conjugated, including both covalent and non-covalent conjugation) to heterologous proteins (of typically at least 10, 20, 30, 40, 50, 60, 70, 80, 90 or at least 100 amino acids). Such target binding agents can include a portion that binds to the target antigen and a variant immunoglobulin (Ig) Fc domain or a functional equivalent thereof. As used herein, a functional equivalent of Ig Fc domain binds to an Fc receptor on an immune cell with phagocytic or lytic activity or by binding of an Fc effector domain(s) to components of the complement system. A variant of a functional equivalent of Ig Fc domain exhibits reduced binding to an Fcγ receptor, as further described herein. The fusion protein does not necessarily need to be directly linked, but may occur through linker sequences.

For example, a target binding agent can be produced recombinantly by fusing the coding region of one or more of the CDRs or the variable region of an antibody in frame with a sequence coding for a heterologous protein. The heterologous protein can include, for example, a variant Ig Fc domain, a variant of a functional equivalent thereof or other functional domain to provide one or more of the following characteristics: promote stable expression; provide a means of facilitating high yield recombinant expression; provide a cytostatic, cytotoxic or immunomodulatory activity; and/or provide a multimerization domain.

In some embodiments, the target binding agent can include one or more CDRs from an antibody that binds to the target antigen, at least a portion of an Fc region and exhibits reduced binding to an Fcγ receptor.

IV. Antibody Drug Conjugates

Compositions useful in the treatment of a target antigen-expressing cancer or an immunological disorder comprise antibody drug conjugates (ADCs) or ADC derivatives. An "ADC" as used herein refers to an antibody conjugated to a therapeutic agent. An "ADC derivative" as used herein refers to derivative of an antibody conjugated to a therapeutic agent. An "ADC" or "ADC derivative" also includes other binding agents that bind to a target antigen and comprises at least a portion of an Fc region conjugated to a therapeutic agent. In certain embodiments, the ADC comprises an anti-CD70 antibody (e.g., mAb 1F6 or 2F2 or a fragment or derivative thereof, including, for example, a chimeric or humanized form thereof). The ADCs or ADC derivatives as described herein produce clinically beneficial effects on target antigen expressing cells when administered to a subject with a target antigen expressing cancer or an immunological disorder, typically when administered alone, but also in combination with other therapeutic agents.

In typical embodiments, the antibody or derivative thereof or other binding agent or is conjugated to a cytotoxic or immunomodulatory agent, such that the resulting ADC or ADC derivative exerts a cytotoxic or cytostatic effect on a target antigen expressing cancer cell, or a cytotoxic, cytostatic, or immunomodulatory effect on an immune cell (e.g., an activated lymphocyte or dendritic cell) when taken up or internalized by the cell. Particularly suitable moieties for conjugation to antibodies or antibody derivatives, or other binding agents, are chemotherapeutic agents, prodrug converting enzymes, radioactive isotopes or compounds, or toxins. For example, an antibody or derivative thereof or other binding agent can be conjugated to a cytotoxic agent such as a chemotherapeutic agent (see infra), or a toxin (e.g., a cytostatic or cytocidal agent such as, e.g., abrin, ricin A, pseudomonas exotoxin, or diphtheria toxin). Examples of additional agents that are useful for conjugating to the antibody molecules are provided infra.

In other embodiments, the antibody or derivative thereof or other binding agent is conjugated to a pro-drug converting enzyme. The pro-drug converting enzyme can be recombinantly fused to the antibody or derivative thereof or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Dekker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

In accordance with the methods described herein, the ADC or ADC derivative is internalized and accumulates within a target antigen expressing cell, where the ADC or ADC derivative exerts a therapeutic effect (e.g., a cytotoxic, cytostatic, or immunomodulatory effect). Methods for determining accumulation and rates of accumulation are found in U.S. Provisional Application No. 60/400,404, filed Jul. 31, 2002; the disclosure of which is incorporated by reference herein.

Typically, when using an antibody or derivative thereof or other binding agent conjugated to a therapeutic agent (e.g., a drug or a prodrug converting enzyme), the agent is preferentially active when internalized by cells of the cancer to be treated or by activated immune cells (e.g., activated lymphocytes or dendritic cells). In other embodiments, the ADC or ADC derivative is not internalized, and the drug is effective to deplete or inhibiting target antigen expressing cells by binding to the cell membrane. In yet other embodiments, ADC or ADC derivatives thereof can be targeted to a biological molecules in a cell (e.g., an inflammatory agent) and accumulate at or adjacent cells secreting or binding the biological molecule, where the therapeutic agent exerts an effect (e.g., a cytotoxic, cytostatic, or immunomodulatory effect).

To minimize activity of the therapeutic agent outside the activated immune cells or target antigen expressing cancer cells, an antibody or derivative thereof or other binding agent that specifically binds to cell membrane-bound target antigen, but not to soluble target antigen, can be used, so that the therapeutic agent is concentrated at the cell surface of the activated immune cell or target antigen expressing cancer cell. Alternatively, in a more typical embodiment, the therapeutic agent is conjugated in a manner that reduces its activity unless it is cleaved off the antibody or derivative thereof or other binding agent (e.g., by hydrolysis or by a cleaving agent). In such embodiments, the therapeutic agent is attached to the or derivative thereof or other binding agent with a cleavable linker that is sensitive to cleavage in the intracellular environment of the activated immune cell or target antigen expressing cancer cell but is not substantially sensitive to the extracellular environment, such that the conjugate is cleaved from the or derivative thereof or other binding agent when it is internalized by the activated immune cell or target antigen expressing cancer cell (e.g., in the endosomal or, for example by virtue of pH sensitivity or protease sensitivity, in the lysosomal environment or in a caveolea).

Further, in certain embodiments, the ADC or ADC derivative comprises a therapeutic agent that is charged relative to the plasma membrane, thereby further minimizing the ability of the agent to cross the plasma membrane once internalized by a cell. As used herein, a "charged agent" means an agent that (a) is polarized, such that one region of the agent has a charge relative to the plasma membrane, or (b) has a net charge relative to the plasma membrane.

Typically, the ADC or ADC derivative is substantially purified (e.g., substantially free from substances that limit its effect or produce undesired side-effects). In certain specific embodiments, the ADC or ADC derivative is 40% pure, more typically about 50% pure, and most typically about 60% pure. In other specific embodiments, the ADC or ADC derivative is at least approximately 60-65%, 65-70%, 70-75%, 75-80%, 80-85%, 85-90%, 90-95%, or 95-98% pure. In another specific embodiment, the ADC or ADC derivative is approximately 99% pure.

A. Linkers

Typically, the ADC or ADC derivative comprises a linker region between the therapeutic agent and the antibody or derivative thereof or other binding agent. As noted supra, in typical embodiments, the linker is cleavable under intracellular conditions, such that cleavage of the linker releases the therapeutic agent from the antibody in the intracellular environment.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in CD70-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other such linkers are described, e.g., in U.S. Pat. No. 6,214,345. In specific embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of ADC or ADC derivative, are cleaved when the ADC or ADC derivative present in an extracellular environment (e.g., in plasma). Whether a linker is not substantially sensitive to the extracellular environment can be determined, for example, by incubating independently with plasma both (a) the ADC or ADC derivative (the "ADC sample") and (b) an equal molar amount of unconjugated antibody or derivative thereof or other binding agent or therapeutic agent (the "control sample") for a predetermined time period (e.g., 2, 4, 8, 16, or 24 hours) and then comparing the amount of unconjugated antibody or derivative thereof or other binding agent or therapeutic agent present in the ADC sample with that present in control sample, as measured, for example, by high performance liquid chromatography.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the antibody or derivative thereof or other binding agent (i.e., in the milieu of the ADC or ADC derivative as described herein).

A variety of linkers that can be used with the present compositions and methods are described in WO 2004010957 entitled "Drug Conjugates and Their Use for Treating Cancer, An Autoimmune Disease or an Infectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

In certain embodiments, the linker unit has the following general formula:

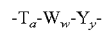

wherein:
-T- is a stretcher unit;
a is 0 or 1;
each -W- is independently an amino acid unit;
w is independently an integer ranging from 0 to 12;
-Y- is a spacer unit; and
y is 0, 1 or 2.

1. The Stretcher Unit

The stretcher unit (-T-), when present, links the antibody or derivative thereof or other binding agent unit to an amino acid unit (-W-). Useful functional groups that can be present on a target antigen binding antibody, either naturally or via chemical manipulation include, but are not limited to, sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of an antibody or derivative thereof or other binding agent. Alternatively, sulfhydryl groups can be generated by reaction of an amino group of a lysine moiety of an antibody or derivative thereof or other binding agent with 2-iminothiolane (Traut's reagent) or other sulfhydryl generating reagents. In specific embodiments, the antibody or derivative thereof or other binding agent is a recombinant antibody or derivative thereof or other binding agent and is engineered to carry one or more lysines. In other embodiments, the recombinant antibody or derivative thereof or other binding agent is engineered to carry additional sulfhydryl groups, e.g., additional cysteines.

In certain specific embodiments, the stretcher unit forms a bond with a sulfur atom of the antibody or derivative thereof or other binding agent unit. The sulfur atom can be derived from a sulfhydryl (—SH) group of a reduced antibody or derivative thereof or other binding agent (A). Representative stretcher units of these embodiments are depicted within the square brackets of Formulas (Ia) and (Ib; see infra), wherein A-, -W-, -Y-, -D, w and y are as defined above and $R^1$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1-10.

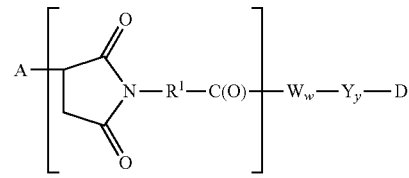

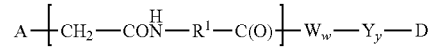

An illustrative stretcher unit is that of formula (Ia) where $R^1$ is —$(CH_2)_5$—:

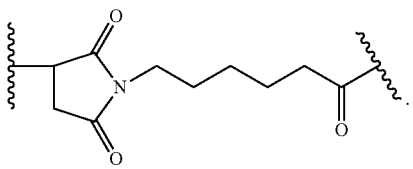 [SMILES: *C(=O)CCCCCN1C(=O)CC(*)C1=O]

Another illustrative stretcher unit is that of formula (Ia) where $R^1$ is —$(CH_2CH_2O)_r$—$CH_2$— and r is 2:

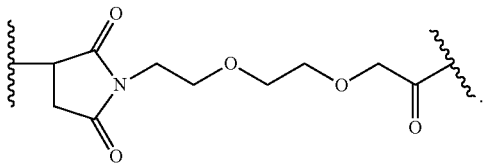 [SMILES: *C(=O)COCCOCCN1C(=O)CC(*)C1=O]

Still another illustrative stretcher unit is that of formula (Ib) where $R^1$ is —$(CH_2)_5$—:

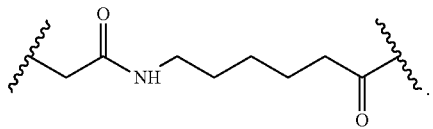 [SMILES: *CC(=O)NCCCCCC(*)=O]

In certain other specific embodiments, the stretcher unit is linked to the antibody or derivative thereof or other binding agent unit (A) via a disulfide bond between a sulfur atom of the antibody or derivative thereof or other binding agent unit and a sulfur atom of the stretcher unit. A representative stretcher unit of this embodiment is depicted within the square brackets of Formula (II), wherein $R^1$, A-, -W-, -Y-, -D, w and y are as defined above.

$$A\text{—}[S\text{-}R^1\text{—}C(O)]\text{—}W_w\text{-}Y_y\text{-}D \quad (II)$$

In other specific embodiments, the reactive group of the stretcher contains a reactive site that can be reactive to an amino group of an antibody or derivative thereof or other binding agent. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates. Representative stretcher units of these embodiments are depicted within the square brackets of Formulas (IIIa) and (IIIb), wherein $R^1$, A-, -W-, -Y-, -D, w and y are as defined above;

In yet another aspect, the reactive function of the stretcher contains a reactive site that is reactive to a modified carbohydrate group that can be present on an antibody or derivative thereof or other binding agent. In a specific embodiment, the antibody or derivative thereof or other binding agent is glycosylated enzymatically to provide a carbohydrate moiety. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, and an arylhydrazide such as those described by Kaneko et al., 1991, *Bioconjugate Chem* 2:133-41. Representative stretcher units of this embodiment are depicted within the square brackets of Formulas (IVa)-(IVc), wherein $R^1$, A-, -W-, -Y-, -D, w and y are as defined above.

 (IVa)

 (IVb)

 (IVc)

2. The Amino Acid Unit

The amino acid unit (-W-) links the stretcher unit (-T-) to the Spacer unit (-Y-) if the Spacer unit is present, and links the stretcher unit to the cytotoxic or cytostatic agent (Drug unit; D) if the spacer unit is absent.

-$W_w$- is a dipeptide, tripeptide, tetrapeptide, pentapeptide, hexapeptide, heptapeptide, octapeptide, nonapeptide, decapeptide, undecapeptide or dodecapeptide unit. Each -W- unit independently has the formula denoted below in the square brackets, and w is an integer ranging from 2 to 12:

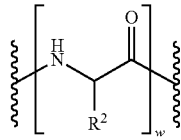

wherein $R^2$ is hydrogen, methyl, isopropyl, isobutyl, sec-butyl, benzyl, p-hydroxybenzyl, —$CH_2OH$, —$CH(OH)CH3$, —$CH_2CH_2SCH3$, —$CH_2CONH2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

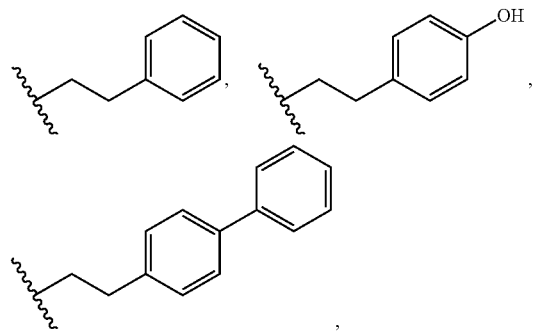

-continued

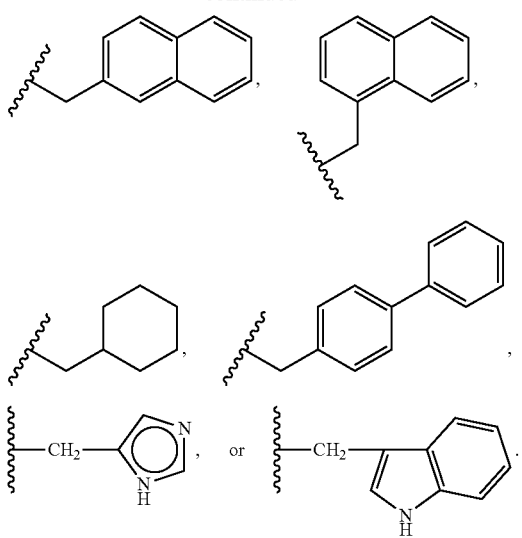

The amino acid unit of the linker unit can be enzymatically cleaved by an enzyme including, but not limited to, a tumor-associated protease to liberate the drug unit (-D) which is protonated in vivo upon release to provide a cytotoxic drug (D).

Illustrative $W_w$ units are represented by formulas (V)-(VII):

(V)

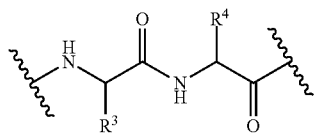

wherein $R^3$ and $R^4$ are as follows:

| $R^3$ | $R^4$ |
| --- | --- |
| Benzyl | $(CH_2)_4NH_2$; |
| Methyl | $(CH_2)_4NH_2$; |
| Isopropyl | $(CH_2)_4NH_2$; |
| Isopropyl | $(CH_2)_3NHCONH_2$; |
| Benzyl | $(CH_2)_3NHCONH_2$; |
| Isobutyl | $(CH_2)_3NHCONH_2$; |
| sec-butyl | $(CH_2)_3NHCONH_2$; |
| (indole-CH₂) | $(CH_2)_3NHCONH_2$; |
| Benzyl | methyl; and |
| Benzyl | $(CH_2)_3NHC(=NH)NH_2$. |

(VI)

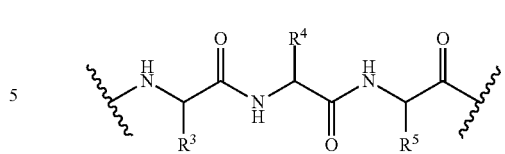

wherein $R^3$, $R^4$ and $R^5$ are as follows:

| $R^3$ | $R^4$ | $R^5$ |
| --- | --- | --- |
| Benzyl | benzyl | $(CH_2)_4NH_2$; |
| Isopropyl | benzyl | $(CH_2)_4NH_2$; and |
| H | benzyl | $(CH_2)_4NH_2$; |

(VII)

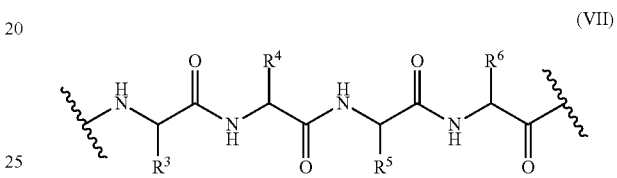

wherein $R^3$, $R^4$, $R^5$ and $R^6$ are as follows:

| $R^3$ | $R^4$ | $R^5$ | $R^6$ |
| --- | --- | --- | --- |
| H | Benzyl | isobutyl | H; and |
| methyl | Isobutyl | methyl | isobutyl. |

Suitable amino acid units include, but are not limited to, units of formula (V) where: $R^3$ is benzyl and $R^4$ is —$(CH_2)_4NH_2$; $R^3$ is isopropyl and $R^4$ is —$(CH_2)_4NH_2$; or $R^3$ is isopropyl and $R^4$ is —$(CH_2)_3NHCONH_2$. Another suitable amino acid unit is a unit of formula (VI), where: $R^3$ is benzyl, $R^4$ is benzyl, and $R^5$ is —$(CH_2)_4NH_2$.

-$W_w$- units can be designed and optimized in their selectivity for enzymatic cleavage by a particular tumor-associated protease. The suitable -Ww- units are those whose cleavage is catalyzed by the proteases, cathepsin B, C and D, and plasmin.

In one embodiment, -$W_w$- is a dipeptide, tripeptide or tetrapeptide unit.

Where $R^2$, $R^3$, $R^4$, $R^5$ or $R^6$ is other than hydrogen, the carbon atom to which $R^2$, $R^3$, $R^4$, $R^5$ or $R^6$ is attached is chiral.

Each carbon atom to which $R^2$, $R^3$, $R^4$, $R^5$ or $R^6$ is attached is independently in the (S) or (R) configuration.

In a certain embodiment, the amino acid unit is a phenylalanine-lysine dipeptide (Phe-Lys or FK linker). In another embodiment, the amino acid unit is a valine-citrulline dipeptide (Val-Cit or VC linker).

3. The Spacer Unit

The spacer unit (-Y-), when present, links an amino acid unit to the drug unit. Spacer units are of two general types: self-immolative and non-self-immolative. A non-self-immolative spacer unit is one in which part or all of the spacer unit remains bound to the drug unit after enzymatic cleavage of an amino acid unit from the antibody-linker-drug conjugate or the drug-linker compound. Examples of a non-self-immolative spacer unit include, but are not limited to a (glycine-glycine) spacer unit and a glycine spacer unit (both depicted in Scheme 1). When an antibody-linker-drug conjugate containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from A-T-$W_w$-. To liberate the drug, an independent hydrolysis reaction should take place within the target cell to cleave the glycine-drug unit bond.

In a typical embodiment, -$Y_y$- is a p-aminobenzyl ether which can be substituted with $Q_m$ where Q is —$C_1$-$C_8$ alkyl, —$C_1$-$C_8$ alkoxy, -halogen, -nitro or -cyano; and m is an integer ranging from 0-4.

Scheme 1

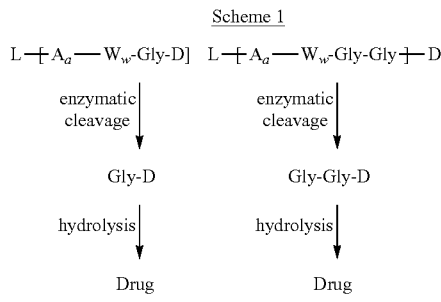

In one embodiment, a non-self-immolative spacer unit (-Y-) is -Gly-Gly-.

In another embodiment, a non-self-immolative the spacer unit (-Y-) is -Gly-.

In one embodiment, the drug-linker compound or an anti-CD70 antibody-linker-drug conjugate lacks a spacer unit (y=0).

Alternatively, an antibody or derivative thereof or other binding agent-linker-drug conjugate containing a self-immolative spacer unit can release the drug (D) without the need for a separate hydrolysis step. In these embodiments, -Y- is a p-aminobenzyl alcohol (PAB) unit that is linked to -$W_w$- via the nitrogen atom of the PAB group, and connected directly to -D via a carbonate, carbamate or ether group (Scheme 2 and Scheme 3).

Scheme 2

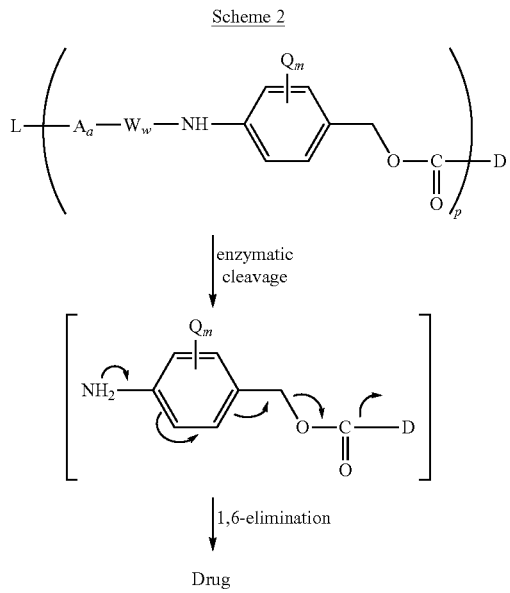

where Q is —$C_1$-$C_8$ alkyl, —$C_1$-$C_8$ alkoxy, -halogen, -nitro or -cyano; m is an integer ranging from 0-4; and p is an integer ranging from 1-20.

Scheme 3

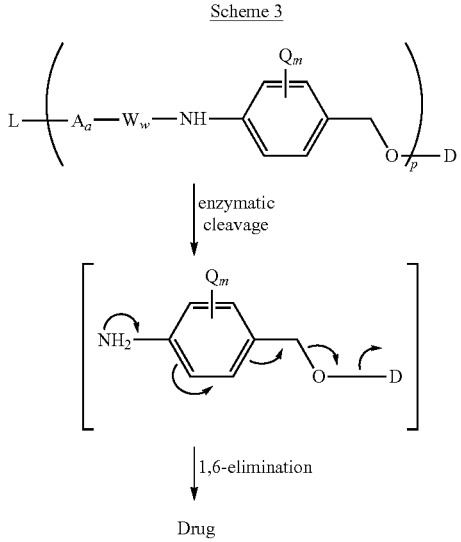

where Q is —$C_1$-$C_8$ alkyl, —$C_1$-$C_8$ alkoxy, -halogen, -nitro or -cyano; m is an integer ranging from 0-4; and p is an integer ranging from 1-20.

Other examples of self-immolative spacers include, but are not limited to, aromatic compounds that are electronically equivalent to the PAB group such as 2-aminoimidazol-5-methanol derivatives (see Hay et al., 1999, *Bioorg. Med. Chem. Lett.* 9:2237 for examples) and ortho- or para-aminobenzylacetals. Spacers can be used that undergo facile cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenyl-propionic acid amides (Amsberry et al., 1990, *J. Org. Chem.* 55:5867). Elimination of amine-containing drugs that are substituted at the α-position of glycine (Kingsbury, et al., 1984, *J. Med. Chem.* 27:1447) are also examples of self-immolative spacer strategies that can be applied to the antibody-linker-drug conjugates.

In an alternate embodiment, the spacer unit is a branched bis(hydroxymethyl)styrene (BHMS) unit (Scheme 4), which can be used to incorporate additional drugs.

Scheme 4

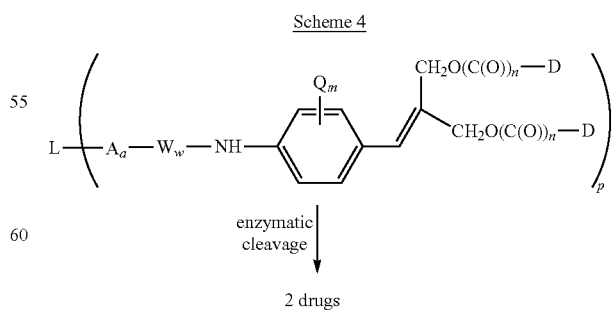

where Q is —$C_1$-$C_8$ alkyl, —$C_1$-$C_8$ alkoxy, -halogen, -nitro or -cyano; m is an integer ranging from 0-4; n is 0 or 1; and p is an integer ranging from 1-20.

In one embodiment, the two -D moieties are the same.

In another embodiment, the two -D moieties are different.

Typical spacer units (-$Y_y$-) are represented by Formulas (VIII)-(X):

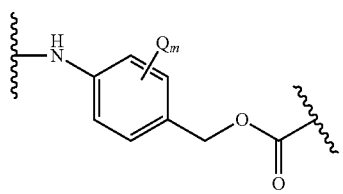

(VIII)

where Q is $C_1$-$C_8$ alkyl, $C_1$-$C_8$ alkoxy, halogen, nitro or cyano; and m is an integer ranging from 0-4;

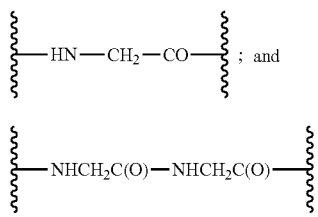

(IX)

(X)

B. Therapeutic Agents

In accordance with the methods described herein, any agent that exerts a therapeutic effect on cancer cells or activated immune cells can be used as the therapeutic agent for conjugation to an antibody or derivative thereof or other binding agent. (See, e.g., WO 2004/010957, "Drug Conjugates and Their Use for Treating Cancer, An Autoimmune Disease or an Infectious Disease" (supra) and U.S. Provisional Application No. 60/400,403 (supra)). Typically, the therapeutic agent is a cytotoxic or immunosuppressinve agent.

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the antibodies or derivatives thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. patent application Ser. No. 09/845,786 (U.S. Patent Application Publication No. 20030083263) and Ser. No. 10/001,191; International Patent Application No. PCT/US03/24209, International Patent Application No. PCT/US02/13435, and U.S. Pat. Nos. 6,323, 315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130, 237.) For example, in certain embodiments, the minor groove binding agent is a CBI compound. In other embodiments, the minor groove binding agent is an enediyne (e.g., calicheamicin).

In certain embodiments, the ADC or ADC derivative comprises an anti-tubulin agent. Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In certain embodiments, the therapeutic agent is not a radioisotope.

In certain embodiments, the cytotoxic or immunomodulatory agent is an antimetabolite. The antimetabolite can be, for example, a purine antagonist (e.g. azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In additional embodiments, the drug is a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (MedImmune, Inc., MD; Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); and CEAcide (Immunomedics, NJ; a humanized anti-CEA antibody).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen, IL-2 receptor, CD20, CD52, CD33, CD22, human chorionic gonadotropin, CD38, CD40, mucin, P21, MPG, and Neu oncogene product.

In certain embodiments, the therapeutic agent is an immunomodulatory agent. The immunomodulatory agent can be, for example, gancyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In certain typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl)sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

1. Dolastatin Drugs

In certain embodiments, the cytotoxic or cytostatic agent is a dolastatin. In more specific embodiments, the dolastatin is of the auristatin class. As used herein, the term dolastatin encompasses naturally occurring auristatins and non-naturally occurring derivatives, for example MMAE. Thus, in a specific embodiment, the cytotoxic or cytostatic agent is MMAE (Formula XI). In another specific embodiment, the cytotoxic or cytostatic agent is AFP (Formula XVI).

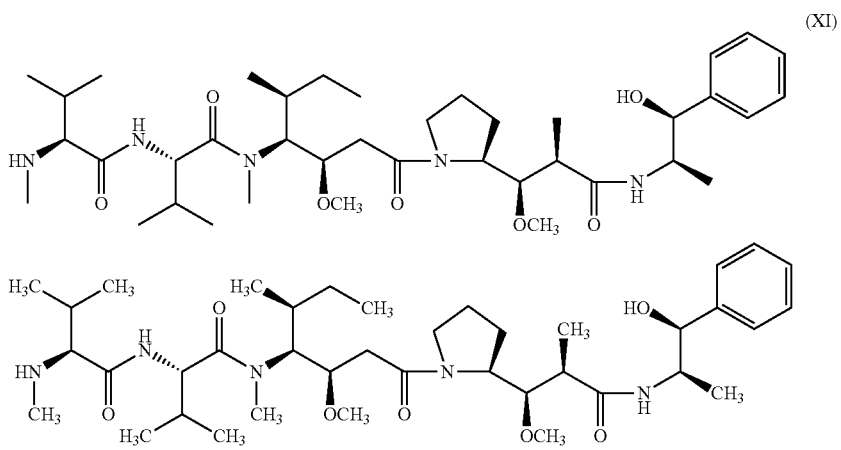
(XI)
In certain embodiments, the cytotoxic or cytostatic agent is a dolastatin of formulas XII-XXI.
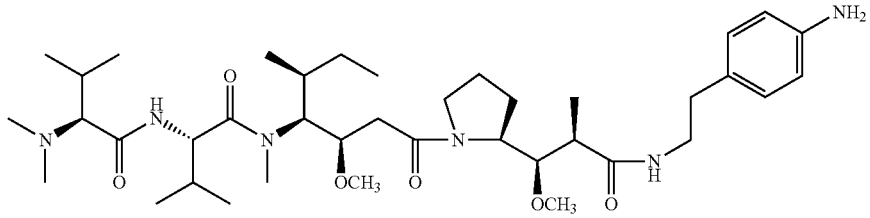
(XII)
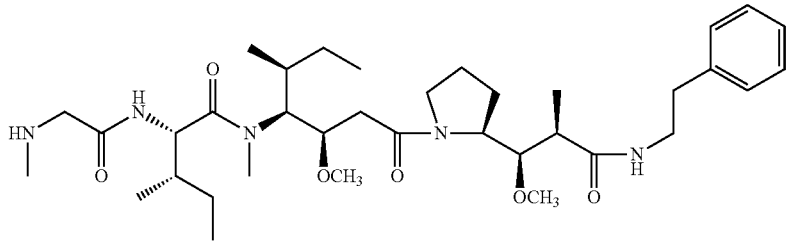
(XIII)
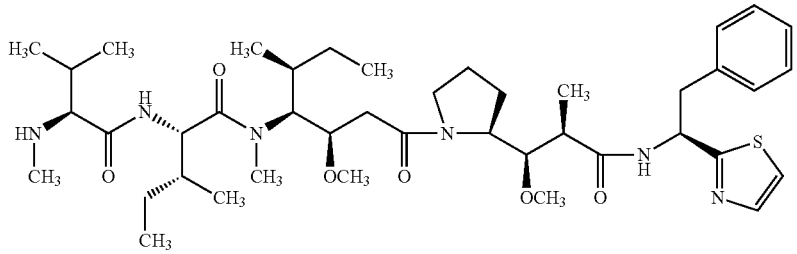
(XIV)
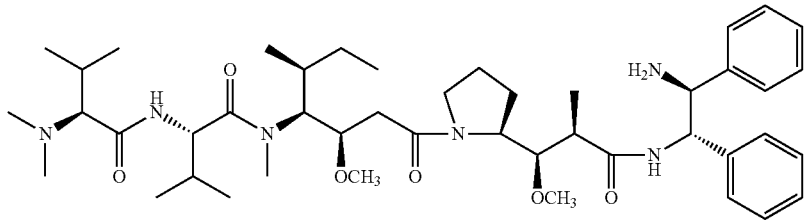
(XV)

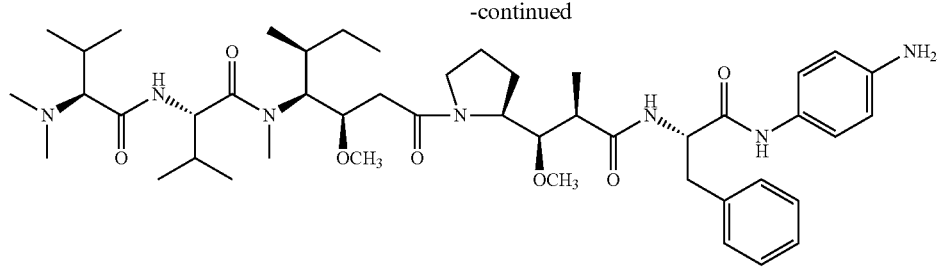
(XVI)
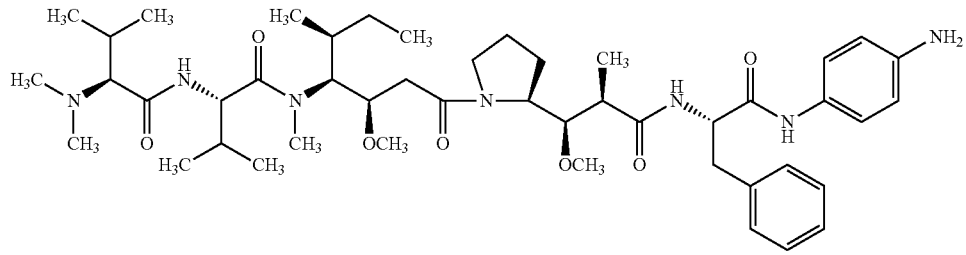
(XVII)
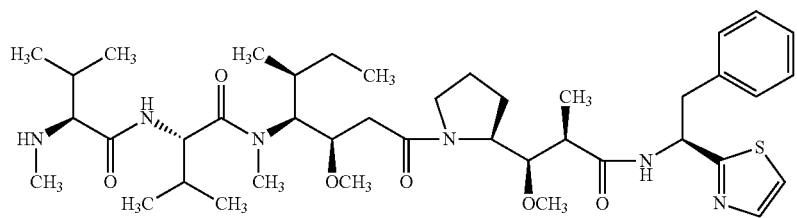
(XVIII)
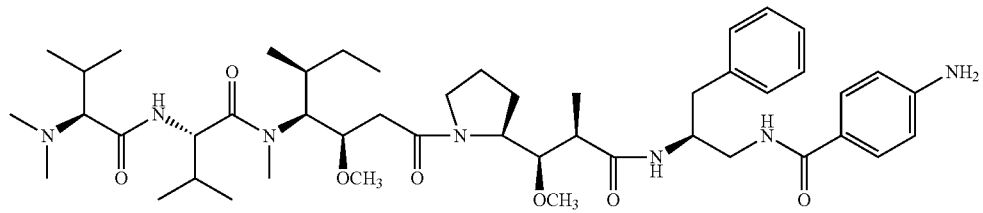
(XVIV)
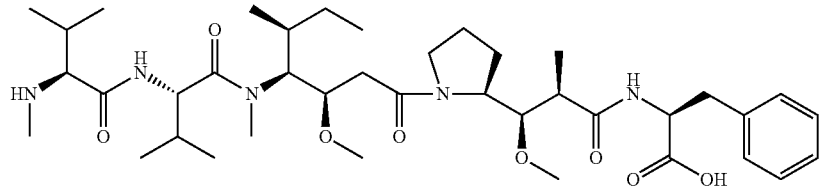
(XX)
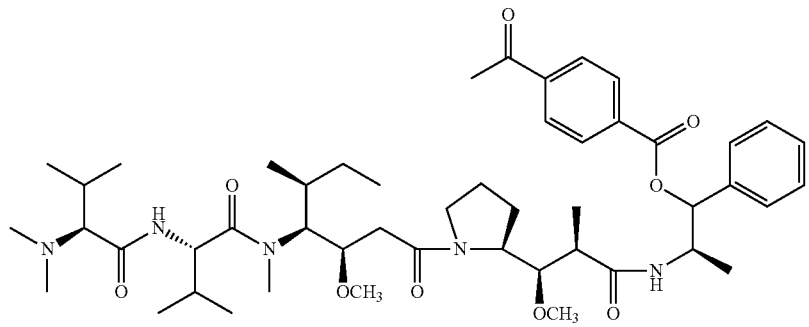

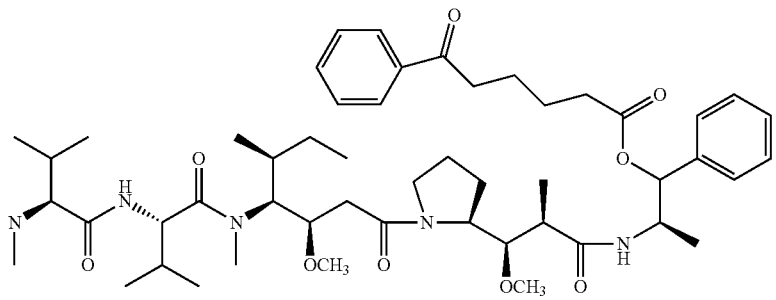

(XXI)

C. Formation of ADCs and ADC Derivatives

The generation of ADCs and ADC derivatives can be accomplished by any technique known to the skilled artisan. Briefly, the ADCs comprise an antibody or derivative thereof or other binding agent, a drug, and optionally a linker that joins the drug and the antibody or derivative thereof or other binding agent. A number of different reactions are available for covalent attachment of drugs to antibodies or derivatives thereof or other binding agents. This is often accomplished by reaction of the amino acid residues of the molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody or derivative thereof or other binding agent. Additionally, bifunctional agents such as dialdehydes or imidoesters have been used to link the amino group of a compound to amino groups of the molecule. Also available for attachment of drugs to antibodies is the Schiff base reaction. This method involves the periodate oxidation of a drug that contains glycol or hydroxy groups, thus forming an aldehyde which is then reacted with the antibody or derivative thereof or other binding agent. Attachment occurs via formation of a Schiff base with amino groups of the molecule. Isothiocyanates can also be used as coupling agents for covalently attaching drugs to antibodies or derivatives thereof or other binding agents. Other techniques are known to the skilled artisan and within the scope of the present invention. Non-limiting examples of such techniques are described in, e.g., U.S. Pat. Nos. 5,665,358; 5,643,573; and 5,556,623, which are incorporated by reference in their entireties herein.

In some embodiments a binding region (such as an antibody) is conjugated to a linker-drug conjugate as disclosed in Published U.S. Application Nos. 2006-0074008 or 2005-0238649 or Published International Application No. WO 05/084390. In some embodiments, where a cysteine residue in introduced, a binding region can be conjugated to a linker drug conjugate as disclosed in Published U.S. Patent Application No. 2007-092940 or Givol et al., 1965, *Proc. Natl. Acad. Sci.* USA 53:676-84. Generally, the interchain disulfide bonds, and the introduced cysteine residue(s) of the antibody are fully reduced, followed by partial reoxidation of the interchain disulfides (e.g., with copper, air or dehydroascorbic acid). The linker drug is then be conjugated to the introduced cysteine residues.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the antibody or derivative thereof or other binding agent under appropriate conditions.

V. Methods to Modify Antibodies and Binding Agents

Target binding antibodies or derivatives thereof or other target binding agents can also include analogs and derivatives that are modified, e.g., by deletions from, and/or insertions into and/or substitutions of, residues within the amino acid sequences of the antibody or binding agent, or by covalent attachment of any type of molecule as long as such covalent attachment permits the antibody to retain its antigen-binding immunospecificity.

For example, the derivatives and analogs of the antibodies or derivatives thereof or other binding agents include those that have been further modified, e.g., by glycosylation, deglycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, or the like. Additionally, the analog or derivative can contain one or more unnatural amino acids.

In specific embodiments, it may be desirable to improve the binding affinity and/or other biological properties of the antibody or derivative thereof or other binding agent. (See, e.g., U.S. Patent Publication Nos. 2006/0003412 and 2006/0008882.) Amino acid sequence derivatives of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody or derivative thereof or other binding agent that are favored locations for mutagenesis is called "alanine scanning mutagenesis" as described by Cunningham and Wells, 1989, *Science* 244:1081-1085. Here, a residue or group of target residues are identified (e.g., charged residues such as arg, asp, his, lys, and glu) and replaced by a neutral or negatively charged amino acid (typically alanine or polyalanine) to affect the interaction of the amino acids with antigen. Those amino acid locations demonstrating functional sensitivity to the substitutions then are refined by introducing further or other derivatives at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody derivatives are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody or derivative thereof or other binding agent with an N-terminal methionyl residue or the antibody or derivative thereof or other binding agent fused to a cytotoxic polypeptide.

Another type of derivative is an amino acid substitution derivative. These derivatives have at least one amino acid residue in the antibody or derivative thereof or other binding agent replaced by a different residue. The sites of greatest interest for substitutional mutagenesis include the hypervariable regions, but framework region alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative amino acid substitutions will entail exchanging a member of one of these classes for another class.

A particular type of substitutional derivative involves substituting one or more hypervariable region residues of a parent antibody (e.g., a humanized or human antibody). Generally, the resulting derivative(s) selected for further development will have improved biological properties relative to the parent antibody from which they are generated. A convenient way for generating such substitutional derivatives involves affinity maturation using phage display. Briefly, several hypervariable region sites (e.g., 6-7 sites) are mutated to generate all possible amino substitutions at each site. The antibody derivatives thus generated are displayed in a monovalent fashion from filamentous phage particles as fusions to the gene III product of M13 packaged within each particle. The phage-displayed derivatives are then screened for their biological activity (e.g., binding affinity). In order to identify candidate hypervariable region sites for modification, alanine scanning mutagenesis can be performed to identify hypervariable region residues contributing significantly to antigen-binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such derivatives are generated, the panel of derivatives is subjected to screening and antibodies with superior properties in one or more relevant assays may be selected for further development.

It may be desirable to modify the antibody or derivative thereof or other binding agent with respect to binding to one or more Fc gamma (Fcγ) receptors (FcγR), e.g., so as to reduce binding to one or more FcγR. Such modification may also result in reduced antibody-dependent cell-mediated cyotoxicity (ADCC), antibody-dependent cellular phagocytosis (ADCP), and/or complement dependent cytotoxicity (CDC) of the antibody. This modification may be achieved by introducing one or more amino acid substitutions (e.g., non-conservative amino acid substitutions) in or in proximity to an Fc region of the antibody or derivative thereof or other binding agent. Alternatively or additionally, cysteine residue(s) may be introduced in or in proximity to the Fc region, thereby allowing interchain disulfide bond formation in this region. Alternatively or additionally, one or more N-linked glycosylation sites may be introduced in or in proximity to the Fc region, thereby allowing post-translational glycosylation in this region, as described supra. The homodimeric antibody or derivative thereof or other binding agent thus generated may have impaired ability to bind to Fc gamma receptors. The homodimeric antibody thus generated may also have impaired internalization capability and/or decreased ADCC, ADCP and/or CDC responses.

In some embodiments, the amino acid substitution affects the binding interaction of the Fc region with the FcγRIIIa receptor. In some embodiments, the amino acid substitution of the native amino acid to a cysteine residue is introduced at amino acid position 239, 265, 269 or 327. In some embodiments, the amino acid substitution of the native amino acid to a cysteine residue is introduced at amino acid position 239 or 269. In some embodiments, the amino acid substitution of the native amino acid to a cysteine residue is introduced at amino acid position 239. In some embodiments, the amino acid substitution of the native amino acid to a cysteine residue is introduced at amino acid position 265. In some embodiments, the amino acid substitution of the native amino acid to a cysteine residue is introduced at amino acid position 269. In some embodiments, the amino acid substitution of the native amino acid to a cysteine residue is introduced at amino acid position 327.

In other embodiments, the amino acid substitution of the native amino acid to a cysteine residue is introduced at amino acid position 236 or 238. In some embodiments, the amino acid substitution of the native amino acid to a cysteine residue is introduced at amino acid position 236. In some embodiments, the amino acid substitution of the native amino acid to a cysteine residue is introduced at amino acid position 238.

In other embodiments, the amino acid substitution of the native amino acid to a cysteine residue is introduced at amino acid position 234, 235, 237, 267, 298, 299, 326, 330, or 332. In other embodiments, the amino acid substitution of the native amino acid to a cysteine residue is introduced at amino acid position 237, 298, 299, 326, 330, or 332. In other embodiments, the amino acid substitution of the native amino acid to a cysteine residue is introduced at amino acid position 298, 299, 326 or 330. In some embodiments, the amino acid substitution of the native amino acid to a cysteine residue is introduced at amino acid position 234. In some embodiments, the amino acid substitution of the native amino acid to a cysteine residue is introduced at amino acid position 235. In some embodiments, the amino acid substitution of the native amino acid to a cysteine residue is introduced at amino acid position 237. In some embodiments, the amino acid substitution of the native amino acid to a cysteine residue is introduced at amino acid position 267. In some embodiments, the amino acid substitution of the native amino acid to a cysteine residue is introduced at amino acid position 298. In some embodiments, the amino acid substitution of the native amino acid to a cysteine residue is introduced at amino acid position 299. In some embodiments, the amino acid substitution of the native amino acid to a cysteine residue is introduced at amino acid position 326. In some embodiments, the amino acid substitution of the native amino acid to a cysteine residue is introduced at amino acid position 330. In some embodiments, the amino acid substitution of the native amino acid to a cysteine residue is introduced at amino acid position 332.

In some embodiments, to further increase the serum half-life of the antibody or derivative thereof or other binding agent, one may modify any salvage receptor binding epitope in the antibody or derivative thereof or other binding agent as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, the serum half-life of the antibody or derivative thereof or other binding agent may be increased by modifying the Fc region of an antibody (e.g., IgG constant domain) with respect to binding to Fc gamma (Fcγ) receptors, as described infra.

Antibodies may be glycosylated at conserved positions in their constant regions (see, e.g., Jeferis and Lund, 1997, *Chem. Immunol.* 65:111-128; Wright and Morrison, 1997, *TibTECH* 15:26-32). The oligosaccharide side chains of the immunoglobulins can affect the protein's function (see, e.g., Boyd et al., 1996, *Mol. Immunol.* 32:1311-1318; Wittwe and Howard, 1990, *Biochem.* 29:4175-4180), and the intramolecular interaction between portions of the glycoprotein which can affect the conformation and presented three-dimensional surface of the glycoprotein (see, e.g., Jefferis and Lund, supra; Wyss and Wagner, 1996, *Current Opin. Biotech.* 7:409-416). Oligosaccharides may also serve to target a given glycoprotein to certain molecules based upon specific recognition structures. For example, it has been reported that in agalactosylated IgG, the oligosaccharide moiety 'flips' out of the inter-$C_H2$ space and terminal N-acetylglucosamine residues become available to bind mannose binding protein (see, e.g., Malhotra et al., 1995, *Nature Med.* 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., 1996, *Mol. Immunol.* 32:1311-1318), while selective removal of sialic acid residues using neuraminidase resulted in no loss of DMCL. Glycosylation of antibodies has also been reported to affect ADCC. In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (see, e.g., Umana et al., 1999, *Mature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Glycosylation derivatives of antibodies are derivatives in which the glycosylation pattern of an antibody is altered. By altering is meant deleting one or more carbohydrate moieties found in the antibody, adding one or more carbohydrate moieties to the antibody, changing the composition of glycosylation (i.e., glycosylation pattern), the extent of glycosylation, or the like.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence derivatives) or preparation by oligonucleotide-mediated (or site-directed) mutagenesis, PCR mutagenesis, or cassette mutagenesis of an earlier prepared derivative or a non-derivative version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., 1997, *J. Biol. Chem.* 272:9062-9070. In addition to the choice of host cells, factors which affect glycosylation during recombinant production of antibodies include growth mode, media formulation, culture density, oxygenation, pH, purification schemes, and the like. Various methods have been proposed to alter the glycosylation pattern achieved in a particular host organism, including introducing or overexpressing certain enzymes involved in oligosaccharide production (see, e.g., U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered, e.g., made defective in processing certain types of polysaccharides. These and similar techniques are well known in the art.

The glycosylation structure of antibodies can be readily analyzed by conventional techniques of carbohydrate analysis, including lectin chromatography, NMR, mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

The antibodies or derivatives thereof or other binding agents can have modifications (e.g., substitutions, deletions or additions) in amino acid residues that interact with Fcγ receptors. In particular, antibodies or derivatives thereof or other binding agents include antibodies or derivatives thereof or other binding agents having modifications in amino acid residues identified as involved in the binding interaction between the Fc domain and one or more Fcγ receptors (see infra), as well as antibodies or derivatives thereof or other binding agents having modifications in amino acid residues identified as involved in the interaction between the anti-Fc domain and the FcRn receptor (see, e.g., International Publication No. WO 97/34631, which is incorporated herein by reference in its entirety).

VI. Methods to Alter Binding of Target Binding Agents To Fcγ Receptors

In some embodiments, the binding of a target binding agent to one or more Fcγ receptors can be impaired using one or more antibody engineering approaches known in the art. In some embodiments, the binding of a target binding agent to one or more Fcγ receptors can be impaired by reducing the target binding agent's effector functions using one or more antibody engineering approaches known in the art. Illustrative, non-limiting examples for such approaches are provided below.

Fcγ receptor binding is mediated through the interaction of a region of an antibody with an Fc gamma (Fcγ) receptor (Fc*). The Fc region or domain refers to the region(s) of an antibody constant region (e.g., IgG1, IgG2, IgG3, or IgG4) that is involved in the binding interaction of the Fc region to one or more Fcγ receptors (e.g., FcγRI (CD64), FcγRIIb (CD32b) or FcγRIIIa (CD16). Both the glycosylation status and primary amino acid sequence of the IgG Fc region have functional effects on the Fc region-FcγR interaction.

Substitution of particular amino acid positions in the Fc region of IgG isotype constant regions are known to have functional effects on the ability of an antibody to bind to one or more Fcγ receptors. See, e.g., Shields et al., 2001, *J. Biol. Chem.* 276:6591-6604, and Canfield and Morrison, 1991, *J. Exp. Med.* 173:1483-1491. The Fc region includes, for example and not for limitation, amino acid residues in the hinge region and the $C_H2$ domain. Substitution of one or more amino acid residues in the Fc region or portion of an IgG constant region with non-conservative amino acids can be expected to alter, i.e., reduce the affinity of the Fc region-FcγR interaction. Methods for introducing non-conservative amino acid substitutions in an antibody or derivative thereof or other binding agent are well known in the art.

Alternatively or additionally, cysteine residue(s) may be introduced in or in proximity to the Fc region or portion of an IgG constant region, thereby allowing interchain disulfide bond formation in this region. Such interchain disulfide bond formation can be expected to cause steric hindrance, thereby reducing the affinity of the Fc region-FcγR binding interaction. The cysteine residue(s) introduced in or in proximity to the Fc region of an IgG constant region may also serve as sites for conjugation to therapeutic agents (i.e., coupling cytotoxic drugs using thiol specific reagents such as maleimide derivatives of drugs. The presence of a therapeutic agent can be expected to cause steric hindrance, thereby reducing the affinity of the Fc region-FcγR binding interaction. Methods for introducing cysteine residues in an antibody or derivative thereof or other binding agent are well known in the art.

Alternatively or additionally, one or more N-linked glycosylation sites may be introduced in or in proximity to the Fc region of an IgG constant region, thereby allowing post-translational glycosylation in this region. Such N-linked glycosylation can be expected to cause steric hindrance, thereby reducing the affinity of the Fc region-FcγR binding interaction. Methods for introducing N-linked glycosylation sites in an antibody or derivative thereof or other binding agent are well known in the art.

A systemic substitution of solvent-exposed amino acids of human IgG1 Fc region has generated IgG derivatives with altered FcγR binding affinities (Shields et al., 2001, *J. Biol. Chem.* 276:6591-604). For example, when compared to parental IgG1, a subset of these derivatives involving substitutions at Thr256/Ser298, Ser298/Glu333, Ser298/Lys334, or Ser298/Glu333/Lys334 to Ala demonstrate increases in both binding affinity toward FcγR and ADCC activity (Shields et al., 2001, *J. Biol. Chem.* 276:6591-604; Okazaki et al., 2004, *J. Mol. Biol.* 336:1239-49). In contrast, when compared to parental IgG1, a subset of these derivatives involving substitutions at Glu233 to Pro/Leu234 to Val/Leu235 to Ala and Gly 236 deletion, Pro238 to Ala, Asp265 to Ala, Asn297 to Ala, Ala 327 to Gln, or Pro329 to Ala demonstrate decreases in binding affinities to all FcγR; the Asp265 to Ala substitution also resulted in decreased ADCC activity (Shields et al., 2001, *J. Biol. Chem.* 276:6591-604) Amino acids in the hinge region and the $C_H2$ domain have been shown to contribute to high affinity of human IgG for FcγR (Canfield and Morrison, 1991, *J. Exp. Med.* 173:1483-1491). These amino acid positions, or amino acids in proximity thereto, involved in mediating the Fc region-FcγR binding interaction are potential targets for replacement by non-conservative amino acids and/or introduction of one or more cysteines, and/or introduction of one or more N-linked glycosylation sites.

The in vivo half-life of an antibody can also impact on its effector functions. In some embodiments, it is desirable to increase the half-life of an antibody to modify its therapeutic activities. In some embodiments, it is desirable to decrease the half-life of an antibody to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human $IgG_1$ involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human $IgG_1$ enhance FcRn binding (Shields et al., 2001, *J. Biol. Chem.* 276:6591-604). $IgG_1$ molecules harboring these substitutions are expected to have longer serum half-lives. Consequently, these modified $IgG_1$ molecules may be able to carry out their effector functions, and hence exert their therapeutic efficacies, over a longer period of time compared to unmodified $IgG_1$.

In an embodiment, the variant target binding agents, which have impaired binding to one or more FcγR retain, at least to some extent, the ability to bind FcRn. In an exemplary embodiment, the variant target binding agents, which have impaired binding to one or more FcγR, retain the ability to bind FcRn. The ability of an antibody or derivative thereof or other binding agent to bind to FcRn can be measured by techniques known in the art (e.g., Shields et al., 2001, *J. Biol. Chem.* 276:6591-604). The variant target binding agent binds to FcRn with at least 10%, at least 20%, at least 30%, at least 40%, at least 50%, at least 60%, at least 70%, at least 80% or at least 90% the affinity of a non-variant target binding agent for binding FcRn.

VII. Animal Models of Immunological Disorders or Cancers

The anti-target binding agents, e.g., antibodies or derivatives, can be tested or validated in animal models of immunological disorders or cancers. A number of established animal models of immunological disorders or cancers are known to the skilled artisan, any of which can be used to assay the efficacy of a target binding agent. Non-limiting examples of such models are described infra.

Examples for animal models of systemic and organ-specific autoimmune diseases including diabetes, lupus, systemic sclerosis, Sjögren's Syndrome, experimental autoimmune encephalomyelitis (multiple sclerosis), thyroiditis, myasthenia gravis, arthritis, uveitis, and inflammatory bowel disease have been described by Bigazzi, "Animal Models of Autoimmunity: Spontaneous and Induced," in *The Autoimmune Diseases* (Rose and Mackay eds., Academic Press, 1998) and in "Animal Models for Autoimmune and Inflammatory Disease," in *Current Protocols in Immunology* (Coligan et al. eds., Wiley and Sons, 1997).

Allergic conditions, e.g., asthma and dermatitis, can also be modeled in rodents. Airway hypersensitivity can be induced in mice by ovalbumin (Tomkinson et al., 2001, *J. Immunol.* 166:5792-800) or *Schistosoma mansoni* egg antigen (Tesciuba et al., 2001, *J. Immunol.* 167:1996-2003). The Nc/Nga strain of mice show marked increase in serum IgE and spontaneously develop atopic dermatitis-like lesions (Vestergaard et al., 2000, *Mol. Med. Today* 6:209-10; Watanabe et al., 1997, *Int. Immunol.* 9:461-66; Saskawa et al., 2001, *Int. Arch. Allergy Immunol.* 126:239-47).

Injection of immunocompetent donor lymphocytes into a lethally irradiated histo-incompatible host is a classical approach to induce GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, *Bone Marrow Transpl.* 26:931-938; Kataoka et al., 2001, *Immunology* 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, *Science* 241:1632-1639; Kamel-Reid and Dick, 1988, *Science* 242:1706-1709; Mosier et al., 1988, *Nature* 335:256-259). This has provided a small animal model system for the direct testing of potential therapeutic agents on human lymphoid cells. (See, e.g., Tournoy et al., 2001, *J. Immunol.* 166:6982-6991).

Moreover, small animal models to examine the in vivo efficacies of the target binding agents can be created by implanting target antigen-expressing human tumor cell lines into appropriate immunodeficient rodent strains, e.g., athymic nude mice or SCID mice. Examples of target antigen expressing human lymphoma cell lines include, for example, Daudi (Ghetie et al., 1994, *Blood* 83:1329-36; Ghetie et al., 1990, *Int. J. Cancer* 15:481-85; de Mont et al., 2001, *Cancer Res.* 61:7654-59), HS-Sultan (Cattan and Maung, 1996, *Cancer Chemother. Pharmacol.* 38:548-52; Cattan and Douglas, 1994, *Leuk. Res.* 18:513-22), Raji (Ochakovskaya et al., 2001, *Clin. Cancer Res.* 7:1505-10; Breisto et al., 1999, *Cancer Res.* 59:2944-49), and CA46 (Kreitman et al., 1999, *Int. J. Cancer* 81:148-55). A non-limiting example of a Hodgkin's lymphoma line is L428 (Drexler, 1993, *Leuk. Lymphoma* 9:1-25; Dewan et al., 2005, *Cancer Sci.* 96:466-473). Non-limiting examples of human renal cell carcinoma cell lines include 786-O (Ananth et al., 1999, *Cancer Res.* 59:2210-16; Datta et al., 2001, *Cancer Res.* 61:1768-75), ACHN (Hara et al., 2001, *J. Urol.* 166:2491-94; Miyake et al., 2002, *J. Urol.* 167:2203-08), Caki-1 (Prewett et al., 1998, *Clin. Cancer Res.* 4:2957-66; Shi and Siemann, 2002, *Br. J. Cancer* 87:119-26), and Caki-2 (Zellweger et al., 2001, *Neoplasia* 3:360-67). Non-limiting examples of nasopharyngeal carcinoma cell lines include C15 and C17 (Busson et al., 1988, *Int. J. Cancer* 42:599-606; Bernheim et al., 1993, *Cancer Genet. Cytogenet.* 66:11-5). Non-limiting examples of human glioma cell lines include U373 (Palma et al., 2000, *Br. J. Cancer* 82:480-7) and U87MG (Johns et al., 2002, *Int. J. Cancer* 98:398-408). Non-limiting examples of multiple myeloma cell lines include MM.1S (Greenstein et al., 2003, *Experimental Hematology* 31:271-282) and L363 (Diehl et al., 1978, *Blut* 36:331-338). (See also Drexler and Matsuo, 2000, *Leukemia Research* 24:681-703). These tumor cell lines can be established in immunodeficient rodent hosts either as solid tumor by subcutaneous injections or as disseminated tumors by intravenous injections. Once established within a host, these tumor xenograft models can be applied to evaluate the therapeutic efficacies of the target binding agent as described herein on modulating in vivo tumor growth.

VIII. Disorders

The target binding agents (e.g., antibodies and derivatives or antibodies and derivatives conjugated to therapeutic agents) as described herein are useful for treating or preventing a target antigen-expressing cancer or an immunological disorder characterized by expression of the target antigen by inappropriate activation of immune cells (e.g., lymphocytes or dendritic cells). Such expression of a target antigen can be due to, for example, increased target protein levels on the cells surface and/or altered antigenicity of the expressed antigen. Treatment or prevention of the immunological disorder, according to the methods described herein, is achieved by administering to a subject in need of such treatment or prevention an effective amount of the target binding agent, whereby the agent (i) binds to immune cells (e.g., activated immune cells) that express the target antigen and that are associated with the disease state and (ii) exerts a cytotoxic, cytostatic, or immunomodulatory effect on the immune cells.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology* (William E. Paul ed., Raven Press, N.Y., 3rd ed. 1993).)

Specific examples of such immunological diseases include the following: rheumatoid arthritis, psoriatic arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenström's macroglobulemia, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjörgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In some embodiments, the immunological disorder is a T cell-mediated immunological disorder, such as a T cell disorder in which activated T cells associated with the disorder express the target antigen. Anti-target binding agents (e.g., antibodies or derivatives) can be administered to deplete such T cells. In a specific embodiment, administration of antibodies or derivatives can deplete CD70-expressing activated T cells, while resting T cells are not substantially depleted by the anti-CD70 or derivative. In this context, "not substantially depleted" means that less than about 60%, or less than about 70% or less than about 80% of resting T cells are not depleted.

The target binding agents (e.g., antibodies and derivatives or antibodies and derivatives conjugated to therapeutic agents) are also useful for treating or preventing a target antigen-expressing cancer. Treatment or prevention of a cancer, according to the methods described herein, is achieved by administering to a subject in need of such treatment or prevention an effective amount of the target binding agent, whereby the antibody or derivative (i) binds to the target antigen-expressing cancer cells and (ii) exerts a cytotoxic or cytostatic effect to deplete or inhibit the proliferation of the target antigen-expressing cancer cells. The cytotoxic, cytostatic, or immunomodulatory is exerted by conjugation to a cytotoxic, cytostatic, or immunomodulatory agent.

Cancers that can be treated by using a target binding agent include malignancies and related disorders, such as the following: a Leukemia, such as an acute leukemia, such as acute lymphocytic leukemia or acute myelocytic leukemia (myeloblastic, promyelocytic, myelomonocytic, monocytic or erythroleukemia) or a chronic leukemia, such as chronic myelocytic (granulocytic) leukemia or chronic lymphocytic leukemia; polycythemia vera; a Lymphoma, such as Hodgkin's disease or non-Hodgkin's disease (lymphoma); multiple myeloma; Waldenström's macroglobulemia; heavy chain disease; or a solid tumor, such as sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma.

CD70-expressing cancers that can be treated or prevented by the methods described herein include, for example, different subtypes of Non-Hodgkin's Lymphoma (indolent NHLs, follicular NHLs, small lymphocytic lymphomas, lymphoplasmacytic NHLs, or marginal zone NHLs); Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenström's macroglobulemia; multiple myelomas; and colon, stomach, and rectal carcinomas. The cancer can be, for example, newly diagnosed, pretreated or refractory or relapsed. In some embodiments, a CD70-expressing cancer has at least about 15,000, at least about 10,000 or at least about 5,000 CD70 molecules/cell.

IX. Pharmaceutical Compositions Comprising Variant Target Binding Agent Conjugates and Administration Thereof A composition comprising a target binding agent (e.g., an antibody or derivative, alone or conjugated to a therapeutic agent) can be administered to a subject having or at risk of having an immunological disorder or a cancer. The invention further provides for the use of a target binding agent (e.g., an antibody or derivative, alone or conjugated to a therapeutic agent) in the manufacture of a medicament for prevention or treatment of cancer or immunological disorder. The term "subject" as used herein means any mammalian patient to which a target binding agent can be administered, including, e.g., humans and non-human mammals, such as primates, rodents, and dogs. Subjects specifically intended for treatment using the methods described herein include humans. The target binding agents can be administered either alone or in combination with other compositions in the prevention or treatment of the immunological disorder or a cancer.

Various delivery systems are known and can be used to administer the target binding agent. Methods of introduction include but are not limited to intradermal, intramuscular, intraperitoneal, intravenous, subcutaneous, intranasal, epidural, and oral routes. The target binding agent can be administered, for example by infusion or bolus injection (e.g., intravenous or subcutaneous), by absorption through epithelial or mucocutaneous linings (e.g., oral mucosa, rectal and intestinal mucosa, and the like) and can be administered together with other biologically active agents such as chemotherapeutic agents. Administration can be systemic or local.

In specific embodiments, the target binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-target binding agent does not absorb are used.

In other embodiments, the anti-target binding agent is delivered in a controlled release system. In one embodiment, a pump may be used (see Langer, 1990, *Science* 249:1527-1533; Sefton, 1989, *CRC Crit. Ref. Biomed. Eng.* 14:201; Buchwald et al., 1980, *Surgery* 88:507; Saudek et al., 1989, *N. Engl. J. Med.* 321:574). In another embodiment, polymeric materials can be used. (See *Medical Applications of Controlled Release* (Langer and Wise eds., CRC Press, Boca Raton, Fla., 1974); *Controlled Drug Bioavailability, Drug Product Design and Performance* (Smolen and Ball eds., Wiley, New York, 1984); Ranger and Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

A target binding agent (e.g., an antibody or derivative, alone or conjugated to a therapeutic agent) can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a target binding agent (e.g., an antibody or derivative, alone or conjugated to a therapeutic agent) in lyophilized form and (b) a second container containing a pharmaceutically acceptable diluent (e.g., sterile water) for injection. The pharmaceutically acceptable diluent can be used for reconstitution or dilution of the lyophilized target binding agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the target binding agent (e.g., an antibody or derivative, alone or conjugated to a therapeutic agent) that is effective in the treatment or prevention of an immunological disorder or a cancer can be determined by standard clinical techniques. In addition, in vitro assays may optionally be employed to help identify optimal dosage ranges. The precise dose to be employed in the formulation will also depend on the route of administration, and the stage of immunological disorder or cancer, and should be decided according to the judgment of the practitioner and each patient's circumstances. Effective doses may be extrapolated from dose-response curves derived from in vitro or animal model test systems.

For example, toxicity and therapeutic efficacy of the antibody or derivative can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A target binding agent (e.g., an antibody or derivative) that exhibits a large therapeutic index is preferred. Where a target binding agent exhibits toxic side effects, a delivery system that targets the target binding agent to the site of affected tissue can be used to minimize potential damage non-target antigen-expressing cells and, thereby, reduce side effects.

The data obtained from the cell culture assays and animal studies can be used in formulating a range of dosage for use in humans. The dosage of the target binding agent typically lies within a range of circulating concentrations that include the $ED_{50}$ with little or no toxicity. The dosage may vary within this range depending upon the dosage form employed and the route of administration utilized. For a target binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of the antigen binding agent administered to a patient with an immunological disorder or cancer is about 0.1 mg/kg to 100 mg/kg of the subject's body weight. More typically, the dosage administered to a subject is 0.1 mg/kg to 50 mg/kg of the subject's body weight, even more typically 0.1 mg/kg, 0.3 mg/kg, 0.5 mg/kg or 1 mg/kg to 20 mg/kg, 15 mg/kg, 12 mg/kg, 10 mg/kg, 7.5 mg/kg, 5 mg/kg or 3 mg/kg of the subject's body weight. Generally, human antibodies have a longer half-life within the human body than antibodies from other species due to the immune response to the foreign proteins. Thus, lower dosages of target binding agent comprising humanized or chimeric antibodies and less frequent administration is often possible.

A dose of a target binding agent can be administered, for example, daily, once per week (weekly), twice per week, thrice per week, four times per week, five times per week, biweekly, monthly or otherwise as needed.

In some embodiments, the dosage of an anti-target binding agent corresponds to a sub-optimal dosage (i.e., below the $EC_{50}$ for the anti-target binding agent (e.g., an antibody drug conjugate). For example, the dosage of an anti-target binding agent can comprise a dosage selected from the lowest 25%, lowest 15%, lowest 10% or lowest 5% of the therapeutic window. As used herein, the term "therapeutic window" refers to the range of dosage of a drug or of its concentration in a bodily system that provides safe and effective therapy.

In some embodiments, the dosage of a target binding agent is from about 0.05 mg/kg to about 1 mg/kg, or about 0.1 mg/kg to about 0.9 mg/kg, or about 0.15 to about 0.75 mg/kg of the subject's body weight. Such a dosage can be administered from 1 to about 15 times per week. Each dose can be the same or different. For example, a dosage of about 0.15 mg/kg of an anti-target binding agent can be administered from 1 to 10 times per four day, five day, six day or seven day period.

In some embodiments, the pharmaceutical compositions comprising the target binding agent can further comprise a therapeutic agent (e.g., a non-conjugated cytotoxic or immunomodulatory agent such as, for example, any of those described herein). The anti-target binding agent also can be co-administered in combination with one or more therapeutic agents for the treatment or prevention of immunological disorders or cancers. For example, combination therapy can include a therapeutic agent (e.g., a cytostatic, cytotoxic, or immunomodulatory agent, such as an unconjugated cytostatic, cytotoxic, or immunomodulatory agent such as those conventionally used for the treatment of cancers or immunological disorders). Combination therapy can also include, e.g., administration of an agent that targets a receptor or receptor complex other than the target antigen on the surface of activated lymphocytes, dendritic cells or cancer cells. An example of such an agent includes a second, antibody that binds to a molecule at the surface of an activated lymphocyte, dendritic cell or cancer cell. Another example includes a ligand that targets such a receptor or receptor complex. Typically, such an antibody or ligand binds to a cell surface receptor on activated lymphocytes, dendritic cell or cancer cell and enhances the cytotoxic or cytostatic effect of the target binding agent by delivering a cytostatic or cytotoxic signal to the activated lymphocyte, dendritic cell or cancer cell. Such combinatorial administration can have an additive or synergistic effect on disease parameters (e.g., severity of a symptom, the number of symptoms, or frequency of relapse).

With respect to therapeutic regimens for combinatorial administration, in a specific embodiment, an anti-target binding agent is administered concurrently with a therapeutic agent. In another specific embodiment, the therapeutic agent is administered prior or subsequent to administration of the target binding agent, by at least an hour and up to several months, for example at least an hour, five hours, 12 hours, a day, a week, a month, or three months, prior or subsequent to administration of the target binding agent. In some embodiments, the subject is monitored following administration of the anti-target binding agent, and optionally the therapeutic agent.

The therapeutic agent can be, for example, any agent that exerts a therapeutic effect on cancer cells or activated immune cells. Typically, the therapeutic agent is a cytotoxic or immunomodulatory agent. Such combinatorial administration can have an additive or synergistic effect on disease parameters (e.g., severity of a symptom, the number of symptoms, or frequency of relapse).

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, rapamycin (Sirolimus), streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In some embodiments, the therapeutic agent can be a combined therapy, such as CHOP (Cyclophosphamide, Doxorubicin, Prednisolone and Vincristine), CHOP-R (Cyclophosphamide, Doxorubicin Vincristine, Prednisolone, and rituximab), ICE (Idarubicin, high dose Cytosine arabinoside and Etoposide) or ABVD (Doxorubicin, Bleomycin, Vinblastine and Dacarbazine). Agents such as CC-1065 analogues, calicheamicin, maytansine, analogues of dolastatin 10, rhizoxin, and palytoxin can be linked to the variant target binding agent.

In specific embodiments, the cytotoxic or cytostatic agent is auristatin E or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. Patent Application Publication Nos. 20030083263 and 20050009751), International Patent Application Nos. PCT/US03/24209 and PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other anti-tubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the therapeutic agent is not a radioisotope. In some embodiments, the therapeutic agent is not ricin or saporin.

In certain embodiments, the therapeutic agent is an anti-VEGF agent, such as AVASTIN (bevacizumab) or NEXAVAR (Sorafenib); a PDGF blocker, such as SUTENT (sunitinib malate); or a kinase inhibitor, such as NEXAVAR (sorafenib tosylateor).

In some embodiments, the cytotoxic or immunomodulatory agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, Tositumomab, Trastuzumab, tretinoin, uracil mustard, vairubicin, vinblastine, vincristine, vinorelbine or zoledronate.

In additional embodiments, the therapeutic agent is an antibody, such as a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (MedImmune, Inc., MD; Campath UH (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); CEAcide (Immunomedics, NJ; a humanized anti-CEA antibody); or an anti-CD40 antibody (e.g., as disclosed in U.S. Pat. No. 6,838,261).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific membrane antigen, prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen, IL-2 receptor, CD20, CD52, CD30, CD33, CD22, human chorionic gonadotropin, CD38, CD40, mucin, P21, MPG, and Neu oncogene product.

In some embodiments, the therapeutic agent is an immunomodulatory agent. The immunomodulatory agent can be, for example, gancyclovir, etanercept, tacrolimus, cyclosporine, rapamycin, REVLIMID (lenalidomide), cyclophosphamide, azathioprine, mycophenolate mofetil or methotrexate.

Alternatively, the immunomodulatory agent can be, for example, a glucocorticoid (e.g., cortisol or aldosterone) or a glucocorticoid analogue (e.g., prednisone or dexamethasone).

In some typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists. In some embodiments, the immunomodulatory agent is a cytokine, such as G-CSF, GM-CSF or IL-2.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products Way 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SKandF-104493, Leo Denmark SR-2566, Tanabe T-757 and Teijin TEI-1338.

The invention is further described in the following examples, which are in not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or as otherwise known. Cell culture reagents were obtained from Invitrogen Corp., Carlsbad, Calif.

EXAMPLES

I. Production of Humanized Anti-CD70 Antibody Derivatives

Humanized anti-CD70 antibodies were generated as described in U.S. Patent Application No. 60/673,070, filed Apr. 19, 2005, and PCT International Publication No. WO 2006/113909; the disclosures of which are incorporated herein in its entirety for all purposes.

The nucleotide and amino acid sequences of the heavy and light variable regions of the anti-CD70 murine monoclonal antibody, 1F6, and a chimeric derivative of 1F6, c1F6, are set forth as SEQ ID NOS:1, 2, 21 and 22, respectively. (See also U.S. Patent Application No. 60/645,355, filed Jan. 19, 2005; and PCT International Publication No. WO 2006/113909). Human acceptor sequences for humanization of c1F6 were chosen from human germline exon $V_H$, $J_H$, Vκ and Jκ sequences. Acceptor sequences for c1F6 $V_H$ domain humanization were chosen from germline $V_H$ exons $V_H$1-18 (Matsuda et al., 1993, *Nature Genetics* 3:88-94) or $V_H$1-2 (Shin et al., 1991, *EMBO J.* 10:3641-3645) and $J_H$ exon $J_H$-6 (Mattila et al., 1995, *Eur. J. Immunol.* 25:2578-2582). Germline Vκ exon B3 (Cox et al., 1994, *Eur. J. Immunol.* 24:827-836) and Jκ exon Jκ–1 (Hieter et al., 1982, *J. Biol. Chem.* 257:1516-1522) were chosen as acceptor sequences for c1F6 $V_L$ domain humanization. 1F6 murine CDRs, determined according to the Kabat definition, were grafted onto the chosen human germline template. Briefly, synthetic overlapping oligonucleotides spanning the humanized $V_H$ or $V_L$ domain were generated and PCR overlap extension was used to assemble each domain. Restriction sites incorporated into the PCR product were used to directionally clone the $V_H$ and $V_L$ domains into a pCMV expression vector in frame with human IgG1 constant domains or kappa (κ) constant domain, respectively.

Several framework positions were chosen for reintroduction of mouse donor residues. These were positions H46, H67, H68, H69, H70, H71, H80, H81, H82, H82A and H91 in the $V_H$ domain, according to the Kabat numbering convention. No framework positions were altered in the $V_L$ domain, although mouse CDR1 residues at positions L25 and L33 were chosen for introduction of the human acceptor residue for that position.

Several derivatives of humanized 1F6 were generated by incorporating different combinations of mouse framework donor residues in the $V_H$ domain or human CDR residues in the $V_L$ domain. These derivatives are summarized in Table 2 and Table 3 below.

TABLE 2

| $V_H$ Derivative | VH Exon Acceptor Sequence | Donor Framework Residues |
|---|---|---|
| h$V_H$A | VH1-18 | H71, H91 |
| h$V_H$B | VH1-18 | H71 |
| h$V_H$C | VH1-18 | H91 |
| h$V_H$D | VH1-18 | none |
| h$V_H$E | VH1-2 | none |
| h$V_H$F | VH1-18 | H67, H68, H69, H70, H71 |
| h$V_H$G | VH1-18 | H80, H81, H82, H82A |
| h$V_H$H | VH1-18 | H67, H68, H69, H70, H71, H80, H81, H82, H82A |
| h$V_H$I | VH1-18 | H46, H71, H91 |
| h$V_H$J | VH1-2 | H46 |
| h$V_H$K | VH1-2 | H71 |
| h$V_H$L | VH1-2 | H46, H71 |
| h$V_H$M | VH1-18 | H46, H67, H68, H69, H70, H71 |
| h$V_H$N | VH1-18 | H69, H70, H71, H80 |

TABLE 3

| $V_L$ Derivative | Acceptor CDR Residue |
|---|---|
| h$V_L$A | none |
| h$V_L$B | L25 |
| h$V_L$C | L33 |
| h$V_L$D | L25, L33 |

II. In Vitro Activity of Humanized 1F6 Antibody Derivatives

1. Binding Affinity

Humanized 1F6 antibody derivatives HDLA (h$V_H$D and h$V_L$A), HHLA (h$V_H$H and h$V_L$A), and HJLA (h$V_H$J and h$V_L$A), and c1F6 were transiently expressed in 293 cells, labeled with europium using the Eu-N1 iodoacetamido chelate (Perkin Elmer), and analyzed for saturation binding to a panel of CD70 positive cell lines as described in detail in U.S. Patent Application No. 60/673,070, filed Apr. 19, 2005; and PCT International Publication No. WO 2006/113909. The results are shown below in Table 4.

TABLE 4

| Cell Line | Antigen/Cell | Apparent Binding Affinity $K_D$ (nM) | | | |
|---|---|---|---|---|---|
| | | c1F6 | h1F6 HDLA | h1F6 HHLA | h1F6 HJLA |
| ACHN | 30,000 | 0.30 | 1.44 | 0.29 | 0.68 |
| Caki-1 | 235,000 | 1.28 | 1.29 | 1.22 | 1.36 |
| Caki-2 | 99,000 | 0.26 | 0.86 | 0.15 | 0.37 |
| 786-O | 252,000 | 0.56 | 0.55 | 0.28 | 0.46 |

The $K_D$ values for the humanized 1F6 derivatives were very similar to c1F6 on all of the cell lines tested, confirming that the humanization process did not significantly reduce antigen-binding activity.

2. ADCC Activity

The ability of humanized 1F6 antibody derivatives HHLA, HJLA and HELA to mediate ADCC against CD70$^+$ cell lines was measured using a standard $^{51}$Cr release assay as described in detail in U.S. Patent Application No. 60/673,070, filed Apr. 19, 2005; and PCT International Publication No. WO 2006/113909. The derivatives of humanized 1F6 lysed CD70$^+$ target cells in a dose dependent manner, whereas murine CD70 antibody m1F6 and non-binding control human Ig were not effective.

3. CDC Activity

The ability of humanized 1F6 antibody derivative HJLA to mediate CDC on CD70$^+$ cell lines was examined, as described in detail in U.S. Patent Application No. 60/673,070, filed Apr. 19, 2005; and PCT International Publication No. WO 2006/113909. Using this assay, c1F6 and humanized 1F6 derivative HJLA mediated dose-dependent lysis of CD70$^+$ target cells in an equivalent manner.

4. ADCP Activity

The ability of humanized 1F6 antibody derivative HJLA to mediate phagocytosis on the CD70$^+$ renal cell carcinoma line 786-O was examined as described in detail in U.S. Patent Application No. 60/673,070, filed Apr. 19, 2005; and PCT International Publication No. WO 2006/113909. Using this assay, c1F6 and humanized 1F6 derivative HJLA, but not a non-binding control antibody, facilitated phagocytosis of CD70$^+$ target cells in an antibody-dose dependent fashion and to an equivalent degree.

5. Cytotoxicity

Drug conjugates of humanized 1F6 antibody derivatives were evaluated for in vitro cytotoxic activity as described in detail in U.S. Patent Application No. 60/673,070, filed Apr. 19, 2005; and PCT International Publication No. WO 2006/113909. Humanized 1F6 derivatives HELA (h$V_H$E and h$V_L$A), HHLA, HJLA and HMLA (h$V_H$M and h$V_L$A), and c1F6 were transiently expressed in 293 cells, conjugated to vcMMAF (described in U.S. patent application Ser. No. 10/983,340; published as U.S. Patent Publication No. 2005/0238649, Oct. 27, 2005) at a loading level of eight drug units per antibody, and tested for cytotoxicity on two CD70$^+$ cell lines. The results are shown below in Table 5.

TABLE 5

| h1F6-vcMMAF | No. of Mouse FR Residues | Caki-1 IC$_{50}$ [ng/ml] | 786-O IC$_{50}$ [ng/ml] |
|---|---|---|---|
| h1F6 HELA-F8 | 0 | 3.4 (mean = 2.87, n = 3) | 5.2 (mean = 3.9, n = 3) |
| h1F6 HHLA-F8 | 9 | 1.4 (mean = 1.87, n = 3) | 2.3 (mean = 1.93, n = 3) |
| h1F6 HJLA-F8 | 1 | 2.2 (mean = 2.3, n = 3) | 3.4 (mean = 3.03, n = 3) |
| h1F6 HMLA-F8 | 6 | 1.8 (mean = 2.07, n = 3) | 2.8 (mean = 2.03, n = 3) |
| c1F6(293)-F8 | 0 | 1.8 (mean = 2.17, n = 3) | 2.4 (mean = 1.45, n = 3) |

The IC$_{50}$ values for the four humanized derivatives were within two-fold of c1F6 on both cell lines tested.

III. In Vivo Activity of Humanized 1F6 Antibody Drug Conjugates

1. 786-O Renal Cell Carcinoma Model in Nude Mice

Humanized 1F6 antibody derivatives HDLA, HHLA, HJLA and HELA were transiently expressed in 293 cells, conjugated to mcMMAF (described in U.S. patent application Ser. No. 10/983,340; published as U.S. Patent Publication No. 2005/0238649, Oct. 27, 2005) at a loading level of eight drug units per antibody, and evaluated for in vivo efficacy in a 786-O renal cell carcinoma solid tumor model in nude mice as described in detail in U.S. Patent Application No. 60/673,070, filed Apr. 19, 2005; and PCT International Publication No. WO 2006/113909. The results indicated that tumor volume was greatly reduced in all antibody drug conjugate-treated mice in comparison to untreated mice, and all humanized 1F6 derivatives conjugated to mcMMAF were comparable in efficacy to c1F6 mcMMAF.

2. SCID Mouse Xenograft Models of Disseminated Lymphoma and Multiple Myeloma

Humanized 1F6 derivative HJLA was evaluated for in vivo antitumor activity in disseminated lymphoma and multiple myeloma xenograft mouse models as described in detail in U.S. Patent Application No. 60/673,070, filed Apr. 19, 2005; and PCT International Publication No. WO 2006/113909. The results showed that in each tumor model, survival of mice treated with humanized 1F6 derivative HJLA was significantly prolonged compared to that of untreated mice or mice receiving non-binding control antibody. In multiple myeloma xenografts, the level of tumor-derived monoclonal protein (λ light chain) in the sera of individual mice was examined. Circulating λ light chain concentrations were significantly lower in mice treated with humanized derivative 1F6 HJLA as compared to untreated mice, consistent with the increased survival rates of the mice.

3. In Vitro Deletion of $CD70^+$ Antigen-Specific T Cells

The ability of humanized 1F6 antibody derivative HJLA to deplete antigen-specific activated T cells was tested as described in detail in U.S. Patent Application No. 60/673,070, filed Apr. 19, 2005; and PCT International Publication No. WO 2006/113909. The addition of humanized 1F6 derivative HJLA significantly limited expansion of the antigen-specific $CD8^+/V\beta17^+$ cells in an antibody-dose dependent manner. These results showed that humanized 1F6 selectively targets and prevents the expansion of antigen-activated T cells. This activity was largely reversed when FcγRIII receptors were blocked with an anti-CD16 specific antibody, indicating that deletion of peptide-reactive cells was mediated via humanized 1F6 antibody interaction with FcγRIII-bearing effector cells.

4. Anti-CD70 Antibody Does Not Affect Antigen-Negative Bystander Cells

The effect of 1F6-mediated depletion on antigen-negative bystander T cells was determined as described in detail in U.S. Patent Application No. 60/673,070, filed Apr. 19, 2005; and PCT International Publication No. WO 2006/113909. As shown above, c1F6 and humanized 1F6 antibody derivatives were comparable in binding affinity, capacity to mediate effector functions, and ability to deplete activated CD8+ T cell subsets. Treatment with c1F6 antibody did not significantly perturb the relative representations of other CD8+ or CD4+ Vβ TCR families; no group was observed to be eliminated. These data demonstrated that exposure to anti-CD70 antibodies selectively depleted CD70+ activated T cells without causing detectable collateral damage to bystander T cell populations.

IV. Production of Variants of Humanized h1F6 Derivative HJLA

Antibody drug conjugates are prepared by site-specifically attaching cytotoxic drugs at sites with the antibody known to interact with Fcγ receptors (FcγR). Site specific drug attachment is accomplished by modification of one (or more) antibody residues by amino acid substitution with one or more non-conservative amino acids. In variation of this approach, site specific drug attachment is accomplished by modification of one (or more) antibody residues with one or cysteine residues and coupling cytotoxic drugs using thiol specific reagents such as maleimide derivatives of drugs. Alternatively, site-specific blockade of FcγR binding is accomplished by engineering a site for N-linked glycosylation in the Fc at or near the site that interacts with FcγR. These approaches are generally summarized as follows:

The following approach is used to replace one or more amino acids in or in proximity to an Fc domain involved in the binding interaction to one or more Fcγ receptors is followed:
i) Select key residues involved in the binding interaction between Fcγ receptors and Fc domains.
ii) Mutate one (or more key) contact residue (replace amino acid with a non-conservative amino acid).
iii) Express antibody variant in mammalian host and purify.
iv) Couple a maleimide derivative of a cytotoxic drug(s) (e.g., a maleimide linker coupled to a cytotoxic drug) to at least some of other solvent accessible cysteines.
v) Measure binding of binding of ADC to FcγR (see, e.g., Shields et al., 2001, *J. Biol. Chem.* 276:6591-6604).
vi) Characterize in vitro and in vivo anti-tumor activity of ADC (see, e.g., Doronina et al., 2003, *Nat. Biotechnol.* 21:778-784 and Francisco et al., 2003, *Blood* 102:1458-1465).

The following approach is used to introduce one or more cysteine residues in or in proximity to an Fc domain involved in the binding interaction to one or more Fcγ receptors:
i) Select key residues involved in the binding interaction between FcγR and Fc domains are selected.
ii) Mutate one (or more key) contact residue to cysteine (an engineered cysteine).
iii) Express the antibody variant in mammalian host and purify.
iv) Couple maleimide derivative of cytotoxic drugs (e.g., a maleimide linker coupled to a cytotoxic drug) to the engineered cysteine residue(s) and, optionally, at least some of other solvent accessible cysteines.
v) Determine binding of binding of variant ADC to FcγR as described by Shields et al., 2001, *J. Biol. Chem.* 276: 6591-6604.
vi) Characterize in vitro and in vivo anti-tumor activity of ADC (see, e.g., Doronina et al., 2003, *Nat. Biotechnol.* 21:778-784 and Francisco et al., 2003, *Blood* 102:1458-1465).

The following approach is used to introduce one or more sites for N-linked glycosylation in or in proximity to an Fc domain involved in the binding interaction to one or more Fcγ receptors is followed:
vii) Select key residues involved in the binding interaction between Fcγ receptors and Fc domains.
viii) Mutate group of three residues to create site for N-linked glycosylation: asparagine-any amino acid (X)-serine or asparagine-X-threonine, wherein X is not proline.
ix) Express antibody variant in mammalian host and purify.
x) Determine if the consensus glycosylation sites are utilized in the mammalian host for attachment of carbohydrate.
xi) Couple a maleimide derivative of a cytotoxic drug(s) (e.g., a maleimide linker coupled to a cytotoxic drug) to at least some of other solvent accessible cysteines.
xii) Measure binding of binding of ADC to FcγR (see, e.g., Shields et al., 2001, *J. Biol. Chem.* 276:6591-6604).
xiii) Characterize in vitro and in vivo anti-tumor activity of ADC (see, e.g., Doronina et al., 2003, *Nat. Biotechnol.* 21:778-784 and Francisco et al., 2003, *Blood* 102:1458-1465).

In these studies, residues involved in the binding interaction between Fcγ receptors and Fc domains can be identified, for example, as those residues that are functionally involved in the Fcγ receptor-Fc domains binding. (See generally, Shields et al., 2001, *J. Biol. Chem.* 276:6591-6604). Residues involved in the binding interaction between Fcγ receptors and Fc domains can also be identified as those present at the structural interface. (See generally, Sondermann et al., 2000, *Nature* 406(6793):267-73.)

The studies described herein below illustrate the effects of preventing or reducing the interaction of an ADC with FcγR on in vitro and in vivo efficacy of anti-CD70 ADC. A humanized 1F6 antibody was modified by either: i) replacing the IgG1 constant domain with the constant domains of IgG2 or IgG4; or ii) mutating amino acid residues in the Fc domain of the IgG1 constant domain known to be important for binding to FcγR.

1. Isotype Variants

Humanized 1F6 antibody derivative HJLA (hV$_H$J and hV$_L$A) was selected as template for modification of the Fc domain as described infra. As described in detail supra, the humanized 1F6 derivative HJLA contains the hV$_H$J variable heavy chain fused to a human IgG1 constant domains and the hV$_L$A variable light chain fused to a kappa (κ) constant domain. The nucleotide and amino acid sequences of the h1F6 hV$_H$J variable heavy chain are provided in SEQ ID NOs:13 and 14, respectively, and the nucleotide and amino acid sequences of the h1F6 hV$_H$J variable heavy chain fused to the human IgG1 constant domains are provided in SEQ ID NOs:15 and 16, respectively. The nucleotide and amino acid sequences of the h1F6 hV$_L$A variable light chain is provided in SEQ ID NOs:23 and 24, respectively, and the nucleotide and amino acid sequences of the h1F6 hV$_L$A variable light chain fused to the κ constant domain are provided in SEQ ID NOs:25 and 26, respectively.

The amino acid sequences of the constant domains of the human IgG1, IgG2, IgG3 and IgG4 isotypes are shown in FIG. 2.

Isotype variants of humanized 1F6 antibody derivative HJLA, in which the constant domain of IgG1 was replaced with the constant domain of IgG2 or IgG4, were generated generally as described above, except that human IgG2 or IgG4 constant regions were used.

The amino acid sequences of the IgG2 and IgG4 isotype variants of the h1F6 derivative HJLA are shown in FIG. 3.

Further isotype variants of humanized anti-CD70 antibodies (e.g., h1F6) can be similarly generated, including, for example, IgG1 isotype variants in which portions of the IgG1 constant domain in proximity to the Fc domain involved in the binding interaction to one or more Fcγ receptors are replaced by the analogous domains from IgG2, IgG3 or IgG4.

2. Fc Domain Variants

Variants of humanized 1F6 antibody derivative HJLA, in which amino acid residues in the Fc domain of IgG1 known to be important for binding to FcγR were mutated to impair binding to one or more FcγR, were generated using standard molecular biology techniques.

Two engineered h1F6 variants were generated. h1F6 IgG1v1 contains the following mutations: E233P:L234V: L235A, which grossly impair binding to FcγRI, FcγRIIA, FcγRIIB and FcγRIIIA, but have minimal impact upon binding to FcRn (Armour et al., 1999, *Eur. J. Immunol.* 29:2613-24). h1F6 IgG4v3 contains the following mutations: S228P: L235A:G237A:E318A (Hutchins et al., 1995, *Proc. Natl. Acad. Sci. USA* 92:11980-4). The S228P mutation makes the hinge "IgG$_1$ like" (CPPC), which favors inter-heavy chain over intra-heavy chain disulfide bond pairing (Angal et al., 1993, *Mol. Immunol.* 30:105-108; Bloom et al., 1997, *Protein Sci.* 6:407-415). The alanine mutations are known to impair binding to FcγR and C1q (Hutchins et al., supra).

The amino acid sequences of the IgG1 and IgG4 Fc domain variants of the h1F6 derivative HJLA (IgG1v1 and IgG4v3) are shown in FIG. 4.

Further Fc domain variants of humanized anti-CD70 antibodies (e.g., h1F6) can be similarly generated, including, for example, Fc domain variants with one or more non-conservative amino acid substitutions, introduction of one or more cysteine residues, or introduction of one or more sites for N-linked glycosylation, in or in proximity to the Fc domain involved in the binding interaction to one or more Fcγ receptors.

Figure 5:
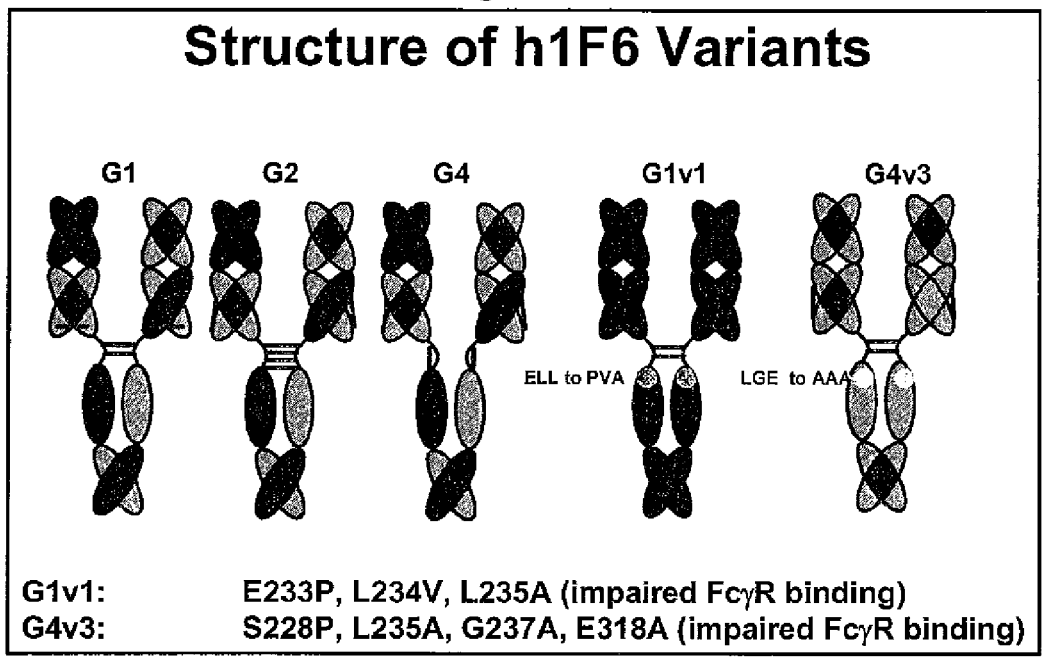
FIG. 5 is a schematic diagram depicting the structure of humanized anti-CD70 (h1F6) and variant h1F6 antibodies. G1, G2 and G4 indicate antibodies having the constant regions of the IgG1, IgG2 and IgG4 isotypes, respectively. G1v1 indicates the 1hF6 IgG1 variant having the E233P, L234V and L235A amino acid substitutions, which result in impaired FcγR binding. G4v3 indicates the 1hF6 IgG4 variant having the S228P, L235A, G237A and E318A amino acid substitutions, which result in impaired FcγR binding.

FIG. 5 is a schematic diagram depicting the structure of humanized anti-CD70 antibody (h1F6) variants. G1, G2 and G4 indicate antibodies having the constant domains of the IgG1, IgG2 and IgG4 isotypes, respectively. G1v1 indicates the 1hF6 IgG1 variant having the E233P, L234V and L235A amino acid substitutions which result in impaired FcγR binding. G4v3 indicates the 1hF6 IgG4 variant having the S228P, L235A, G237A and E318A amino acid substitutions which result in impaired FcγR binding.

Using these methods and similar methods, variant target binding agents can be generated that bind to CD70 or other target antigens.

V. In Vitro Binding of Variant h1F6 Antibodies to FcγReceptor-Bearing Cells

Fcγ receptor (FcγR) expression is widespread on normal human immune cells and may contribute to non-target tissue uptake of ADCs. Human IgG1 isotype antibodies bind with higher efficiency to FcγR than do IgG4 and IgG2 isotypes. Mutation of the Fc residues involved in FcγR binding, or altering Ig isotype, was predicted to decrease ADC localization to non-target organs, resulting in reduced toxicity, increased circulating ADC concentrations and improved tumor targeting. A panel of h1F6 IgG isotype and Fc binding variant ADCs were generated to test the effects of reduced FcγR binding on ADC efficacy and toxicity. See FIG. 5.

Figure 6:
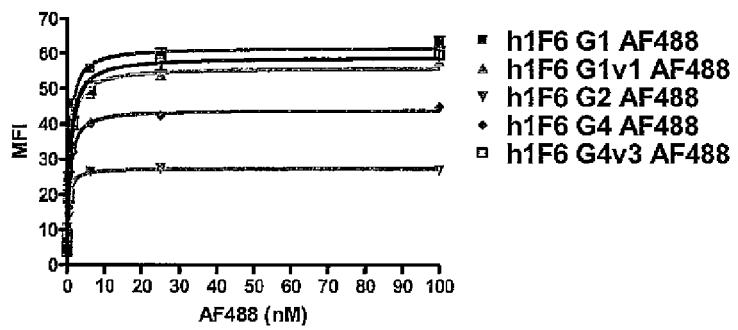
FIG. 6 shows the binding affinity of humanized anti-CD70 (h1F6) and variant h1F6 antibodies to CD70-expressing 786-O cells. Each antibody (G1, G1v1, G2, G4, and G4v3 as indicated) was reduced and labeled with Alexa Fluor 488 $C_5$ maleimide (AF488), and serial dilutions were incubated with 786-O cells. Labeled cells were detected using an LSRII FACS analyzer, and data was analyzed using a one site binding model equation using Prism v4.01. Apparent binding affinity data indicate that altering IgG isotype (G1, G2, G4) or mutating the Fc backbone (G1v1, G4v3) does not impact antigen-binding activity.

Both IgG2 and IgG4 isotypes interacted with Fcγ receptors with lower affinity than the IgG1 isotype (see FIG. 6).

Cell-based assays were developed to confirm reduced binding of variant h1F6 antibodies to human FcγRI and FcγRIIIa, and to demonstrate that each h1F6 variant retains antigen-binding activity.

Variant h1F6 antibodies were assessed for antigen-binding activity. Briefly, each variant h1F6 antibody was reduced and labeled with Alexa Fluor 488 C$_5$ maleimide (AF488). CD70 positive 786-O cells (FIG. 6) or L428 cells (not shown) were then combined with serial dilutions of each labeled antibody. Labeled cells were detected using an LSRII FACS analyzer. Data was analyzed using a one site binding model equation using Prism v4.01. Apparent binding affinity data (Table 6) indicate that altering IgG isotype (G1, G2, G4) or mutating the Fc backbone (G1v1, G4v3) does not impact antigen-binding activity.

TABLE 6

Summary of Variant h1F6 Antibody Binding to CD70⁺ 786-O and L428 Cell Lines

|  | 786-O Cells | | | L428 Cells | | |
| --- | --- | --- | --- | --- | --- | --- |
|  | AF/Ab | Avg $K_D$ | Std Dev | AF/Ab | Avg $K_D$ | Std Dev |
| h1F6 G1 | 3.4 | 1.27 | 0.121 | 3.4 | 0.311 | 0.017 |
| h1F6 G1v1 | 3.6 | 1.13 | 0.249 | 3.6 | 0.288 | 0.041 |
| h1F6 G2 | 4.4 | 0.95 | 0.309 | 4.4 | 0.110 | 0.031 |
| h1F6 G4 | 4.2 | 1.14 | 0.339 | 4.2 | 0.253 | 0.058 |
| h1F6 G4v3 | 4.3 | 1.30 | 0.081 | 4.3 | 0.325 | 0.077 |

Using this assay and similar assays, variant target binding agents can be assessed for binding to CD70 or to other target antigens.

VI. Production of Stable FcγRI- and FcγRIIIa-Expressing CHO Cell Lines

Cell-based competition binding assays were established to study the interactions of variant h1F6 antibodies with human Fcγ receptor I (FcγRI) and Fcγ receptor IIIa (FcγRIIIa).

Figure 7:
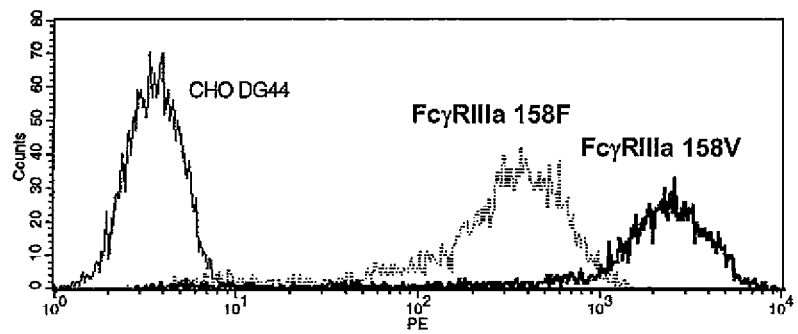
FIG. 7 shows cell surface expression of FcγRIIIa in transfected CHO cells. The parent cell line, CHO DG44, and two cell lines stably transfected with a full-length FcγRIIIa expression vector, 158F and 158V, were analyzed by FACS using a phycoerythrin (PE)-conjugated anti-human FcγRIIIa antibody.

The full length human FcγRI and FcγRIIIa receptors were stably expressed in CHO cells and cell lines were isolated by limited dilution cloning. FIG. 7 shows cell surface expression of FcγRIIIa in the parent cell line, CHO DG44, and two cell lines stably transfected with a full-length FcγRIIIa expression vector, 158F and 158V. Cell surface FcγRIIIa was analyzed by FACS using a phycoerythrin (PE)-conjugated anti-human FcγRIIIa antibody.

Using these or other cell lines, variant target binding agents can be assessed for binding to FcγRI and FcγRIIIa receptor-expressing cells.

Figure 8:
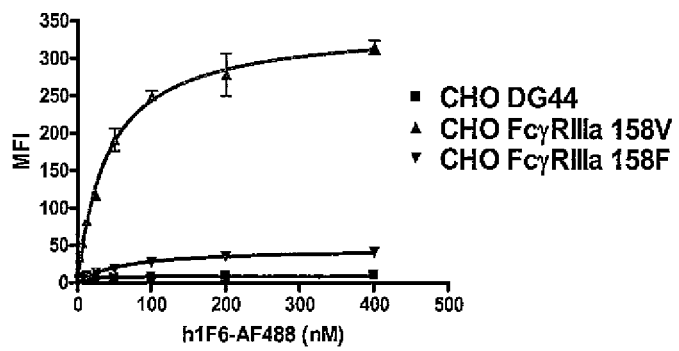
FIG. 8 shows binding of humanized anti-CD70 (h1F6) antibodies to CHO cells expressing full-length FcγRIIIa. The parent cell line, CHO DG44, and two cell lines stably transfected with a full-length FcγRIIIa expression vector, 158F and 158V, were incubated with AF488-labeled h1F6 antibody. Labeled cells were detected using an LSRII FACS analyzer.

VII. In Vitro Binding of Variant h1F6 Antibodies to Stable FcγRI- and FcγRIIIa-Expressing CHO Cell Lines Binding of humanized anti-CD70 (h1F6) antibody to CHO cells expressing full-length FcγRIIIa was determined by saturation binding. The parent cell line, CHO DG44, and two cell lines stably transfected with a full-length FcγRIIIa expression vector, 158F (low affinity) and 158V (high affinity), were incubated with AF488-labeled h1F6 antibody. Labeled cells were detected using an LSRII FACS analyzer. FIG. 8 shows that h1F6 antibody binds to length FcγRIIIa-expressing cells.

Binding of variant humanized anti-CD70 (h1F6) antibodies to CHO cells expressing full-length FcγRIIIa was also determined by competition binding. A stable CHO cell line expressing human FcγRIIIa, 158V, was combined with serial dilutions of the parental h1F6 IgG1 or h1F6 variants in the presence of 100 nM Alexa Fluor 488 labeled h1F6 IgG1. Labeled cells were detected using an LSRII FACS analyzer. The binding interactions of h1F6 IgG1 and variants to FcγRIIIa were comparable to reports in the literature. Only h1F6 IgG1 (open triangle) interacted significantly with FcγRIIIa (FIG. 9, left panel).

Figure 9:
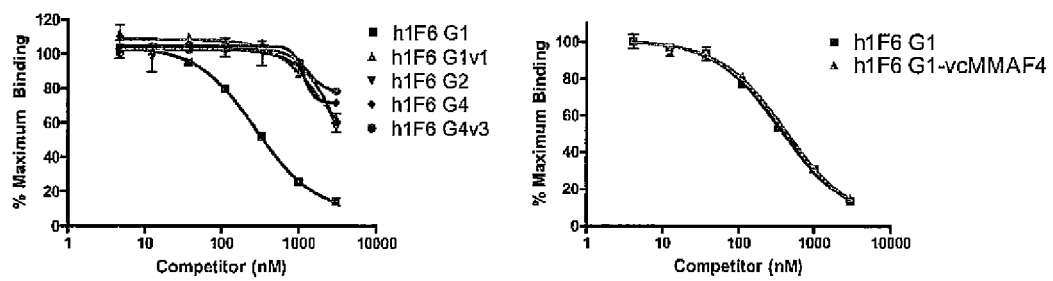
FIG. 9 shows competition binding of humanized anti-CD70 (h1F6) and variant h1F6 antibodies to CHO cells expressing full-length FcγRIIIa. A stable CHO cell line expressing full-length human FcγRIIIa, 158V, was isolated by limiting dilution cloning and combined with serial dilutions of the parental h1F6 IgG1 or h1F6 variants in the presence of 100 nM Alexa Fluor 488 labeled h1F6 IgG1. Labeled cells were detected using an LSRII FACS analyzer. The binding interactions of h1F6 IgG1 and h1F6 variants to FcγRIIIa expressing cells were comparable to literature reports. Only h1F6 IgG1 (open triangle) interacted significantly with FcγRIIIa (left panel). Conjugation of h1F6 IgG1 with the auristatin derivative MMAF did not affect binding of the antibody to FcγRIIIa (right panel).

Conjugation of h1F6 IgG1 with a mean loading of 4 auristatin MMAF/antibody did not significantly affect binding of the antibody to FcγRIIIa (FIG. 9, compare left and right panels).

Binding of humanized anti-CD70 (h1F6) antibody to CHO cells expressing full-length FcγRI was determined by competition binding. A stable CHO cell line expressing human FcγRI was combined with serial dilutions of the parental h1F6 IgG1 or h1F6 variants in the presence of 50 nM Alexa Fluor 488 labeled h1F6 IgG1. Labeled cells were detected using an LSRII FACS analyzer. The binding interactions of h1F6 IgG1 and variants to FcγRI were comparable to reports in the literature. h1F6 IgG1 (open triangle) and h1F6 IgG4 (open inverted triangle) bound to FcγRI with high affinity while h1F6 IgG2 and variants h1F6 IgG1v1 and IgG4v3 diamonds) bound with reduced affinity and showed no significant interaction (FIG. 10, left panel).

Figure 10:
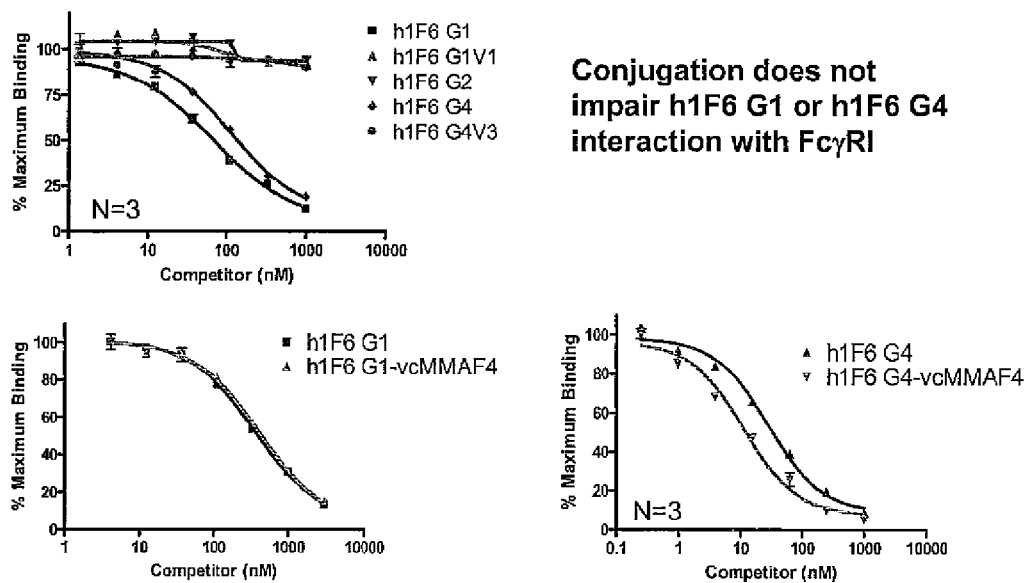
FIG. 10 shows competition binding of humanized anti-CD70 (h1F6) and variant h1F6 antibodies to CHO cells expressing full-length FcγRI. A stable CHO cell line expressing full-length human FcγRI was isolated by limited dilution cloning and combined with serial dilutions of the parental h1F6 IgG1 or h1F6 variants in the presence of 50 nM Alexa Fluor 488 labeled h1F6 IgG1. Labeled cells were detected using an LSRII FACS analyzer. The binding interactions of h1F6 IgG1 and h1F6 variants to both FcγRI were comparable to literature reports. h1F6 IgG1 (open triangle) and h1F6 IgG4 (inverted open triangle) showed a similar pattern of high affinity binding to FcγRI, whereas no significant interaction was observed with the other variants, IgG1v1 (open diamond), IgG2 (open square), and IgG4v3 (open circle) (left panel). Conjugation of h1F6 IgG1 or h1F6 IgG4 with the auristatin derivative MMAF (IgG1-F4 and IgG4-F4, respectively) did not affect binding of these antibodies to FcγRI (right panel).

Conjugation of h1F6 IgG1, h1F6 IgG1v1, h1F6 IgG2, h1F6 IgG4 or h1F6 IgG4v3 with a mean loading of 4 auristatin MMAF/antibody did not affect binding of the antibody to FcγRI (FIG. 10, compare left and right panels).

Using these and similar assays, variant target binding agents can be assessed for binding to FcγRI and FcγRIIIa receptor-expressing cells.

VIII. In Vitro Binding of Variant h1F6 Antibody Drug Conjugates to Stable FcγRI- and FcγRIIIa-Expressing CHO Cell Lines h1F6 IgG1 and h1F6 variants were conjugated to vcMMAF with a mean loading of 4 drugs/antibody.

Using the above-described assays or variations on such assays, variant target binding agent drug conjugates can be assessed for binding to FcγRI and FcγRIIIa receptor-expressing cells.

IX. In Vitro Efficacy of Variant h1F6 Antibody Drug Conjugates

Growth inhibition assays were performed on a panel of CD70 positive cell lines: 786-O, Caki-1, L428, UMRC-3 and LP1, and a CD70 negative cell line: HCT-116. Cells were treated with serial dilutions of h1F6 IgG1 vcMMAF(4), h1F6 IgG1v1 vcMMAF(4), h1F6 IgG2 vcMMAF(4), h1F6 IgG4 vcMMAF(4) and h1F6 IgG4v3 vcMMAF(4). No significant differences in cytotoxicity were observed between the h1F6 variant drug conjugates across the CD70+ cell line panel (Table 7).

TABLE 7

$IC_{50}$ Values for Variant h1F6 vcMMAF(4) Conjugates on CD70⁺ Cell Panel

| h1F6-ADCs (# CD70 Receptors) | 786-O 190,000 | Caki-1 136,000 | L428 105,000 | UMRC-3 70,000 | LP-1 34,000 | HCT-116 (CD70⁻) |
| --- | --- | --- | --- | --- | --- | --- |
| h1F6 G1v1-vcMMAF(4) | 9 | 5 | 3 | 29 | 22 | No effect |
| h1F6 G2-vcMMAF(4) | 16 | 7 | 25 | 31 | 34 | No effect |
| h1F6 G4-vcMMAF(4) | 26 | 17 | 18 | 35 | 42 | No effect |
| h1F6 G4v3-vcMMAF(4) | 22 | 8 | 14 | 26 | 28 | No effect |
| h1F6 G1-vcMMAF(4) | 8 | 6 | 3 | 34 | 21 | No effect |

Using this assay or related assays, variant target binding agent drug conjugates can be assessed for cytotoxic activity on target antigen expressing cells.

X. Variant h1F6 Antibody Drug Conjugates with Introduced Cysteine Residues

Variants of humanized 1F6 antibody were prepared by mutating amino acid residues in the Fc domain of IgG1 that are involved in the binding of the Fc domain to FcγR. The mutations were generated using standard molecular biology techniques.

Six engineered h1F6 variants were generated. h1F6 IgG1 G236C contains a glycine to cysteine substitution at position 236; h1F6 IgG1 P238C contains a proline to cysteine substitution at position 238; h1F6 IgG1 S239C contains a serine to cysteine substitution at position 239; h1F6 IgG1 D265C contains an aspartate to cysteine substitution at position 265; h1F6 IgG1 E269C contains a glutamate to cysteine substitution at position 269; and h1F6 IgG1 A327C contains an alanine to cysteine substitution at position 327. The antibodies were purified by standard methods.

Cell-based assays were developed to confirm reduced binding of four of the variant h1F6 antibodies to human FcγRI and FcγRIIIa, and to demonstrate that each h1F6 variant retains antigen-binding activity. Variant antibody S239C was conjugated to vcMMAF as described supra or can be conjugated as described in Published U.S. Application No. 2007-092940 or Givol et al. (supra).

The variant h1F6 antibodies were assessed for antigen-binding activity, as described above. Apparent binding affinity data (Table 8) indicate that the introduction of cysteine substitutions in the Fc region did not substantially impair binding.

TABLE 8

Binding Affinity of Anti-CD70 Cys mutants

| Humanized anti-CD70 (h1F6) variants | 786-O KD IgG (nM) | cell binding IC50 IgG-vcF2 IC50 IgG |
|---|---|---|
| IgG1 | 0.6 | 1.3 |
| IgG1 S239C | 1.0 | 1.1 |
| IgG1 D265C | 1.1 | 0.9 |
| IgG1 E269C | 0.8 | 0.9 |
| IgG1 A327C | 0.5 | 1.1 |

Figure 11:
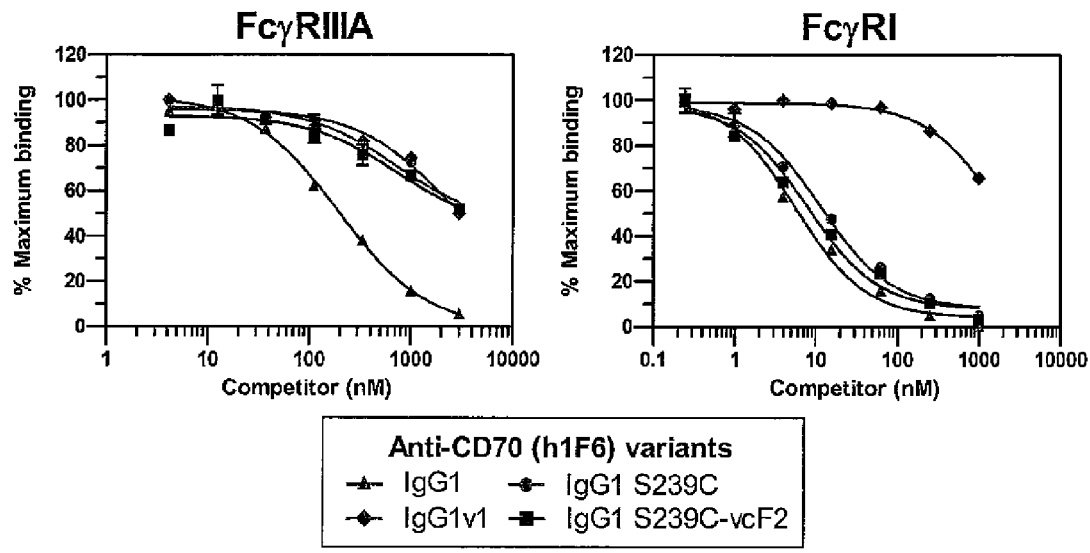
FIG. 11 shows competition binding of a variant h1F6 antibodies with introduced cysteine substitution, S239C (EU index, as set forth in Kabat), to CHO cells expressing full-length FcγRIIIa (left panel) or FcγRI (right panel). The assays were performed as described previously. The IgG1 S239C variant, either unconjugated or conjugated to vcMMAF (average of 2 drugs/antibody) exhibited reduced binding to FcγRIIIa-expressing cells, but not FcγRI-expressing cells. The control, parent antibody h1F6, binds to FcγRIIIa-expressing cells and FcγRI-expressing cells.

Binding of one of the variants, IgG1 S239C, to CHO cells expressing full-length FcγRIIIa and FcγRI was determined as described above. Referring to FIG. 11, the IgG1 S239C variant, either unconjugated or conjugated to vcMMAF (average of 2 drugs/antibody) exhibited reduced binding to FcγRIIIa-expressing cells, but not FcγRI-expressing cells. The control, parent antibody h1F6, binds to FcγRIIIa-expressing cells and FcγRI-expressing cells.

Further Fc domain variants can be similarly generated, including, for example, Fc domain variants with one or more cysteine amino acid substitutions at, for example, positions 234, 235, 237, 267, 298, 299, 326, 330, or 332. Using the assays described, variant target binding agents can be assessed for binding to FcγRI and FcγRIIIa receptor-expressing cells.

XI. In Vivo Efficacy of Variant h1F6 Antibody Drug Conjugates

Figure 12:
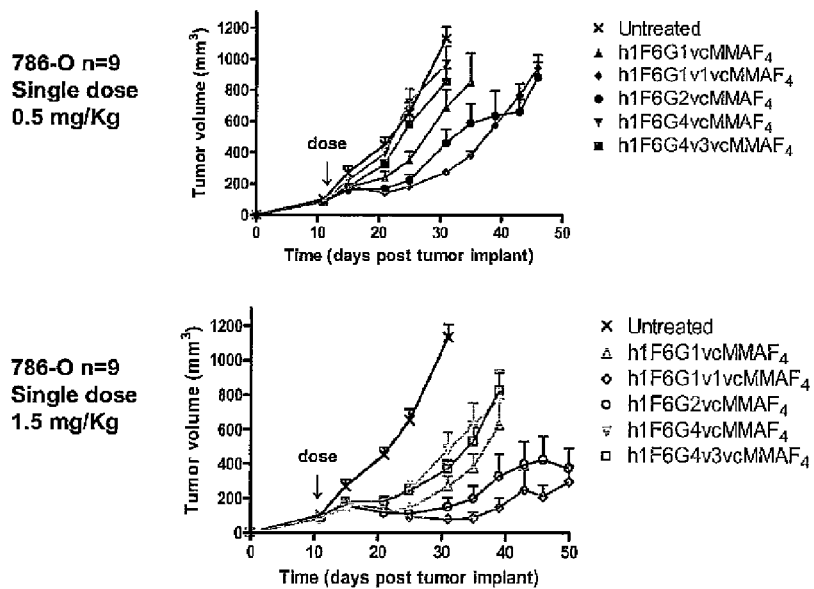
FIG. 12 shows in vivo efficacy of humanized anti-CD70 (h1F6) and variant h1F6 antibody drug conjugates in a 786-O renal cell carcinoma xenograft model. Nude mice, which were injected subcutaneously with 786-O renal cell carcinoma cells, were treated with a single i.v. administration of either 0.5 mg/kg (top panel) or 1.5 mg/kg (bottom panel) of indicated h1F6 or h1F6 variant antibody-MMAF drug conjugate once the mean tumor volume reached 100 mm³. Nine (9) animals were dosed for each treatment group and six (6) animals were dosed with vehicle alone. The in vivo efficacy studies indicated that: h1F6 IgG1v1 vcMMAF4 (diamonds) had enhanced efficacy compared to h1F6 IgG1 vcMMAF4 (triangles); h1F6 IgG2 vcMMAF4 (circles) also had improved efficacy compared to h1F6 IgG1 vcMMAF4 (triangles); h1F6 IgG4v3 vcMMAF4 (squares) had equivalent efficacy compared to h1F6 IgG4 vcMMAF4 (inverted triangles); and h1F6 IgG1v1 vcMMAF4 (diamonds) had enhanced efficacy compared to h1F6 IgG4v3 vcMMAF4 (squares).

In vivo efficacy data suggests that decreasing FcγR binding improves the potency of an ADC. In a renal cell carcinoma xenograft model, nude mice were injected subcutaneously with 786-O cells and then were treated with a single i.v. administration of either 0.5 mg/kg (FIG. 12, top panel) or 1.5 mg/kg (FIG. 12, bottom panel) of each variant humanized anti-CD70 antibody (h1F6) drug conjugate once the mean tumor volume reached 100 mm$^3$. Nine (9) animals were dosed for each treatment group and six (6) animals were dosed with vehicle alone. Surprisingly, this in vivo efficacy study indicated that: h1F6 IgG1v1 vcMMAF4 (diamonds) had enhanced efficacy compared to h1F6 IgG1 vcMMAF4 (triangles); h1F6 IgG2 vcMMAF4 (circles) also had improved efficacy compared to h1F6 IgG1 vcMMAF4 (triangles); and h1F6 IgG1v1 vcMMAF4 (diamonds) had enhanced efficacy compared to h1F6 IgG4v3 vcMMAF4 (squares). Despite greatly decreased FcγR binding of h1F6 IgG4 (inverted triangles) and h1F6 IgG4v3 (squares), the drug conjugates of these molecules were less efficacious than the parent h1F6 IgG1 (triangles) drug conjugate.

Figure 13:
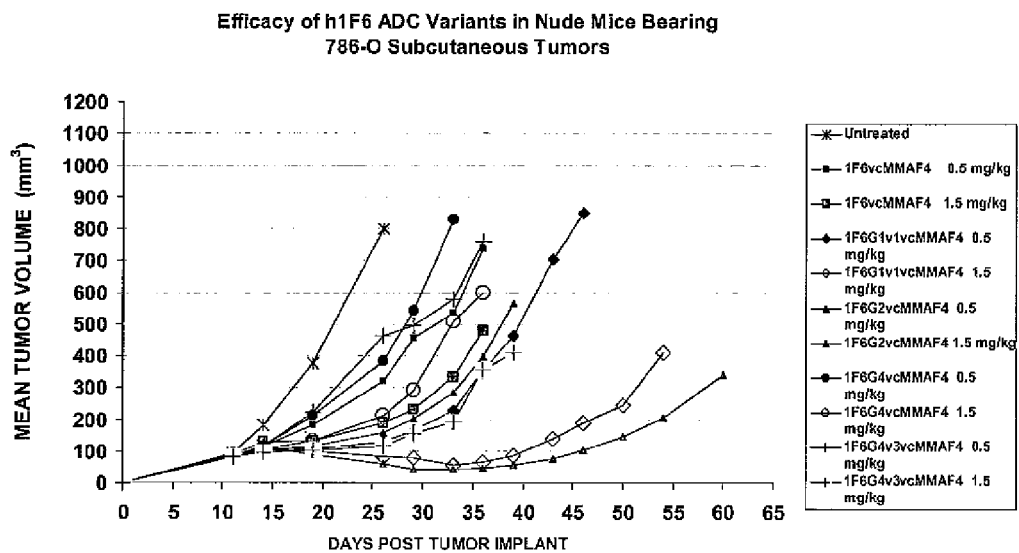
FIG. 13 shows in vivo efficacy of humanized anti-CD70 (h1F6) and variant h1F6 antibody drug conjugates in a 786-O renal cell carcinoma xenograft model. Nude mice, which were injected subcutaneously with 786-O renal cell carcinoma cells, were treated with a single i.v. administration of either 0.5 mg/kg or 1.5 mg/kg of indicated h1F6 or variant h1F6 antibody-MMAF drug conjugate once the mean tumor volume reached 100 mm³. Nine (9) animals were dosed for each treatment group and six (6) animals were dosed with vehicle alone. The in vivo efficacy studies indicated that: h1F6 IgG1v1 vcMMAF4 (diamonds) had enhanced efficacy compared to h1F6 IgG1 vcMMAF4 (squares); h1F6 IgG2 vcMMAF4 (triangles) also had improved efficacy compared to h1F6 IgG1 vcMMAF4 (squares); h1F6 IgG4v3 vcMMAF4 (crosses) had equivalent efficacy compared to h1F6 IgG4 vcMMAF4 (circles); and h1F6 IgG1v1 vcMMAF4 (diamonds) had enhanced efficacy compared to h1F6 IgG4v3 vcMMAF4 (crosses).

A second in vivo study is shown in FIG. 13. Nude mice injected subcutaneously with 786-O renal cell carcinoma cells were treated with a single i.v. administration of either 0.5 mg/kg or 1.5 mg/kg of each h1F6 variant-MMAF drug conjugate once the mean tumor volume reached 100 mm$^3$. Nine (9) animals were dosed for each treatment group and six (6) animals were dosed with vehicle alone. The in vivo efficacy studies indicated that: h1F6 IgG1v1 vcMMAF4 (diamonds) had enhanced efficacy compared to h1F6 IgG1 vcMMAF4 (squares); h1F6 IgG2 vcMMAF4 (triangles) also had improved efficacy compared to h1F6 IgG1 vcMMAF4 (squares); h1F6 IgG4v3 vcMMAF4 (crosses) had equivalent efficacy compared to h1F6 IgG4 vcMMAF4 (circles); and h1F6 IgG1v1 vcMMAF4 (diamonds) had enhanced efficacy compared to h1F6 IgG4v3 vcMMAF4 (crosses).

Figure 14:
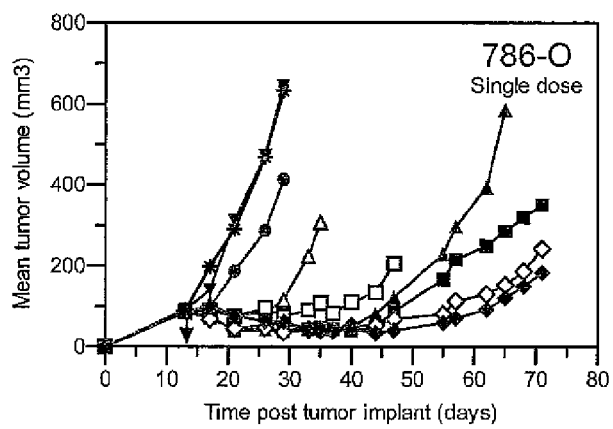
FIG. 14 shows in vivo efficacy of humanized anti-CD70 (h1F6) antibody drug conjugate in a 786-O renal cell carcinoma xenograft model. Nude mice, which were injected subcutaneously with 786-O renal cell carcinoma cells, were treated with a single i.v. administration of either 1.5 mg/kg or 4.5 mg/kg of each h1F6 variant-mcMMAF drug conjugate once the mean tumor volume reached 100 mm³. The in vivo efficacy studies indicated that: h1F6 IgG1v1 mcMMAF4 (diamonds) had enhanced efficacy compared to h1F6 IgG1 mcMMAF4 (triangles); h1F6 IgG2 vcMMAF4 (squares) also had improved efficacy compared to h1F6 IgG1 vcMMAF4 (triangles).

A third in vivo study is shown in FIG. 14. Nude mice injected subcutaneously with 786-O renal cell carcinoma cells were treated with a single i.v. administration of either 1.5 mg/kg or 4.5 mg/kg of each h1F6 variant-mcMMAF drug conjugate once the mean tumor volume reached 100 mm$^3$. The in vivo efficacy studies indicated that: h1F6 IgG1v1 mcMMAF4 (diamonds) had enhanced efficacy compared to h1F6 IgG1 mcMMAF4 (triangles); h1F6 IgG2 vcMMAF4 (squares) also had improved efficacy compared to h1F6 IgG1 vcMMAF4 (triangles).

Figure 15:
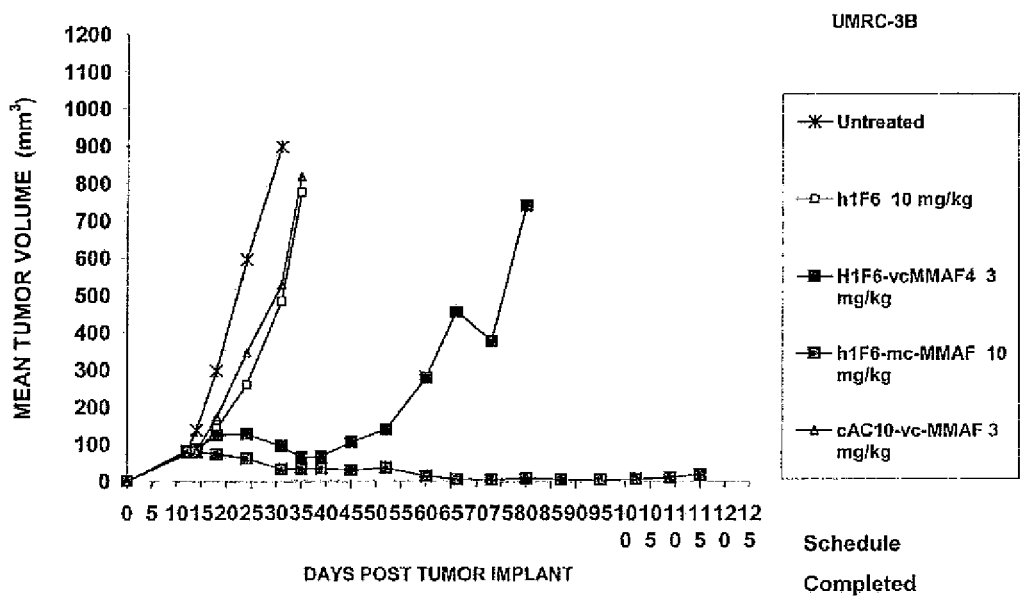
FIG. 15 shows in vivo efficacy of humanized anti-CD70 (h1F6) antibody drug conjugates in a UMRC-3 renal cell carcinoma xenograft model. Nude mice, which were injected subcutaneously with UMRC-3 renal cell carcinoma cells, were treated with q4dx4 i.v. administration of vehicle (untreated), 10 mg/kg h1F6 antibody, 3 mg/kg h1F6 antibody-MMAF drug conjugate h1F6 vcMMAF4, 10 mg/kg h1F6 antibody-MMAF drug conjugate h1F6 mcMMAF, or 3 mg/kg control antibody-MMAF drug conjugate cAC10 vcMMAF once the mean tumor volume reached 100 mm³. Nine (9) animals were dosed for each treatment group and six (6) animals were dosed with vehicle alone. The in vivo efficacy studies indicated that: h1F6 vcMMAF4 (blue squares) and h1F6 mcMMAF (red squares) had efficacy compared to unconjugated h1F6 (open squares) or a control cAC10 antibody MMAF drug conjugate (triangles).

A fourth in vivo study was performed to assess the difference in activity of the variant h1F6 antibody drug conjugates in a different CD70$^+$ renal cell carcinoma xenograft model. UMRC-3 renal cell carcinoma cells injected into nude mice form tumors; these sizes of these tumors can be significantly reduced by treatment with h1F6 antibody-MMAF drug conjugates but not with unconjugated h1F6 antibody (see FIG. 15). Nude mice were injected subcutaneously with UMRC-3 renal cell carcinoma cells. Treatment with the indicated amounts of antibody was initiated when the tumor volume reached approximately 100 mm$^3$. Animals were dosed q4dx4 i.v. with no antibody (untreated), 1 mg/kg 1F6vcMMAF4, 3 mg/kg 1F6vcMMAF4, 1 mg/kg 1F6G1v1vcMMAF4, 3 mg/kg 1F6G1v1vcMMAF4, 1 mg/kg 1F6G2vcMMAF4, 3 mg/kg 1F6G2vcMMAF4, 1 mg/kg 1F6G4vcMMAF4, 3 mg/kg 1F6G4vcMMAF4, 1 mg/kg 1F6G4v3vcMMAF4, or 3 mg/kg 1F6G4v3vcMMAF4. The measured end point of the study was tumor volume. To determine the in vivo pharmacokinetics of the variant h1F6 antibodies, blood (saphenous, 20 µl) was drawn for each group immediately prior to each dose, and then 1 h, 6 h, 2 d, 4 d after the fourth dose.

In a related study, animals were dosed q4dx4 i.v. with no antibody (untreated), 3 mg/kg 1F6vcMMAF4, 6 mg/kg 1F6vcMMAF4, 3 mg/kg 1F6G1v1vcMMAF4, 6 mg/kg 1F6G1v1vcMMAF4, 3 mg/kg 1F6G2vcMMAF4, 6 mg/kg 1F6G2vcMMAF4, 3 mg/kg 1F6G4vcMMAF4, 3 mg/kg 1F6G4vcMMAF4, 3 mg/kg 1F6G4v3vcMMAF4, or 6 mg/kg 1F6G4v3vcMMAF4. The measured end point of the study was tumor volume. To determine the in vivo pharmacokinetics of the variant h1F6 antibodies, blood (saphenous, 20 µl) was drawn for each group immediately prior to each dose, and then 1 h, 6 h, 2 d, 4 d after the fourth dose.

Figure 16A:
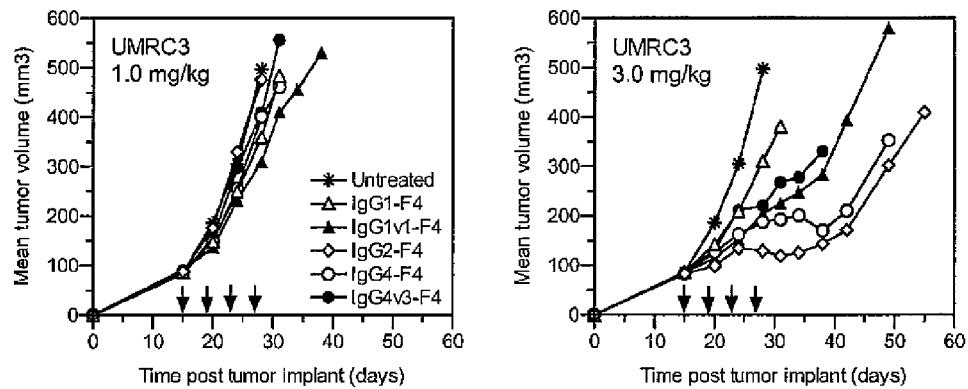
FIG. 16 shows in vivo efficacy of humanized anti-CD70 (h1F6) antibody drug conjugates and variants in a UMRC-3 renal cell carcinoma xenograft model. Nude mice were injected subcutaneously with UMRC-3 renal cell carcinoma cells. Treatment with the indicated amounts of antibody was initiated when the tumor volume reached approximately 100 mm³. Referring to panel A, animals were dosed q4dx4 i.v. with no antibody (untreated), 1 mg/kg or 3 mg/kg of 1F6vcMMAF4, 1F6G1v1vcMMAF4, 1F6G2vcMMAF4, 1F6G4vcMMAF4 or 1F6G4v3vcMMAF4. The measured end point of the study was tumor volume. Referring to panel b, animals were dosed q4dx4 i.v. with no antibody (untreated), 3 mg/kg or 6 mg/kg of 1F6vcMMAF4, 1F6G1v1vcMMAF4, 1F6G2vcMMAF4, 1F6G4vcMMAF4 or 1F6G4v3vcMMAF4. The measured end point of the study was tumor volume.

Referring to FIG. 16A, the in vivo efficacy studies indicated that: h1F6 vcMMAF4 and all variants ADCs had similar efficacy when doses at 1 mg/kg. In contrast, at 3 mg/kg, IgG2 vcMMAF4 (diamonds) and IgG4 vcMMAF4 (circles) had somewhat enhanced efficacy compared to h1F6 IgG1 vcMMAF4 (open triangles), h1F6 IgG4v3 vcMMAF4 (closed circles) and h1F6 IgG1v1 vcMMAF4 (closed triangles) and the control 1F6 IgG4 vcMMAF4 (crosses).

Figure 16B:
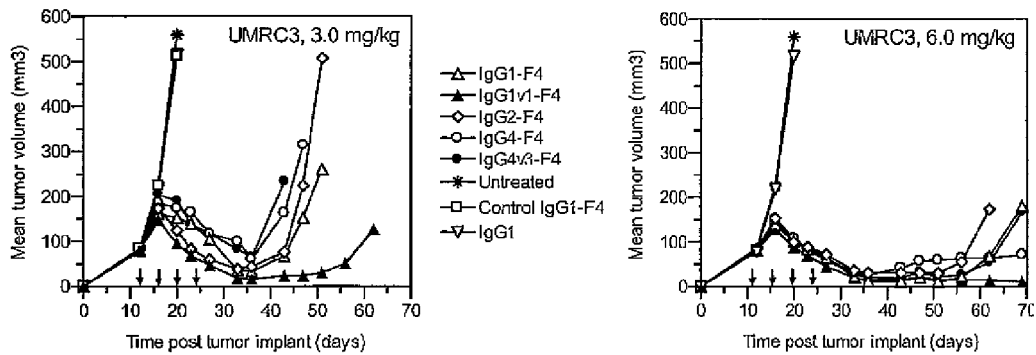

Referring to FIG. 16B, the in vivo efficacy studies indicated that: at 3 mg/kg h1F6 IgG1v1 vcMMAF4 (closed triangles) had the best efficacy, while h1F6 IgG1 vcMMAF4 (open triangles), h1F6 IgG2 vcMMAF4 (diamonds), h1F6 IgG4 vcMMAF4 (circles) and h1F6 IgG4v3 vcMMAF4 (closed circles) had similar but somewhat enhanced efficacies. At 6 mg/kg h1F6 IgG1 vcMMAF4 and all variant antibodies showed similar efficacies.

Using these assays or related assays, variant binding agent drug conjugates can be assessed for in vivo efficacy against target antigen-expressing tumors.

XII. Maximum Tolerated Doses of Variant h1F6 Antibody Drug Conjugates in Mice To determine the maximum tolerated dose (MTD) of the antibody variants, groups of Balb/c mice (n=3) were injected with 40, 60 or 80 mg/kg ADCs variants via the tail vein to determine the single dose maximum tolerated dose. Mice were monitored daily for 14 days, and both weight and clinical observations were recorded. Mice that developed significant signs of distress were euthanized.

The anti-CD70 antibody, h1F6, binds to human CD70 but does not cross-react with the corresponding antigen from mice. Thus, antigen-independent but not antigen-dependent toxicities of the anti-CD70 ADCs can be explored in mice. All ADCs were tolerated to ≥40 mg/kg with IgG2-F4 being slightly better tolerated (≥60 mg/kg). Thus IgG2-F4 and IgG1v1-F4 have a therapeutic index that is improved by at least 2-fold compared to the parent IgG1-F4 ADC.

XIII. In Vivo Pharmacokinetics of Variant h1F6 Antibody Drug Conjugates

In the study described in Example X, blood was drawn from three (3) mice treated with the 1.5 mg/kg dose of each h1F6 antibody variant vcMMAF drug conjugate at 1 hr, 1 d, 7 d and 14 d post drug administration. Serum concentrations of antibody-drug conjugates at these time points were measured using an anti-idiotype binding ELISA.

Figure 17:
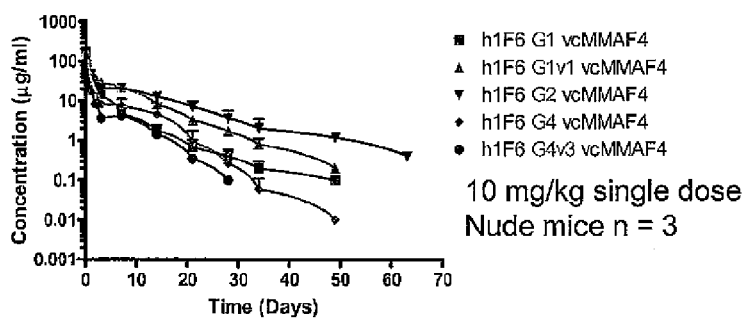
FIG. 17 shows the in vivo pharmacokinetics of humanized anti-CD70 (h1F6) and variant h1F6 antibody drug conjugates. Mice were treated as described in FIG. 11. Blood was drawn from three (3) mice treated with the 1.5 mg/kg dose of each h1F6 or variant h1F6 antibody-MMAF drug conjugate at 1 hr, 1 d, 7 d and 14 d post-drug administration. Serum concentrations of the antibody drug conjugates at these time points were measured using an anti-idiotype binding ELISA. h1F6 IgG1v1 vcMMAF4 (triangles) and h1F6 IgG2 vcMMAF4 (inverted triangles) cleared more slowly from the circulation compared to h1F6 IgG1 vcMMAF4 (squares). h1F6 IgG4 vcMMAF4 (diamonds) and h1F6 IgG4v3 vcMMAF4 (circles) cleared more slowly from the circulation compared to h1F6 IgG1 vcMMAF4 (squares).

Referring to FIG. 17, h1F6 IgG1v1 vcMMAF4 (triangles) and h1F6 IgG2 vcMMAF4 (inverted triangles) cleared more slowly from the circulation compared to h1F6 IgG1 vcMMAF4 (squares). h1F6 IgG4 vcMMAF4 (diamonds) and h1F6 IgG4v3 vcMMAF4 (circles) also cleared more slowly from the circulation as compared to h1F6 IgG1 vcMMAF4 (squares). The faster clearance of human IgG4 compared to human IgG1 or IgG2 from mouse circulation was not unexpected as this has been observed previously (Zuckier et al., 1994, *Cancer* 73:794-799). The more rapid clearance of IgG4 and IgG4v3 drug conjugates from the mouse circulation compared to IgG1, IgG2 and IgG1v1 drug conjugates likely occur though FcγR-independent mechanisms. The clearance data is also summarized in Table 9. As illustrated in the table, the improved potency of IgG1v1 and IgG2 variant drug conjugates correlates with exposure (AUC).

Reduction of FcγR binding by engineering the Fc domain of IgG1 can improve efficacy, and potentially the therapeutic window, by reducing non-target organ uptake thus increasing circulating antibody drug conjugate concentrations and improving tumor uptake.

Using this assay or a related assay, a variant target binding agent drug conjugates can be evaluated for in vivo pharmacokinetics.

TABLE 9

| Antibody-drug conjugate safety and pharmacokinetics | | | | | |
|---|---|---|---|---|---|
| | IgG1-F4 | IgG1v1-F4 | IgG2-F4 | IgG4-F4 | IgG4v3-F4 |
| Safety | | | | | |
| MTD (mg/kg)* | ≥40 | ≥40 | ≥60 | ≥40 | ≥40 |
| Pharmacokinetic variables† | | | | | |
| $T_{1/2}$ (days) | 5.4 ± 1.1 | 5.3 ± 0.7 | 5.9 ± 1.2 | 2.8 ± 0.3 | 3.7 |
| AUC (day-μg/ml) | 200 ± 23 | 432 ± 19 | 469 ± 115 | 204 ± 74 | 97 |
| Clearance (ml/day/kg) | 51 ± 5 | 23 ± 1 | 23 ± 5 | 61 ± 17 | 103 |

XIV. In Vivo Tissue Distribution of Variant h1F6 Antibody Drug Conjugates

The in vivo tissue distribution of humanized h1F6 and variant h1F6 antibody-drug conjugates (ADC) was investigated. Mice were injected subcutaneously with 786-O renal carcinoma cells as described supra, and then 1.5 mg/kg h1F6 G1 vc[$^3$H]MMAF or h1F6 G1v1 vc[$^3$H]MMAF was administered intravenously. At 4 hours, 1 day and 3 days post-injection, free [$^3$H]MMAF and/or [$^3$H]MMAF-ADC was measured in the serum, tumor and tissues (i.e., liver, kidney, intestine, intestinal contents and spleen). Tumor and tissues were homogenized in the presence of methanol (i.e., the [$^3$H]MMAF-ADC precipitates). The suspension contains total drug (i.e., [$^3$H]MMAF-ADC plus [$^3$H]MMAF), and the supernatant contains free drug (i.e., [$^3$H]MMAF).

The variant h1F6 G1v1-vcMMAF appeared to clear from the serum more slowly than h1F6 G1-vcMMAF at all three time points (4 hours, 1 days and 3 days). (Note that the assay measures both free MMAF and MMAF conjugated to the h1F6 antibody.)

The total [$^3$H]MMAF rapidly appeared in the tumors, with the 4 hour measurement being close to later time points; the free [$^3$H]MMAF appeared in the tumors more slowly. At 4 hours, most [$^3$H]MMAF appeared ADC bound, while free [$^3$H]MMAF dominated at later time points. At 72 h, more free [$^3$H]MMAF appeared in the tumors of mice treated with variant h1F6 G1v1 as compared to h1F6 G1. It is possible that the increased half-life of the variant h1F6 G1v1-vc[$^3$H]MMAF in the circulation contributes to the increased presence of [$^3$H]MMAF in the tumors.

At four hours mice injected with the variant h1F6 G1v1-vc[$^3$H]MMAF had significantly lower drug (ADC-bound and free) in the liver and intestine than mice injected with h1F6 G1v1-vc[$^3$H]MMAF. These differences, however, were lost at the later time points. This data is consistent with the liver being responsible for ADC degradation followed by biliary excretion.

The variant h1F6 G1v1-vcMMAF appeared to clear from the kidney and spleen more slowly than h1F6 G1-vcMMAF, similar to the results obtained in the serum.

In summary, by measuring [³H]MMAF-ADC, the variant h1F6 G1v1 clears more slowly from the circulation than h1F6 G1, consistent with the in vivo pharmacokinetics (see infra). In the tumor, more free [³H]MMAF appears in the tumor at 3 days post-injection for the variant h1F6 G1v1 as compared to h1F6 G1, consistent with higher in vivo potency. The higher [³H]MMAF-ADC concentration in serum appears to be a driver for higher tumor free drug concentration. Lower [³H] MMAF-ADC and free [³H]MMAF were observed in liver, intestine, and intestine contents at 4 h for the variant h1F6 G1v1 as compared to h1F6 G1. Finally, the kidney and spleen have [³H]MMAF-ADC concentrations similar to serum, but free drug at 4 h is lower for the variant h1F6 G1v1 as compared to h1F6 G1. These results are consistent with reduced binding of an ADC to Fc gamma receptors being associated with longer serum half-life and increased drug accumulation in the tumor.

Using these assays or related assays, variant target binding agent drug conjugates can be evaluated for in vivo biodistribution.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein, the disclosures of each of which is incorporated herein by reference in its entirety.

---

What is claimed is:

1. A variant target binding agent conjugate, comprising:
   a binding region that comprises an antibody Fv region or an antigen binding fragment thereof that specifically binds to a target antigen, wherein the target antigen is CD33;
   at least a portion of a Fc region of a human immunoglobulin IgG1 constant region, comprising an introduced cysteine residue at amino acid position 239, that is S239C, according to the EU index as set forth in Kabat; and
   a therapeutic agent conjugated directly or via a linker to the introduced cysteine residue, wherein the therapeutic agent exerts a cytotoxic or cytostatic effect on a cell that expresses CD33.

2. The variant target binding agent of claim 1, wherein the therapeutic agent is conjugated to the introduced cysteine residue via a linker.

3. The variant target binding agent of claim 2, wherein the therapeutic agent is conjugated to the introduced cysteine residue via a maleimide group of the linker.

4. The variant target binding agent conjugate of claim 2, wherein the therapeutic agent is a cytotoxic agent that exerts a cytotoxic effect on a cell that expresses CD33.

5. The variant target binding agent conjugate of claim 4, wherein the cytotoxic agent is a DNA minor groove binding agent.

6. The variant target binding agent of claim 5, wherein the DNA minor groove binding agent is a DNA minor groove alkylating agent.

7. The variant target binding agent conjugate of claim 3, wherein the therapeutic agent is a cytotoxic agent that exerts a cytotoxic effect on a cell that expresses CD33.

8. The variant target binding agent conjugate of claim 7, wherein the cytotoxic agent is a DNA minor groove binding agent.

9. The variant target binding agent of claim 8, wherein the DNA minor groove binding agent is a DNA minor groove alkylating agent.

10. The variant target binding agent conjugate of claim 4, wherein the cytotoxic agent is an anti-tubulin agent.

11. The variant target binding agent conjugate of claim 1, wherein the therapeutic agent is an auristatin, an enediyne, a lexitropsin, a duocarmycin, a taxane, a puromycin, a dolastatin, a maytansinoid, or a vinca alkaloid.

12. The variant target binding agent conjugate of claim 1, wherein the variant target binding agent conjugate is an intact antibody conjugated to a therapeutic agent.

13. The variant target binding agent conjugate of claim 7, wherein the variant target binding agent conjugate is an intact antibody conjugated to a therapeutic agent.

14. A composition comprising a variant target binding agent comprising a binding region that comprises an antibody Fv region or an antigen binding fragment thereof that specifically binds to a target antigen, wherein the target antigen is CD33;
- at least a portion of a Fc region of a human immunoglobulin IgG1 constant region, comprising an introduced cysteine residue at amino acid position 239, that is S239C, according to the EU index as set forth in Kabat; and
- a therapeutic agent conjugated directly or via a linker to the introduced cysteine residue, wherein the therapeutic agent exerts a cytotoxic effect on a cell that expresses CD33; and at least one pharmaceutically compatible ingredient.

15. The composition of claim 14, wherein the therapeutic agent is conjugated to the introduced cysteine residue via a linker.

16. The composition of claim 15, wherein the therapeutic agent is conjugated to the introduced cysteine residue via a maleimide group of the linker.

17. The composition of claim 16, wherein the cytotoxic agent is a DNA minor groove binding agent.

18. The composition of claim 15, wherein the variant target binding agent conjugate is an intact antibody conjugated to a therapeutic agent.

19. The composition of claim 15 wherein there is an average of two therapeutic agents per antibody in the composition.

* * * * *